United States Patent [19]

Weaver et al.

[11] Patent Number: 5,055,390

[45] Date of Patent: Oct. 8, 1991

[54] PROCESS FOR CHEMICAL MANIPULATION OF NON-AQUEOUS SURROUNDED MICRODROPLETS

[75] Inventors: James C. Weaver, Sudbury; Gregory B. Williams, Tewksbury; Jonathan G. Bliss, Somerville, all of Mass.

[73] Assignee: Massachusetts Institute of Technology, Cambridge, Mass.

[21] Appl. No.: 185,156

[22] Filed: Apr. 22, 1988

[51] Int. Cl.$^5$ .................. C12Q 1/02; C12Q 1/18; C12N 11/04

[52] U.S. Cl. .......................................... 435/5; 435/29; 435/30; 435/34; 435/39; 435/32; 435/7.1; 435/177; 435/182; 435/6; 436/528; 436/535; 428/402.2

[58] Field of Search ............... 425/29, 30, 34, 39, 425/32, 5, 7, 177, 182, 7.1; 264/4.1; 436/518, 528, 535; 427/212; 428/402.2, 402.21, 402.24

[56] References Cited

U.S. PATENT DOCUMENTS

| | | | |
|---|---|---|---|
| 4,399,219 | 8/1983 | Weaver | 435/29 X |
| 4,401,755 | 8/1983 | Weaver | 435/29 X |
| 4,495,509 | 1/1985 | Chao | 503/215 |
| 4,643,968 | 2/1987 | Weaver | 435/29 X |
| 4,647,536 | 3/1987 | Mosbach et al. | 435/177 |
| 4,649,109 | 3/1987 | Perlman | 435/182 X |
| 4,801,529 | 1/1989 | Perlman | 435/5 |

FOREIGN PATENT DOCUMENTS 0109861  5/1984  European Pat. Off. .
0114756  8/1984  European Pat. Off. .

OTHER PUBLICATIONS

J. C. Weaver, *Biotechnology and Bioengineering Symp.,* 17:185–195, (1986).
Lehninger, A. L., in *Biochemistry,* Second Edition, Worth Publishers, New York, N.Y., 1975, pp. 87–89.

*Primary Examiner*—Esther L. Kepplinger
*Assistant Examiner*—Toni R. Scheiner
*Attorney, Agent, or Firm*—Hamilton, Brook, Smith & Reynolds

[57] ABSTRACT

A process for the chemical manipulation of liquid and gel microdroplets is disclosed. The process involves providing first microdroplets having aqueous interiors, such that the first microdroplets are surrounded by a non-aqueous fluid. The aqueous interior chemical composition of the first microdroplets is then manipulated by exposure to compounds soluble in both the non-aqueous and aqueous phases, or by exposure to emulsions or suspensions of second microdroplets such that contact between the first and second microdroplets is made. This allows chemical manipulation to be accomplished without removing the first microdroplets from a non-aqueous fluid environment.

11 Claims, No Drawings

PROCESS FOR CHEMICAL MANIPULATION OF NON-AQUEOUS SURROUNDED MICRODROPLETS

GOVERNMENT SUPPORT

The government has rights to this invention as it was sponsored in part by the National Institutes of Health by Grant RO1GM34077 and by the Army Research Office by Contract Number DAAG29-85-K-0241 and by Grant Number DAAG29-84-G-0066.

BACKGROUND OF THE INVENTION

Measurement, analysis and isolation of desirable cells is a well established goal of much of industrial microbiology and biotechnology, with many important applications in fields such as clinical microbiology, cancer diagnosis and treatment, environmental science, food safety, toxicology, and research and development in basic and applied biology.

The importance of such isolation and prior methods for accomplishing isolation are well known (see, for example, Queener and Lively in *Manual of Industrial Microbiology and Biotechnology*, Demain and Solomon (Eds.), American Soc. Microbiol., Washington, D.C., 155-169, 1986; White et al, ibid, pp. 24-31). Selection strategies, which are based on preferential growth and recovery of desired cells, are often possible. For example, selection can be accomplished by genetically manipulating cells such that a desired trait is coupled with resistance to antibiotics or to the ability to grow in the absence of certain compounds. However, there are many cases in which selection does not work well or does not work at all. In such instances, cells are often isolated by screening, i.e. by methods wherein cells are cloned, identified and one or more desirable properties measured, such that a particular clone is identified, physically removed, and thereby isolated.

One well established application of screening methods for microorganisms involves cells which have been exposed to mutagenic conditions, or to genetic splicing procedures, such that a large population of cells results, but of which only a very small number of cells are successes, e.g. cells which both grow and produce a desired molecule at a high level. Plating of such cells on petri dishes such that separated colonies arise is then followed by chemical assays. In such assays, a successful colony which is scored positive (+) by use of radioimmunoassay, or is colored through use of a colorimetric indicator. The number of cells in such colonies is typically large. For example, in the case of cells which are microorganisms such as bacteria, such colonies typically contain between $10^7$ and $10^9$ cells. Cells from successful colonies are then removed and suspended in a medium such that the number of cells can be enumerated, and the accumulated amount or the production rate of a desired molecule can be quantitatively determined. As is evident from this brief description, this type of procedure requires several steps. Currently, the procedure is generally carried out using relatively macroscopic entities and manual procedures, such as petri dishes (for initial colony formation), visual inspection (for identifying positive colonies), physical manipulation (for colony removal and suspension), physical measurement (for cell enumeration by light scattering or other means) chemical assay (for determination of molecule concentrations at different times) and calculation (for comparison of molecule production rate to known rates).

Screening is often much more difficult when a producing strain already exists, and the task is to seek rare mutants which produce the same molecule, but at higher rates, or to higher final concentrations. In such cases, the first step of scoring positive cells is unnecessary, but then all cells must be quantitatively assayed for relative productivity. This is generally a very time consuming task. Because of the several macroscopic manipulations and assays, a typical screening task can involve formation of many initial colonies and significant manual labor.

The importance of measurement of biological entities, and the prior methods for accomplishing such measurement are also well known, with applications in fields such as clinical microbiology, cancer diagnosis and treatment, environmental science, food safety, toxicology, and research and development in basic and applied biology. Measurements relating to biological entities such as cells, virus, nucleic acids and antibody-antigen complexes are of general interest. Although a significant number of assays and tests are directed towards virus, nucleic acids and antibody-antigen complexes, the most well established methods for determining measurements of such biological entities relates to measurements of cells. For this reason, the main features of prior methods for the process for manipulation and measurement of non-aqueous surrounded microdroplets are presented with an emphasis on prior methods for determining cell growth.

Present cell analysis methods involve two major classes of assays. The first class rapidly detects and identifies specific cells directly from a primary sample, but does not determine cell viability. The most widely used in this class are specific ligand binding assays, e.g. immunoassays and genetic probes. However, they require many cells, and do not distinguish between dead and viable cells. This restricts their use to samples in which sufficient numbers of cells are present, and to determinations in which direct assessment of the physiological state of the cell is irrelevant. The second class of assays is used for viable cell determinations either directly using the primary sample, or using a subculture of the primary sample. The most traditional and widely used method is the plate count, which allows determination of single cell viability, based on growth, under many test conditions (see, for example, Hattori *The Viable Count: Quantitative and Environmental Aspects*, Brock/Springer, Madison, 1988). An important attribute of viable plate enumeration is that time required to obtain a determination is independent of the concentration of the cell in the sample, because formation of each colony proceeds from an initial single cell. The major disadvantage is its slowness, as typical determinations require one-half to several days, and are also labor- and materials-intensive.

The disadvantages of viable plating can better be appreciated by drawing attention to its basic attributes. Viable plating is a well established, important method for qualitatively determining the growth of cells, particularly the presence or absence of growth for given conditions, and is often based on the growth of initial cells into distinct colonies. Viable plating typically involves the spreading of a suspension of cells onto the surface of a gel-containing petri dish, with or without the pouring of a gel layer over the first gel surface. The gels are provided with nutrients, such that following an incubation period at a suitable temperature, many generations of growth occur. This leads to formation of visible colonies. For many microorganisms formation of visible colonies requires growth for 22 to 30 generations and therefore produces colonies containing $10^7$ to $10^9$ cells. (See Sharpe, in *Mechanizing Microbiology*, A. N. Sharpe and D. S. Clark (Eds.) Charles C. Thomas, Springfield, 19-40, 1978). Although conventional viable plating leads to formation of colonies, and thereby provides a basis for counting viable cells by counting colonies, the presence or absence of colonies only allows inference that the conditions present in the gel support do or do not support growth. For this reason, conventional viable plating is not well suited to quantitative determinations such as cell growth rate and lag time, because viable plating based on visual inspection counts the number of colonies formed, but does not determine how the cellular material or amount of cellular constituents in the colonies varies with time. An additional complication arises because the nutrient and metabolite concentrations within a colony comprise a microenvironment, which generally changes with time in an unknown way as microcolonies increase to form larger colonies with many cells in close proximity. The microenvironment within a large colony can also have significant heterogeneity of chemical composition within the microcolony, so that different cells within a large colony experience different growth conditions. Further, although some methods are based on a straightforward extension and application of scanning optical methods for determination of optical properties of colonies on or in gel slabs, such methods suffer from relatively large cost and size, and, because of the relatively large gel slab size, do not allow incubation conditions to be changed rapidly at the site of the cells within the gel. (See Glaser in *New Approaches to the Identification of Microorganisms Proceedings of a Symposium on Rapid Methods and Automation in Microbiology*, C.-G. Hedén and T. Illéni (Eds.), Wiley, New York, 3-12, 1975).

Instrumented methods for rapidly determining cell or culture growth and/or metabolic activity have been developed which only partially address the limitations of the viable plate assay. These include optical techniques for growth determination such as those which measure the change in light scattering due to many cells in a liquid suspended culture (See, for example, Edberg and Berger, in *Rapid Methods and Automation in Microbiology and Immunology*, K. O. Habermehl, Ed., SpringerVerlag, Berlin, 215-221, 1985), and a variety of metabolic activity based techniques which measure changes due to many cells in an analyzed sample. Examples of these include changes in extracellular pH (See, for example, *Cowan and Steel's Manual for the Identification of Medical Bacteria*, Cambridge University Press, Cambridge, 1974; *Manual of Methods for General Bacteriology*, P. Gerhardt, (Ed). American Society for Microbiology, Washington, 1981 ), carbon dioxide release (see, for example, Courcol et al., J. Clin. Microbiol., 25: 26-29, 1986; Manca et al., J. Clin. Microbiol., 23: 401-403, 1986), electrical impedance (see, for example, Stewart, J. Exp. Med., 4: 235-245, 1899; Eden and Eden *Impedance Microbiology*, Research Studies Press, Letchworth, 1984; Hadley and Yajko, in Instrumental Methods for Rapid Microbiological Analysis, Nelson (Ed.), VCH, Weinheim, 193-209, 1985; Bishop and White, J. Food Protect, 49: 739-753, 1986), chemiluminescence (see, for example, Neufeld et al., in *Instrumental Methods for Rapid Microbiological Analysis*, Nelson (Ed.), VCH, Weinheim, 51-65, 1985; *Rapid Methods and Automation in Microbiology and Immunology*, Habermehl (Ed.), Springer-Verlag, Berlin, 1985) or fluorescence (see, for example, Rossi and Warner in *Instrumental Methods and Automation in Microbiology and Immunology*, Habermehl (Ed.), Springer-Verlag, Berlin, 1985). A disadvantage of all such metabolic activity methods is that they are based on combined effects of a large number of cells. Therefore, this generally requires an initial process, based on plating, to obtain initial colonies for purposes of inoculation of the analyzed sample, such that the determinations based on many cells at least are based on a monopopulation, i.e. a population comprised norminally of the same type of cells. For this reason, although a total population cell determination may itself be rapid, it is generally preceeded by a viable plating method, or its equivalent, which is slow. Thus, the total analysis time, counted from receipt of a primary or non-plated sample to a cell growth determination, is the sum of both, and therefore still long.

Further, because such determinations are based on the combined effect of a large, but unknown, number of cells, such total population determinations do not actually yield a count. In contrast, determinations based on many individual measurements, each associated with an initial single cell, can yield a count.

Finally, because these total population methods are based on the combined effects of many cells, the time required for a determination becomes significantly longer as the number of cells decreases, i.e. as the sample's cell concentration decreases.

Similarly, prior use of flow cytometry for cell growth measurements (see, for example, Hadley et al. in *Instrumental Methods for Rapid Microbiological Analysis*, Nelson (Ed.), VCH, Weinheim, 67-89, 1985) is limited, because conventional use of flow cytometry performs measurements on individual cells, or clumps of cells which naturally adhere, in an aqueous liquid suspension, and therefore does not have the capability to measure colony formation. For this reason, prior use of flow cytometry can only measure total numbers of cells in a volume in order to determine average growth, must also, therefore, involve a careful volume measurement, and is dependent on the signal-to-noise ratio of single cell measurements. This signal-to-noise ratio is less than satisfactory for many measurements (see, for example, Shapiro *Practical Flow Cytometry*, R. Liss, New York, 1985; Hadley et al. in *Instrumental Methods for Rapid Microbiological Analysis*, Nelson (Ed.), VCH, Weinheim, 67-89, 1985).

Likewise, quantitative microscopy and image analysis combined with conventional gel preparations, such as gel slabs, petri dishes and the like, although capable of determining colony formation, is tedious in manual versions, and conventional gel slabs, petri dishes and the like cannot provide physical manipulability or a sufficiently fast characteristic diffusion time within the gel. Thus, cells cannot be rapidly and conveniently exposed to different growth conditions, such as rapid changes in concentrations of nutrients, drugs, hormones, enzymes, antibodies and other chemicals. In addition, conventional gel slabs, petri dishes and the like cannot be readily manipulated physically because of their size, and therefore cannot be readily used for exposure of gel-entrapped cells to in vivo conditions.

Previous studies of gel microdroplets have demonstrated that the suspension of gel microdroplets (GMDs) in a non-aqueous fluid such as mineral oil results in retention of microbial metabolites such as metabolic acids. This in turn allows detection and enumeration of acid-producing microorganisms through the use of colorimetric and fluorescent pH indicators (Weaver et al., Ann. N.Y. Acad. Sci., 434: 363-372, 1984; Williams et al, Ann. N.Y. Acad. Sci. 501: 350-353, 1987). In the previous work, observation of pH changes by optical means such as colorimetry or fluorescence was accomplished using fluorescence microscopy. However, such prior use demonstrated that insignificant chemical communication of highly water soluble compounds, such as metabolic acids, occurs between GMDs even when they are almost contacting. Thus, such GMDs are found to be essentially chemically isolated, and cannot readily have the chemical composition of the aqueous interior of such GMDs altered or modified.

An attribute of these previous GMD methods is that GMDs surrounded by mineral oil (non-aqueous surrounded GMDs) were provide a chemical isolation of GMDs, such that many chemicals are retained within GMDs. This retention within the very small volume of a GMD is the basis for an important class of measurements on individual cells, individual enzyme molecules, microcolonies, and the like. In this previous use of GMDs, chemical retention is achieved by surrounding GMDs by a non-aqueous fluid which has solubility properties which essentially exclude the dissolution of many chemicals, particularly charged or ionic species such as acids. For this reason, such chemicals do not significantly partition into the non-aqueous fluid, and cannot therefore be transported through the non-aqueous fluid by a combination of diffusion and convection.

Although this is highly desirable in order to retain the extracellular products of biologically active entities within a GMD, and also to provide or retain the chemical assay reactants used within a GMD as the basis of an extracellular and/or intracellular assay, the previous use has resulted in an inability to alter the chemical composition, for chemicals insoluble in the non-aqueous fluid, of the GMD interior once the GMDs were created and surrounded by a non-aqueous fluid.

It would, however, be highly desirable to be able to alter the chemical composition of GMD interior fluids at one or more times after the GMDs have been surrounded by a non-aqueous fluid, under controlled conditions, and without the necessity of removing the GMDs from the non-aqueous fluid followed by a re-suspension or re-surrounding of the GMDs by a non-aqueous fluid.

SUMMARY OF THE INVENTION

This invention pertains to a process for chemically manipulating microdroplets which many contain biological entities, wherein microdroplets are surrounded by a non-aqueous fluid, such that both water soluble and ampiphillic species can be delivered to microdroplets surrounded by non-aqueous fluids, and additionally such that the amount of so delivered material can be subsequently determined for each microdroplet. This process includes the use of emulsions containing liquid microdroplets and/or gel microdroplets, which can be cause to collide with, and transfer chemicals to, other microdroplets.

DETAILED DESCRIPTION OF THE INVENTION

Microdroplets

This invention relates to microdroplets, which are very small volume entities comprised of liquid or gel material, and which can contain zero, one or multiple biological entities. More specifically, the term microdroplet (MD) includes both the gel microdroplet (GMD), the liquid microdroplet (LMD), with or without contained biological entities. Thus, unless restricted by specific use of the term "gel microdroplet" or "liquid microdroplet", the term "microdroplet" refers to both gel and liquid microdroplets.

Liquid microdroplets (LMDs) are very small volumes of predominantly liquid material, which can contain solutions, typically aqueous solutions with inorganic and/or organic chemical compounds, and which can additionally contain biological entities. LMDs have volumes which are defined by a boundary comprised of another liquid, such as a non-aqueous fluid, or by a permeability barrier such as a membrane, such that the membrane is capable of retaining biological entities of interest within a LMD, and also capable of passing other biological entities such as molecules.

Although LMDs can be of any shape, LMDs are often approximately spherical because of the tendency of interfacial forces associated with the boundaries of LMDs to round up the deformable LMDs. Other forces, for example hydrodynamic shear associated with stirring a LMD suspension, adhesion to a surface, or gravity, tend to cause departure from a spherical shape. Further, LMDs which contain or occupied by entities whose volume is a large fraction of the LMD volume can result in LMDs which are non-spherical. Thus, for example, a cell surrounded by a thin coating of an aqueous solution, which in turn is surrounded by a non-aqueous fluid, is a LMD. Similarly, a non-biological particle surrounded by a thin coating of an aqueous solution, which in turn is surrounded by a non-aqueous fluid, is also a LMD. If spherical, LMDs have diameters between about $0.2\mu$ to about $1,000\mu$, preferably between about $5\mu$ and about $500\mu$. Generally LMD volumes are between about $8 \times 10^{-15}$ to about $1 \times 10^{-3}$ ml, preferably between about $1 \times 10^{-10}$ to about $1 \times 10^{-4}$ ml.

Liquid microdroplets can be formed by a variety of methods, which are generally well known, and include methods based on breakup of a liquid jet, a spraying process, and by dispersion. For example, an aqueous liquid jet issuing into air can be forced to breakup into liquid microdroplets of nearly uniform volume (see, for example, Kachel and Menke in *Flow Cytometry and Sorting*, Melamed et al (Eds), Wiley, New York, pp. 41-59, 1979), or by spraying an aqueous liquid (see, for example, Rotman, PNAS 47: 1981-1991, 1961). Likewise, the use of dispersion to create emulsions consisting of a non-continuous aqueous phase of aqueous liquid microdroplets is well established (see, for example, Weaver et al., Ann. N.Y. Acad. Sci., 434: 363-372, 1984).

GMDs are very small volume entities which comprise at least one gel region, and which provide a mechanical matrix capable of entraping or surrounding, without necessarily contacting, biological entities such as small multicellular organisms, groups of cells, individual cells, protoplasts, vesicles, spores, organelles, parasites, viruses, nucleic acid molecules, antibody molecules, antigen molecules, and aggregates of molecules. GMDs can consist entirely of gel, in which case containment of biological entities can occur by entrapment of the biological entities by the gel matrix. The general ability of gel matricies to entrap or immobilize biological entities is well known, having been established for a variety of macroscopic gel preparations such as Petri dishes, gel slabs and gel beads (see, for example, *Immobilized Cells and Organelles*, Vols. *I* and *II*, Mattiasson (Ed), CRC, Boca Raton, 1983).

Alternatively, GMDs can consist of a shell of gel matrix material which surrounds at least one aqueous liquid region, in which case containment of biological entites can occur by entrapment of the biological entities by the gel matrix material, or can occur by surrounding biological entities with a shell of gel matrix material, with or without contacting the biological entities.

Further, GMDs can consist of a plurality of regions comprised of gel material and liquid material. Representative configurations of GMDs with a plurality of gel regions include a first gel region entirely surrounded by a second gel region, wherein the second gel region can be comprised of a gel material different from the gel material of the first gel region. Alternatively, a second gel region can be comprise of essentially the same gel material as a first gel region, but the second gel can contain different entities such as entrapped beads and macromolecules, or the second gel can have distinquishable molecules such as fluorescent molecules attached to a constituent of the second gel matrix.

Similarly, GMDs can contain liquid regions which are surrounded by at least one gel region. Representative GMDs with such liquid regions include GMDs which consist of a shell of gel material which surrounds at least one liquid region, such as an aqueous liquid core surrounded by gel. Such GMDs provide a general means for entrapping biological entities without necessarily contacting the biological entities with a gel matrix, as it is only necessary that the gel matrix be impermeable to the surrounded biological entities, and that the gel matrix be sufficiently mechanically strong that such GMDs remain intact during any desired physical manipulation process of GMDs.

Liquid regions and gel regions of GMDs which contain no biological entities are termed nonbiological regions of a GMD.

Although GMDs can be of any shape, GMDs are often approximately spherical, with diameters between about $0.2\mu$ to about $1,000\mu$, preferably between about $5\mu$ and about $500\mu$. Generally GMD volumes are between about $8 \times 10^{-15}$ to about $1 \times 10^{-3}$ ml, preferably between about $1 \times 10^{-10}$ to about $1 \times 10^{-4}$ ml.

The term gel refers to a porous matrix with a high water content. Structures have the ability to entrap biological entities while allowing transport of many molecules within the aqueous medium of the gel matrix. The gel matrix can also contain a chemical solution, typically an aqueous solution with inorganic and/or organic chemical compounds. For example, the gel matrix can contain a physiologic solution or cell growth medium, which is comprised of inorganic ions and molecules and/or organic ions and molecules. Representative natural gel material for creation of GMDs includes kappa-carrageenan, iota-carrageenan, sodium alginate, furcelaran, zein, succinylated zein, succinlylated cellulose, agarose, collagan, fibrin, proteoglycans, elastin, hyaluronic acid and glycoproteins such as fibronectin and laminin, and other naturally occuring extracellular matricies, or the like. Representative synthetic gelable material synthetic water soluble polymers include those formed from vinyl pyrolidone, 2-methyl-5-vinyl pyrridine-methyl acrylate-methacrylic acid copolymer, vinyl alcohol, vinyl pyrridine, vinyl pyrridine-styrene copolymer or the like.

GMDs can be created by a variety of methods, including the subdivision of a macroscopic gel volume, but preferably GMDs are formed or created by converting an aqueous suspension into liquid microdroplets, followed by formation of a gel state from the liquid state of the liquid microdroplets. Liquid microdroplets (LMDs) are very small, deformable volumes of liquid which are surrounded by another distinct fluid, either liquid or gas, or are coated by a membrane material. A general process for creating GMDs involves first creating LMDs, wherein the LMDs are created from a liquid which contains gelable material, such that upon subsequent exposure to gelation conditions, the LMDs are transformed into GMDs. Formation of the gel state can be caused by a variety of well known gelation processes, including temperature changes, ion concentration changes, chemical concentrations, enzyme catalysis, and photopolymerization.

The associated gelation processes may be reversible without hysteresis, reversible with hysteresis or irreversible. In the case of reversible gelation without hysteresis, LMDs can be converted into GMDs, and GMDs can be converted into LMDs, by simply reversing the conditions, for example returning to a temperature which first caused gelation. In the case of reversible gelation with hysteresis, LMDs can be converted into GMDs, and GMDs can be converted into LMDs, by reversing the conditions beyond the conditions needed to cause gelation, for example returning to and then passing a temperature which first caused gelation. In the case of irreversible gelation, the conditions for reversing the gelation process cannot be achieved without creating conditions which are harmful to the biological entities contained in the LMDs or GMDs. One example of irreversible gelation is the formation of GMDs created by photopolymerization.

In one general procedure the liquid suspension is forced through a nozzle or vibrating orifice to form a liquid stream which breaks up, either because of the surface tension of a capillary jet, or by application of a shearing force, to form liquid microdroplets. Subsequently the liquid microdroplets are gelled by exposing the liquid microdroplets to conditions such as a temperature change, or by directing the liquid microdroplets into a solution containing ions which cause gelation. One attribute of the nozzle or vibrating orifice GMD creation method is that most GMDs are about the same size.

Another method for creating GMDs involves the first creation of a macroscopic gel volume, followed by subsequent fragmentation, cutting, disruption, or subdivision of the macroscopic gel volume such that a plurality of very small volume gel fragments or gel particles are created. This general method emphasizes that GMDs need not be spherical, nor even approximately spherical. Instead, it is only necessary that GMDs consist of very small volumes of gel material, with volumes between about $8 \times 10^{-15}$ to about $1 \times 10^{-3}$ ml, preferably between about $1 \times 10^{-10}$ to about $1 \times 10^{-4}$ ml.

It is generally preferred to use a dispersion method for creating GMDs from a liquid suspension, as dispersion methods are simpler, less expensive and generally freeer from clogging problems than are fluid jet methods. The dispersion methods consist of dispersing the liquid suspension into an immiscible liquid such as a heavy alcohol, mineral oil or silicone fluid, by means such as stirring or vortexing the liquid suspension and immiscible liquid together, thereby creating liquid microdroplets surrounded by the immiscible liquid. The liquid microdroplets are gelled during or after the dispersion process by any of a variety of well known gelation processes such as ion exchange or temperature change. Dispersion methods generally create GMDs with a relatively wide range of sizes, for example diameters of about $5\mu$ to $500\mu$.

GMDs can also be formed by the process of fragmenting, cutting, disrupting or otherwise converting a macroscopic volume of gel into very small volume gel particles, such that said GMDs can have irregular shapes. For example, a macroscopic gel slab can be formed in which biological entities such as cells are entrapped at random positions, the gel slab can be cooled to a low temperature, and the gel slab then mechanically impacted so as to fragment the macroscopic gel into pieces, many of which have a very small volume and thereby constitute GMDs.

GMDs can also be formed by processes which cause a gel coating to form around one or more entities, such that the gel entirely surrounds, or essentially surrounds, the entities. For example, by contacting cold cells with a warmer solution of material which contains gel material which gels upon cooling, a coating of gel can be formed around the cells, such that the cells are thereby incorporated into GMDs. In this case the GMDs can be markedly non-spherical, as the gel coating often forms with the shape of the cells. Similarly, non-biological entities such as cell culture microcarrier beads, soil particles and food particles can be incorporated into GMDs by gel-coating processes, such that the resulting GMDs often have shapes which approximate the incorporated non-biological entities.

In those cases wherein GMDs are formed within a non-aqueous fluid, it is often desireable to transfer the GMDs into an aqueous medium, in order to expose biological entities to a variety of conditions relating to growth, metabolism, secretion, transmembrane potential development, membrane integrity and enzyme activity, and also to conditions which favor measurement and isolation of GMDs. An exemplary method for such transfer is gentle agitation if the GMD aqueous interiors contain suitable surfactant agents, including naturally occuring surfactants such as those present in serum.

Composite Gel Microdroplets

Composite GMDs are GMDs which contain more than one distinguishable region of gel material or of liquid material, which gel or liquid materials are non-biological regions which may entrap or surround biological entities, and can be formed by several methods. Thus, a composite GMD is characterized by a plurality of non-biological regions which are further characterized by having at least one non-biological region having a first property surrounding substantially, or entirely, all of at least one non-biological region having a second property Composite GMDs can contain both gel and liquid regions, wherein liquid regions are surrounded by one or more gel regions, so that such composite GMDs must contain at least one gel region. However, in order to be useful for making measurements on biological entities, and for isolating biological entities, at least some composite GMDs contain biological material.

In one general method the aqueous suspending medium is provided with any cells, microbeads or other marker entities or force-coupling entities which are desired to be incorporated or entrapped in a first gel region. First GMDs are then formed from a first gellable material, using any of processes described elsewhere in this disclosure. The first GMDs are then suspended in a medium containing a second gellable material, which second gellable material may be of the same or different composition as the first gellable material. Additionally, the second gelable material can be comprised, partially or entirely, of material which has optical properties such as light scattering, light absorbance or colorimetric, fluorescence, time-delayed fluorescence, phosphorescence and chemiluminescence, so as to distinguish the second gel region from the first gel region. In this way, by using any combination of one or more of such methods, the second gel can provide composite GMDs, in this case of two distinguishable gel regions, termed GMD/GMDs, with desirable optical properties. For example, an optical signal for GMD diameter determination can be obtained from the second gel region while avoiding, with high probability, the contacting of first GMD entrapped cells with the second gel region.

More generally, it is useful to form composite GMDs wherein at least one region contains a first material with a first optical property selected from the group consisting of light scattering, light absorbance or colorimetric, fluorescence, time-delayed fluorescence, phosphorescence and chemiluminescence, and a second region contains a second, optically distinguishable material with optical properties selected from the group consisting of light scattering, light absorbance or colorimetric, fluorescence, time-delayed fluorescence, phosphorescence and chemiluminescence.

Alternatively, marker entities including beads, non-biological particles, crystals, non-aqueous fluid inclusions, viable cells, dead cells, inactive cells, virus, spores, protoplasts, vesicles, stains and dyes can be incorporated into the first gel region or first GMDs, and biological entities such as small multicellular organisms, groups of cells, individual cells, protoplasts, vesicles, spores, organelles, parasites, viruses, nucleic acid molecules, antibody molecules, antigen molecules, and aggregates of molecules can be incorporated into the second gel region in order to provide means for enhanced measurement of composite GMDs. In this case, composite GMDs with at least one gel region containing marker entities selected from the group consisting of beads, non-biological particles, crystals, non-aqueous fluid inclusions, viable cells, dead cells, inactive cells, virus, spores, protoplasts, vesicles, stains and dyes are provided Such composite GMDs are particularly useful in the case that the optical properties of the marker entities are selected from the group consisting of light scattering, light absorbance or colorimetric, fluorescence, time-delayed fluorescence, phosphorescence and chemiluminescence. Composite GMDs can also be characterized by a plurality of non-biological regions which are further characterized by having at least one non-biological region having marker entities surrounding substantially, or entirely, all of at least one non-biological region having a second property.

In order to form composite GMDs, several general processes can be used. One method for producing GMDs having a plurality of non-biological regions, with at least one non-biological region having different properties than at least one other non-biological region, consists of the following general steps: (a) forming GMDs of a first gel using any of the processes described elsewhere in this disclosure, (b) suspending the gel microdroplets in a material capable of forming a second gel, and (c) incorporating gel microdroplets of the first gel into gel microdroplets of the second gel, thereby forming gel microdroplets with distinct non-biological gel regions.

Another general method for producing GMDs having a plurality of non-biological regions, wherein at least one non-biological region has different properties than at least one other non-biological region, consists of the following general steps: (a) forming GMDs, (b) suspending said GMDs in a material capable of forming LMDs, and (c) incorporating GMDs of the first gel into LMDs, thereby forming composite GMDs with distinct non-biological regions, in this case composite GMDs with one or more liquid regions.

Still another general method for producing GMDs having a plurality of non-biological regions, wherein at least one non-biological region has different properties than at least one other non-biological region, involves the following general steps: (a) forming GMDs of a first gel capable of liquification; (b) suspending said GMDs in a material capable of forming a second gel, (c) incorporating GMDs of said first gel into GMDs of said second gel, and (d) liquifying the first gel, thereby forming GMDs with distinct non-biological liquid regions, in this case also with at least one liquid region.

In order to use the gel microdroplets of this invention in processes involving measurement and/or isolation of biological entities, the composite GMDs should be formed from a suspension or solution which contains the appropriate biological entities, and therefore which contains biological material. The composite GMDs of this invention are useful in cases wherein the biological material is composition of biological entities such as small multicellular organisms, groups of cells, individual cells, protoplasts, vesicles, spores, organelles, parasites, viruses, nucleic acid molecules, antibody molecules, antigen molecules, and aggregates of molecules, and is particularly useful in cases wherein the cells are selected from the group consisting of animal cells, plant cells, insect cells, bacterial cells, yeast cells, fungi cells and mold cells, or are selected from the group consisting of normal human cells, human cancer cells, pathogenic bacteria, pathogenic yeast, mycoplasms, parasites, and pathogenic viruses.

Force coupling entities such as beads, non-biological particles, bubbles, and non-aqueous fluid inclusions with force coupling properties selected from the group consisting of ferromagnetic properties, diamagnetic properties, paramagnetic properties, dielectric properties, electrical charge properties, electrophoresis properties, mass density properties, and optical pressure properties can be also incorporated into one or more gel regions, or liquid regions, in order to provide means for physical manipulation of composite GMDs. Thus, it is useful to provide composite GMDs which contain one or more regions with contain force-coupling entities such as beads, non-biological particles, bubbles, and non-aqueous fluid inclusions with force coupling properties Such provision of force-coupling entities allows composite GMDs to be manipulated by applying forces such as electrical force, magnetic force, field flow sedimentation fractionation force, acoustic force, optical pressure force, gravitational force, sedimentation force, non-rotational acceleration force, centrifugal force and centripetal force The invention also includes extension of the basic process to the creation of composite GMDs comprising more than two distinguishable gel regions. For example, composite GMDs which are GMD/GMDs can be used in a GMD formation process to form GMD/GMD/GMDs, that is, composite GMDs with three distinguishable gel regions.

GMDs containing more than one non-biological gel region can be formed, such that composite GMDs are thereby formed, wherein said composite GMDs are comprised of regions of different gel material, and/or of the same gel material but with different entrapped or bound entities. Thus, for example, a GMD which is a composite GMD made from two different gel materials can contain a first inner region which is comprised of a soft, low density gel such as 0.5% agarose, and a second outer region which is comprised of a harder, higher density gel such as 4% agarose. Continuing this illustration, the 0.5% agarose first inner region can support the growth of cells with less compressive force on the cells, while the second outer region can better confine the growing cells.

GMDs containing at least one liquid region can also be formed. An exemplary process for formation of GMDs wherein a gel material region surrounds a liquid region is as follows. A first step comprises using a process to form GMDs from a gel material capable of subsequent liquification, a second step comprises formation of GMDs which consist of a second gel region completely surrounding the first GMDs, such that the second gel material is different from the first gel material, and is capable of remaining a gel under conditions which liquify the first gel, and a third step comprises liquification of the first gel material, with the result that GMDs with a liquid region surrounded by a gel region are thereby formed. A more specific illustration of this process is as follows. The first step comprises forming liquid microdroplets which contain sodium alginate by forcing a suspension of biological entities with sodium aliginate through a vibrating orifice, thereby breaking up the resulting liquid jet which contains both biological entities and sodium alginate, allowing the resulting liquid microdroplets to enter an aqueous medium containing calcium ions, thereby forming calcium alginate GMDs. The second step comprises concentrating the calcium alginate GMDs by means such as filtration and centrifugation, adding molten agarose at about 37° C., following which the calcium alginate GMD suspension is dispersed into mineral oil, and cooling the dispersion, thereby forming agarose GMDs which contain alginate GMDs, The third step comprises exposing said composite GMDs to an aqueous solution containing sodium chloride and essentially zero calcium, such that sodium and calcium ions can be exchanged, and thereby liquifying the calcium alginate within the composite GMDs.

For convenience it is useful to term GMDs comprised of more than one gel and liquid region as composite GMDs, and to use notation such that GMD/LMDs refers to GMDs formed with a first formed region which is liquid and a second formed region which is gel, and GMD/GMD refers to GMDs formed with a first region which is gel and a second formed region which is gel. Thus, in the preceeding more specific illustration, upon completion of the second step GMDs comprising GMD(agarose)/GMDs(calcium alginate) are formed, and upon completion of the third step GMDs comprising GMD(agarose)/LMDs(sodium alginate) are formed.

Measurements of Microdroplets

The term measurement refers to the process of quantifying the amount of a parameter, and includes the term detection, as detection is a coarse measurement which determines whether or not a parameter is greater than or equal to a threshold condition, or is less than a threshold condition. Thus, for example, optical measurement of a microdroplet involves quantifying at least one optical signal associated with a microdroplet. The term quantifying refers to assigning a value to the signal, such that said quantifying has a resolution which allows the parameter to be assigned one of two more than two different values. In contrast, detection refers to measurement wherein the resolution allows the parameter to be assigned to only one of two values, one value which corresponds to subthreshold and therefore non-detection, and the other which corresponds to threshold or suprathreshold and therefore to detection.

Although many useful processes relating to measurement and manipulation of microdroplets, and of any biological entities contained therein, can be carried out without explicit measurements of microdroplet parameters, enhanced measurement and manipulation is often achieved if microdroplet parameters such as microdroplet volume, $V_{MD}$, microdroplet diameter, $D_{MD}$, (if approximately spherical), microdroplet mass and microdroplet mobility are determined.

The volume, $V_{MD}$, of microdroplets can be measured by measuring signals associated with the interface between two fluids which define a MD, or by signals associated with the difference in physical properties of the fluid within a MD and the fluid external to a MD. The physical basis for $V_{MD}$ measurement can be selected from the group consisting of optical, weighing, sedimentation, field flow sedimentation fractionation, acoustic, magnetic, electrical and thermal measurement.

A variety of measurements can be based on a mass density difference between the fluid within a MD and the fluid external to a MD, and include weighing measurement on a microbalance such as a submerged piezoelectric sensor, sedimentation measurement based on an acceleration field such as gravity, rotational acceleration such as centripetal acceleration which is the basis of centrifugation, and/or non-rotational acceleration, which is used to separate MDs on the basis of size and field flow sedimentation fractionation measurement wherein MDs are gently separated according to size (see, for example, Levy and Fox, Biotech. Lab. 6:14–21, 1988). Other methods which are partially based on differences in mass density can also involve differences in other parameters, and include measurements based on acoustic measurement wherein variation in acoustic properties of MDs relative to the surrounding fluid are utilized (see, for example Quate, Physics Today, August 1985, pp. 34–42), magnetic measurement wherein differences in magnetic properties, particularly paramagnetic, diamagnetic and ferromagnetic properties, are utilized, and thermal measurement wherein differences in thermal properties relative to the surrounding fluid are utilized, particularly differences in thermal conductivity, thermal diffusivity and specific heat (see, for example, Bowman et al, Ann. Rev. Biophys. Bioengr. 4:43–80, 1975).

The generally preferred method of measuring $V_{MD}$ involves optical measurements selected from the group consisting of light scattering, light absorbance, fluorescence, phosphoresence and chemiluminescence, as optical measurements are flexible, rapid and non-contacting measurements. Exemplary optical measurements using light scattering can be based on differences in the index of refraction between the aqueous fluid within MDs and a non-aqueous fluid external to a MD, or can be based on differences in light absorbance or colorimetry, phosphoresence or chemiluminescence between the aqueous fluid within MDs and the non-aqueous fluid.

More specifically still, it is preferred to utilize differences in fluorescence of the MD relative to the surrounding fluid, as fluorescence is particularly sensitive. Although both the fluid within a MD and external to MDs can be fluorescent, it is preferred to make measurements wherein either the fluid within the MD, or the non-aqueous fluid external to the MD, have significant fluorescence. Thus, for example, at least one fluorescent molecule type can be incorporated in MDs, such that when surrounded by a non-fluorescent, non-aqueous fluid the volume of a MD can be determined by the total fluorescence intensity associated with the fluorescent molecule, and subject to the further condition that said fluorescent molecule not significantly partition into the surrounding non-aqueous fluid. Still more specifically, a fluorescent molecule such as FITC-dextran can be incorporated into the aqueous medium which comprises the fluid within a MD, and the total fluorescence emission intensity of FITC-dextran measured. Likewise, at least one fluorescent molecule type can be incorporated into the non-aqueous fluid which surrounds MDs, such that the decrease in fluorescence associated with the presence of a non-fluorescent MD provides the basis of $V_{MD}$ measurement (see, for example, Gray et al, Cytometry 3:428–434, 1983).

In addition to the measurement methods which can be used with microdroplets generally, GMDs containing one or more marker entities can also be measured by measuring signals associated with at least one marker entity which is incorporated into a gel matrix of at least one GMD, wherein said marker entity is capable of measurement. In the case of GMDs which exist prior to measurement, marker entities can be incorporated into the pre-existing GMDs prior to measurement. Alternatively, marker entities can be incorporated into GMDs by supplying marker entities in the aqueous medium from which GMDs are formed, thereby incorporating marker entities into GMDs during the formation of GMDs The volume, $V_{GMD}$, of a GMD can be determined by first measuring the marker entities contained within a GMD, followed by analysis of the amount of marker entities in at least one gel microdroplet so as to determine the size or volume of said gel microdroplet. Statistical analysis can be applied to one or more types of measurements relating to GMD properties, and/or to one or more types of measurements relating to biological enities. It is preferred to combine measurement of biological entities with measurement of $V_{GMD}$, so that statistical analysis relating to the number of biological entities in GMDs can be used, and for such combined measurements biological entities are incorporated into GMDs prior to measurement of the GMDs based on marker entities.

Exemplary types of marker entities include beads, non-biological particles, crystals, nonaqueous fluid inclusions, viable cells, dead cells, inactive cells, virus, spores, protoplasts, vesicles, stains and dyes. Non-biological particles include particles comprised of inorganic material such as silica, of organic material such as charcoal or carbon, and of combinations of inorganic and organic material wherein the organic material can be of biological or non-biological origin. Such marker entities allow a variety of measurement to be made, including optical, weighing, sedimentation, field flow sedimentation fractionation, acoustic, magnetic, electrical and thermal measurements However, it is preferred to measure GMDs optically by using marker entities which can be measured by using light scattering, light absorbance or colorimetric, fluorescence, time-delayed fluorescence, phosphorescence and chemiluminescence.

In cases wherein the presence of marker entities does not adversely affect biological entities contained within GMDs, or the ability of gel material to form a gel matrix, gellable material can be pretreated so as to attach at least one type of marker entity to at least one gellable material prior to formation of GMDs, thereby resulting in formation of GMDs having enhanced measurement properties. Thus, for example, pretreatment of gelable material by chemically attaching marker entities comprising fluorescent molecules renders the GMDs by measurable by fluorescence. Alternatively, GMDs can be first formed, and marker entities subsequently introduced. For example, macromolecules such as dextrans can be labeled with a fluorescein derivative, agarose GMDs exposed to said macromolecules, whereupon the fluorescent dextran can diffuse into the agrose, and then be subsequently precipitated or complexed, such that the dextran is essentially trapped within the gel, and the GMDs are thereby provided with marker entities in the form of fluorescent labeled dextran.

In some preparations of GMDs, a significant number of biological entities, such as cells, can either remain free in suspension, or can escape from some types of GMDs during vigorous physical manipulation. This results in suspensions which contain both cells trapped within GMDs and free cells, wherein the term free cells refers to cells free in suspension and not contained within MDs. This occurrance is usually undesirable. Thus it is highly desirable to provide measurement means for distinguishing free cells from cells contained within GMDs. For example, the formation of microcolonies within GMDs provides a general method for determining growth of biological entities, particularly cells, and allows direct determination of plating efficiency following an incubation by quantitatively comparing the number of microcolonies to single cells. However, if significant free cells can sometimes occur in suspension, and free cells usually cannot be distinguished from cells contained within GMDs, so that significant error can result. In such cases it is preferred to measure at least one type of marker entity contained within GMDs, such that it is possible, by measurement of both marker entities and biological entities, to determine that there is a high probability that the biological entity is associated with a gel microdroplet. In other cases the measurement of marker entities can comprise detection, wherein the detection of one or more GMDs allows measurements of biological entities to be associated, with high probability, with the containment of said biological entities within GMDs. For example, non-growing individual cells within GMDs can be distinguished from individual cells which are free in suspension.

Often it is also desirable, in order to enhance subsequent statistical analysis, to determine $V_{GMD}$ for a GMD associated with a measured biological entity. In this case the measured parameter used for a marker entity type is selected to be distinguishable from measured parameters which relate to measurements of biological entities. For example, biological entities which contain double stranded nucleic acids can be measured by using well known staining protocols utilizing propidium iodide (PI), and measuring the Red Fluorescence associated with PI, while marker entities such as entrapped microbeads, or covalently attached fluorescein, with Green Fluorescence provide the basis for measurement of $V_{GMD}$, as the magnitude of the Green Fluorescence signal is proportional to $V_{GMD}$. The combined measurements of $V_{GMD}$ and bilogical entities further provide the basis for determining the frequency-of-occupation of GMDs by biological entities, and thereby enhance statistical analysis methods such as those provided by using Poisson statistics or modified Poisson statistics.

Marker entities can be selected with a variety of physical properties which result in enhancement of GMD measurement upon incorporation of said marker entities into GMDs. Useful physical properties which provide the basis for measurement of marker entities include optical properties, mass density properties, acoustic properties, magnetic properties, electrical properties and thermal properties. Because of their speed, specificity, non-perturbing nature and non-contacting nature, it is preferred to use optical measurement means, including flow cytometry apparatus, flow-through-microfluorimetry apparatus, optical particle analyzers apparatus, fluorescence microscopy apparatus, light microscopy apparatus, image analysis apparatus and video recording apparatus to measure marker entities. More specifically, in the case of flow cytometry, it is useful to measure optical pulses such as maximum pulse magnitude, pulse time integral and pulse duration, all of which are well known (see, for example, Shapiro, *Practical Flow Cytometry*, A. R. Liss, New York, 1985).

The marker entities can also be measured using well known electrical measurements, particularly electrical resistance measurements, electrical measurements which provide the basis of particle analysis, such as the electrical resistance based particle measurements (see, for example, Kachel in *Flow Cytometry and Sorting*, Melamed et al (Eds), Wiley, New York, pp. 61-104), and dielectric property measurement (see, for example, Harris et al, Enzyme Microb. Technol. 9: 181-186, 1987). These electrical measurements are well known and generally desirable because of the relative ease and relative low cost of making such electrical measurements.

Statistical Analysis of Measurements

The use of microdroplets generally provides means for making a large number of individual measurements relating to a biological sample. This is in constrast to most established measurement methods, as most established measurement methods are responsive to the total effect on measured parameters by biological entities contained in a sample. Thus, although useful measurements can be made using small numbers of microdroplets, in general, the use of large numbers of individual microdroplet measurements provides the basis for making significantly improved measurements on biological entities of a sample. Although significant measurement information can be obtained without explicitly carrying out statistical analysis of large numbers of microdroplet measurements, significant improvement in measurements is achieved by applying statistical analysis to microdroplet measurements.

Measurements on microdroplets are often made wherein more than one parameter is measured. For example, it is generally preferred to use optical measurements, particularly fluorescence measurements, in which case simultaneous measurements such as Green Fluorescence measurement and Red Fluorescence measurement are often made. In the exemplary case of measurements relating to a mixed biological population, a Green Fluorescence labeled antibody can be used to measure the amount of biological material associated with a first type of biological entity, and a Red Fluorescence labeled antibody can be used to measure the amount of biological material associated with a second type of biological entity. Following an incubation the magnitude of the Green Fluorescence and Red Fluorescence signals can be used to determine the amount of growth of each type of biological entity, such that the frequency-of-occurrence distribution of the Green and Red Fluorescence signals can be obtained, and then statistically analyzed to determine the variation in growth, and the variation in lag time, for both types of biological entities. In this exemplary case, however, it is not necessary to use statistical analysis in combination with microdroplet volume measurement, but only with the Green and Red Fluorescence measurements. Thus, although statistical analysis of microdroplet measurements is generally useful, statistical analysis does not necessarily involve the use of microdroplet volume measurements, nor does statistical analysis necessarily relate to occupation of microdroplets. Instead, statistical analysis can relate to the frequency-of-occurence of measurements relating to the biological entities themselves.

Individual and Multiple Microdroplet Occupation

In many cases it is useful to determine, at least approximately, the statistical distribution of occupation of microdroplets by biological entities. As used herein, the term "occupation" refers to the presence of initial biological entities, that is, those biological entities present shortly after formation of microdroplets, and before any incubation is used. Thus, for example, in the representative case wherein biological entities are cells, microdroplets can have a high probability of zero occupation, individual occupation, or of multiple occupation. As used herein, zero occupation or unoccupied refers to the case wherein a microdroplet contains zero initial cell, individual occupation refers to the case wherein a microdroplet contains one initial cell, and multiple occupation refers to the case wherein a microdroplet contains at least two initial cells. Following an incubation, growth may occur and result in increases in size and number of cells, such that an individually occupied microdroplet subsequently contains progeny cells of the initial single cell, and is nevertheless termed an individually occupied MD, and a multiply occupied microdroplet subsequently contains progeny cells of the initial multiple cells, and is nevertheless termed a multiply occupied MD.

In the general case wherein a microdroplet contains at least two types of biological entities, the term occupation can be used separately with each type of biological entity. Thus, for example, in the case of a mixed biological population comprised of two types of cells, type A and type B, a microdroplet can initially contain, prior to any incubation, one A cell and several B cells. In this case the microdroplet is termed individually occupied by type A cells and multiply occupied by type B cells, and the same designation is also used subsequent to any incubation which results in growth. That is, continuing this example, if incubation subsequently leads to A cell progeny, the microdrop is still deemed individually occupied by type A cells. This terminology is straightforwardly extended to all types of biological entities.

Analysis Using Poisson Statistical Methods

It is often preferred to make measurements on microdroplets that are individually occupied, so that the measurements can be interpreted as measurements relating to one biological entity. In order to form microdroplets which have a significant fraction of microdroplets with individual occupation, it is generally useful to estimate the distribution of occupation for different size microdroplets. Many methods for forming microdroplets, in which biological entities are incorporated into microdroplets, are random, or well approximated by randomness, such that statistical analysis involving one or more MD parameters, such as diameter or volume, is useful for determining the probability of occupation of different size microdroplets.

As a result, it is generally useful to determine the size of microdroplets that have a high probability of having zero, individual or multiple occupation, so that the probability of having less than two initial biological entities, and of having at least two initial biological entities, in microdroplets of different size or volume ranges can be estimated. If the concentration of the suspended biological entities is known approximately, or can be estimated, then the suspension can be diluted so as to provide an average, known number of biological entities in liquid microdroplets of a particular size or volume being made. A mathematical formula or equation which describes the relation between the average number of biological entities and liquid microdroplet volume is the Poisson probability distribution, $P(n,\bar{n})$, (see, for example, Gosset, Biometrika, 5: 351–360, 1907; Weaver et al., Ann. N.Y. Acad. Sci., 434: 363–372, 1984; Weaver, Biotech. and Bioengr. Symp. 17, 185–195, 1986; Williams et al., Ann. N.Y. Acad. Sci., 501: 350–353, 1987), which in its application to microdroplets gives the probability, $P(n,\bar{n})$, of finding a particular number, n, of initial biological entities in microdroplet volume $V_{MD}$ if the average number of initial biological entities found in the volume $V_{MD}$ is $\bar{n}$. More specifically $$P(n,n) = \frac{(\bar{n})^n e^{-\bar{n}}}{n!} \quad (1)$$

A mathematical relation governing $\bar{n}$ is $\bar{n} = \rho V_{MD}$, where $\rho$ is the concentration of the biological entities in the suspension which was converted into liquid microdroplets, and the term "average occupation" is defined to be $\bar{n}$, and refers to the average or mean number of initial biological entities present before any incubation. For a sample with randomly distributed biological entities, such as a well-stirred sample, the probability of finding particular numbers of biological entities is described by the Poisson formula. Thus, the probabilty of having zero initial biological entities or being unoccupied is $P(0,\bar{n})$, the probability of having one biological entity or being individually occupied is $P(1,\bar{n})$, the probability of having two biological entities is $P(2,\bar{n})$, and so on. Of particular interest to some applications of GMDs is the situation wherein a LMD is initially occupied by more than one entity, that is, multiply occupied. The probability of multiple occupation is $P(>1,\bar{n})$, and, because the sum of all possible probabilities equals one, the probability of initial multiple occupation is as follows:

$$P(>1,\bar{n}) = 1 - P(0,\bar{n}) - P(1,\bar{n}) \qquad (2)$$

Generally, the transition from LMDs to GMDs does not involve significant changes in volume, i.e. $V_{MD} = V_{LMD} \approx V_{GMD}$ in most cases. In such cases the Poisson probability can be used interchangeably with either LMDs or GMDs. If the volume change is significant, a volume scaling factor, $f_{vol}$, is used according to $V_{GMD} = f_{vol} V_{LMD}$, such that there is a common relation between the volumes of all GMDs and the LMDs from which they were created. This scaling factor, $f_{vol}$, is generally a well known macroscopic property of gel materials.

In the process of creating MDs, a sample volume, $V_S$, is mixed with a volume of additional material, $V_{Add}$. In the case of GMD formation, the volume $V_{Add}$ usually contains gellable material which forms the gel matrix of the subsequent GMDs. The corresponding dilution by a factor $f_D$ is as follows:

$$f_D = \frac{V_S}{V_S + V_{Add}} \qquad (3)$$

and is straightforwardly computed following measurement of both $V_S$ and $V_G$. The diluted biological entity concentration, $\rho$, is therefore related to the sample biological entity concentration, $\rho_S$ by the following:

$$\rho_S = \frac{\rho}{f_D} \qquad (4)$$

where $\rho$ is the biological entity concentration used in the Poisson equation.

In the case of biological entities which naturally aggregate, in the Poisson equation, the mathematical parameters $n$, $\bar{n}$ and $\rho_S$ refer to the particular number of aggregates, the average number of aggregates and the concentration of aggregates, respectively. Thus, for biological entities which naturally aggregate as colony forming units (CFU), in the Poisson equation $n$, $\bar{n}$ and $\rho_s$ refer to the particular number of CFUs, the average number of CFUs and the concentration of CFUs, respectively.

In some cases it is desirable to make measurements on more than one MD at a time, and thereby to make measurements on clusters or groups of MDs which are associated with individual MDs. In this case the Poisson statistics formula is applied with the change that $V_{MD}$ is replaced by $V_{group}$, wherein $V_{group}$ is the sum of the individual MD volumes in the group.

In some cases, such as those wherein the volume of n biological entities, $nV_{BE}$, within a MD is a significant fraction of the volume of a MD, $V_{MD}$, it is useful to employ a modified form of the Poisson formula. An example of a modified Poisson function is given in equation (5).

$$P(n,\bar{n}) \approx \frac{\bar{n}^n e^{-\bar{n}}}{n!} \text{ with } \bar{n} = \rho(V_{MD} - nV_{BE}) \qquad (5)$$

in which the "available volume" $= V_{MD} - nV_{BE}$ replaces $V_{MD}$, which provides a better description of the frequency of occupation for cases wherein $V_{BE}$ is a significant fraction of $V_{MD}$. This approximate equation uses the definition that the volume of a MD containing n cells is defined to be the volume of the gel material plus $nV_{BE}$, and is consistent with the inability of two or more nominally idential biological entities initially occupying a MD of volume less than $2V_{BE}$. In the case that non-identical biological entities are initially present, the quantity $nV_{BE}$ is replaced by $V_{total,BE}$, the total volume of the biological entities.

Another approximate, modified version of the Poisson function is is most readily presented in terms of a separate mathematical expression for each of the probabilities, $P(0,\bar{n})$, $P(1,\bar{n})$, $P(2,\bar{n})$, etc. The first two expressions are $$P(0,\bar{n}) \approx 1 \text{ if } V_{MD} < V_{BE} \text{ and } e^{(-\bar{n}-\rho V_{BE})} \text{ if } V_{MD} \geq V_{BE} \qquad (6a)$$

$$P(1,\bar{n}) \approx 0 \text{ if } V_{MD} < V_{BD}, (1 - e^{(-\bar{n}-\rho V_{BE})}) \text{ if } V_{BE} < V_{MD} \leq 8V_{BE} \qquad (6b)$$

These modified Poisson forumulae or equations agree with equation (1) in the mathematical limit that $V_{BE}$ approaches zero, but provide better descriptions results in cases wherein the volume of the initial biological entities within a MD is a significant fraction of $V_{MD}$.

Further, other extensions or modifications of statistical analysis can be used to analyze cases wherein the analyzed MDs have a significant range of volumes. The basic concept underlying such analysis is that each size range of MDs separately obeys the same probability equation, specifically Poisson statistics or modified Poisson statistics.

The preferred embodiment of the invention initially uses conventional Poisson statistics for all cases, but then uses either the version given by equation (5) or by equations (6a), (6b), (6c) and extensions thereof, if occupations of small volume MDs differ significantly from those obtained from large volume MDs in the same preparation made from the same sample. It is also possible to utilize any other extension of Poisson statistics which provides descriptions of the probability of occupation in the case that $V_{BE}$ is a significant fraction of $V_{MD}$. Depending on the relative size, shape and means for forming MDs, other version of modified Poisson statistics formulae may be utilized.

The most conceptually simple measurements relate to measurements which simultaneously measure one MD. Such measurements can be made using a variety of measurement apparatus based on optical, weighing, sedimentation, field flow sedimentation fractionation, acoustic, magnetic, electrical and thermal means, but preferably optical means in the form of flow cytometry apparatus, flow-through-microfluorimetry apparatus, optical particle analyzers apparatus, fluorescence microscopy apparatus, light microscopy apparatus, image analysis apparatus and video recording apparatus. Electrical means can include dielectric property measurement apparatus or a particle analyzer based on electrical resistance measurement As before, microdroplet measurements are made in such measurement apparatus by operating the apparatus in a mode wherein there is a high probability that less than two MDs are simultaneously within the measurement volume of the apparatus. Thus, in the exemplary case of flow cytometry, the instrument is operated in a mode wherein there is a high probability that less than two MDs are simultaneously in the focal volume of the optical illumination region. Further, in the exemplary case of microscopy, the instrument is operated in a mode wherein there is a high probability that less than two MDs are simultaneously in the field view used in a measurement. A general advantage relating to making measurements on less than two MDs simultaneously relates to simplicity of interpretation, as measurements can be interpreted in terms of measurements on individual biological entities or their progeny.

Somewhat more conceptually complex measurements relate to measurements which simultaneously measure at least two MDs, wherein a plurality of MDs is termed herein as a group or cluster of MDs. As described elsewhere in the present disclosure, such measurements can be made using a variety of measurement apparatus based on optical, weighing, sedimentation, field flow sedimentation fractionation, acoustic, magnetic, electrical and thermal means, but preferably optical means in the form of flow cytometry apparatus, flow-through-microfluorimetry apparatus, optical particle analyzers apparatus, fluorescence microscopy apparatus, light microscopy apparatus, image analysis apparatus and video recording apparatus, or electrical means in the form of dielectric property measurement apparatus or a particle analyzer based on electrical resistance measurement Microdroplet measurements are made in such measurement apparatus by operating the apparatus in a mode wherein there is a high probability that at least two MDs are simultaneously within the measurement volume of the apparatus. Thus, in the exemplary case of flow cytometry, the instrument is operated in a mode wherein there is a high probability that less than two MDs are simultaneously in the focal volume of the optical illumination region. Further, in the exemplary case of microscopy, the instrument is operated in a mode wherein there is a high probability that less than two MDs are simultaneously in the field view used in a measurement. Advantages relating to making measurements on at least two MDs simultaneously include larger measurement throughput rates of MDs, for example in cases wherein many MDs are unoccupied, and reduced technical complexity of measurement apparatus because of generally larger measurement region volume.

The most conceptually simple use of microdroplets involves MDs with individual occupation, as measurements of individually occupied MDs can be readily related to measurements of biological material associated with an initial individual biological entity. For example, measurement of an individually occupied MD provides the basis for analysis and interpretation of growth of an initial biological entity.

A more conceptually complex use of microdroplets involves microdroplets with multiple occupation. Multiple occupation may be selected for a variety of reasons, such as allowing more biological entities to be measured for the same number of MDs, or to provide biological entities initially at a higher concentration within MDs. The multiply-occupied MD measurement itself, however, is essentially equivalent to the measurement of multiple MDs, that is, measurement of groups or clusters of two or more MDs. As used herein, measurement of multiple MDs consists of either the making or combining of measurement of two or more MDs. For example, the multiple measurement of five MDs consists either of making a simultaneous measurement on five MDs, or on making measurements of any subgroup of the five MDs followed by summing the subgroup measurements to obtain the multiple MD measurement.

Even though measurement results cannot be as readily interpreted in terms of individual biological entities, advantages of making measurements on multiply occupied MDs include making measurements on biological entities at a higher rate in comparision to individually occupied MDs, and to lower costs associated with requiring less material and time to make measurements. In addition, important information can often be obtained which cannot be readily obtained from nonmicrodroplet measurement methods. Specifically, measurement of multiply occupied MDs provides the basis for analysis and interpretation of growth of initial biological entities, wherein said growth is the average growth associated with the occupation of the MD. Similarly, secretion by one hyperactive biological entity, or its progeny, can be measured in the presence of other, poorly secreting biological entities. For example, in the case that MDs with average occupation by three cells is measured, the measurement can still reflect any significant variability which is present in the cells, as the measurement of average property of three cells can be significantly affected by one unusual cell, thereby determining that an unusual cell is present. Measurements can be useful with multiply occupied MDs containing 2 to about $10^3$ initial biological entities, but are preferably used with multiply occupied MDs containing 2 to about 10 initial biological entities.

For example, consider the illustrative case wherein according to Poisson statistics the mean or average occupation is three, so that $\bar{n}=3$, the mathematical Poisson probability formula predicts the distribution of particular occupation values, n, given in the table below.

| n | $P(n, \bar{n} = 3)$ | n | $P(n, \bar{n} = 3)$ |
|---|---|---|---|
| 0 | 0.050 | 5 | 0.101 |
| 1 | 0.149 | 6 | 0.050 |
| 2 | 0.224 | 7 | 0.020 |
| 3 | 0.224 | 8 | 0.008 |
| 4 | 0.168 | | |

In this illustration, there is a low probability (0.05) of having unoccupied MDs, a high probability (0.95) of having occupied MDs. The probability of individual occupation is 0.15 so the probability of multiple occupation is 0.80. Thus, 80% of MDs initially contain at least two biological entities. However, even in this example for which the mean occupation is high, the multiply occupied MDs have a peaked distribution of occupation, such that there are equal, maximum probabilities of 0.224 of having either 2 or 3 initial biological entities, and rapidly decreasing probabilities of having 4 or more initial biological entities. As a result, the probability, $P(>7,\bar{n})$ of having more than seven (7) initial biological entities is $$P(>7,\bar{n}) = 1 - \sum_{n=0}^{n=7} \frac{(n)^{\bar{n}} e^{-\bar{n}}}{n!} \quad (7)$$

which is low, about 0.006. In summary for this illustration, the use of multiply occupied MDs with $\bar{n}=3$ results in multiply occupied MDs for which only n=2 to 7 have significant probability.

Thus, for example, in contrast to relatively macroscopic preparations such as test tubes, cell culture flasks and microtiter wells which are often used with thousands of biological entities such as cells, and which therefore usually result in small effect on the total population by one biological entitiy, in the present example it is highly probable that a single biological entity will have seven or fewer other biological entities within the same MD. For this reason, an unusual property of such a single biological entity, such as significantly greater secretion rate, can have a large fractional effect, and thereby be measured, although non-optimally, in the presence of the other biological entities within the same MD.

It is also possible to straightforwardly carry out measurements on multiple MDs, that is groups or clusters of MDs, wherein one or more of the MDs are multiply occupied. Such a process of measuring multiple multiply occupied MDs is equivalent to measuring one large MD of same total volume as the sum of the MD volumes of the MDs which comprise the group or cluster of MDs, and can have the advantage of providing still larger throughput measurement rates while still retaining other advantages of MDS, such as the generally short characteristic diffusion time, $t_D$.

Manipulation of Microdroplets Surrounded by Non-Aqueous Fluids

It is generally desirable to provide means for applying forces on MDs, so as to provide means for manipulating MDs, such as changing or maintaining the locations of MDs, so that external influence from physical, chemical and biological sources can be provided, for purposes such as measurement, incubation and isolation. It is useful to distinguish two classes of processes for applying forces which accomplish changing or maintaining positions of MDs. These two classes are forces which depend on MDs being surrounded by a non-aqueous fluid, and forces which depend on MD force coupling entities, or intrinsic properties of MDs, which are surrounded either by a non-aqueous fluid or an aqueous fluid.

In the case of MDs which are GMDs, following GMD creation in a non-aqueous fluid, the GMDs are left suspended, allowed to settle, or captured on a grid or filter, while surrounded by the non-aqueous fluid, such that the GMDs can now be manipulated through the use of physiochemical interactions that exploit differences in properties of the aqueous GMD interior fluid and the GMD-surrounding non-aqueous fluid.

Alternatively, if GMDs are created in an aqueous fluid, the GMDs can be transfered to a non-aqueous fluid, wherein the GMDs are manipulated by the use of physiochemical interactions that exploit differences in properties of the aqueous GMD interior fluid and the GMD-surrounding non-aqueous fluid.

In this invention MDs can be surrounded by non-aqueous fluids in order to provide a non-aqueous environment which surrounds or suspends microdroplets. Representative suitable non-aqueous fluids include liquid hydrocarbons, mineral oils, silicone fluids, ferrofluids, and heavy alcohols. This invention further involves physical manipulation of microdroplets surrounded by a non-aqueous fluid so as to change the position of such microdroplets by applying one or more physical forces, which are due to differences in properties of the MDs and the surrounding non-aqueous fluid.

More particularly, such forces can be applied by selecting forces selected from the group consisting of electrical force, magnetic force, field flow sedimentation fractionation force, acoustic force, optical pressure force, gravitational force, sedimentation force, non-rotational acceleration force, centrifugal force and centripetal force. While most of these forces are extremely well known in general, the term optical pressure force as applied to particles the size of MDs is more recent (see, for example, Ashkin et al, Nature 330: 769-771, 1987). In the process of this invention it is preferred to utilize electrical force selected from the group consisting of electrophoresis force, iontophoresis force, electrokinetic force, dielectric force and coulombic force, which are well known forces which can be applied to entities with electrical charge and/or dielectric properties which differ from the dielectric properties of the medium surrounding the entities.

A particular process involving such electrical force is carried out using the following steps: (a) providing a non-aqueous fluid environment, (b) providing a plurality of charged electrodes within said non-aqueous fluid environment wherein at least two electrodes are of opposite polarity, (c) injecting an electically charged material capable of forming electrically charged microdroplets into the non-aqueous fluid; and (d) moving one or more charged microdroplets by means of an electrical force associated with potential differences which are applied between two or more electrodes, such that it is possible to produce microdroplets within a non-aqueous fluid, to introduce microdroplets into a non-aqueous fluid, to move microdroplets within a non-aqueous fluid, and to remove microdroplets from a non-aqueous fluid. Alternatively, MDs formed by any means and surrounded by a low electrical conductivity medium can be charged by contacting the MDs with a charged electrode.

It is thus possible to use such forces to manipulate the position of MDs with respect to measurement entities such as light emitting diodes, lasers, electrical capacitors, electrical inductors, electrical resistors, thermistors, thermocouples, fiber optics, photodiodes, phototransistors, photocells, piezoelectric sensors, specific ion electrodes, oxygen electrodes, carbon dioxide electrodes, pH electrodes and electrodes allowing dielectric property measurement. More specifically, such physical force is utilized to move MDs into proximity to such measurement entities, to maintain MDs in proximity to such measurement entities, and to remove MDs away from such measurement entities.

In addition to physically manipulating MDs with respect to one or more such measurement entities, in the process of this invention physical force is also utilized to move MDs which are located within measurement apparatus such as light measuring instruments, light microscopes, fluorescence microscopes, luminometers, fluorometers, photometers, time-resolved fluorometers, image analysis systems, colorimeters, spectrofluorimeters, particle counters, particle measuring systems, photoacoustic instruments, acoustic absorption instruments, acoustic microscopes, dielectric spectrometers, electrical impedance measuring instruments, calorimeters, thermal property measurement instruments and piezoelectric mass loading instruments.

Similarly, the process of this invention can be used to cause MDs to come into contact with other MDs, or for contacted MDs to be separated. The former is particularly useful to enhancing collisions and coalescence of LMDs, while the latter is particularly useful for separating weakly adhering GMDs.

Likewise, the process of applying one or more forces to MDs surrounded by a non-aqueous fluid can be used to physical force is used to provide physical manipulations of microdroplets selected from the group consisting of moving microdroplets into proximity of, maintaining microdroplets in the proximity of, and removing microdroplets away from so that such MDs are exposed to external sources of physical influence, or exposed to sources of chemical influence. Such MDs surrounded by a non-aqueous fluid can be exposed to any physical source of external influence, including sources of heat, electric fields, magnetic fields, electromagnetic radiation, optical radiation, ionizing radiation, acoustic radiation and acceleration. Suitable sources of chemical influence include those which produce, release, modify or consume chemical compounds which are capable of dissolving in both the surrounding non-aqueos fluid and the aqueous interior of such MDs.

Finally, all of such manipulations are of particular utility in the case that at least one of the microdroplets contains at least one biological entity such as small multicellular organisms, groups of cells, individual cells, protoplasts, vesicles, spores, organelles, parasites, viruses, nucleic acid molecules, antibody molecules, antigen molecules, and aggregates of molecules.

In another embodiment of this invention it is possible to chemically manipulate MDs which are surrounded by a non-aqueous fluid. The present embodiment relates to the chemical manipulation of MD interior fluid composition while the MDs are maintained surrounded by a non-aqueous fluid. This invention thereby allows biological entities within non-aqueous fluid surrounded MDs to be exposed to water soluble agents and compounds, and allows water soluble chemical reagents to be added to such MDs, thereby significantly extending the ability to carry out biological and chemical assays and tests using MDs.

More specifically, this invention consists of a process for delivering water soluble, entities and water insoluble entities, through an intervening non-aqueous fluid into MDs, with means for subeqently determining the quantitiy of material so delivered. The major types of delivery processes involve:

(1) Introduction of LMDs or GMDs which contain (a) water soluble species to be delivered, and (b) water soluble optical indicator species which allow subsequent measurement of the amount water soluble material delivered to each MD, or (2) Dissolution of ampiphillic species (soluble in both aqueous and non-aqueous fluids) into the surrounding non-aqueous fluid, such that stirring and diffusion within the non-aqueous fluid provides essentially homogeneous distribution of the ampiphillic species in the non-aqueous fluid, which in turn allows partitioning of such species into the non-aquoeus surrounded MDs.

A more complete disclosure of these processes is provided in the following sections. If not already surrounded by a non-aqueous fluid, it is first necessary to surround the microdroplets with an environment which comprises a non-aqueous fluid The general process of this embodiment involves chemically manipulating MDs, which are surrounded by a non-aqueous fluid, by altering the concentration of at least one chemical compound within the MDs by altering the composition of the surrounding non-aqueous fluid. A general means for accomplishing such chemical manipulation involves the dissolution of at least one chemical compound in the non-aqueous fluid, such that the chemical can partition into the aqueous interior of the MDs, and thereby cause a change in the chemical composition of the aqueous interior of the MDs.

Alternatively, the composition of the non-aqueous fluid can be altered by adding MDs to the non-aqueous fluid, such that the MDs contain at least one water soluble chemical compound. A general procedure for accomplishing such chemical manipulation comprises the steps of: (a) dissolving at least one chemical compound in a first non-aqueous fluid, (b) contacting said first non-aqueous fluid with a second non-aqueous fluid, said second non-aqueous fluid surrounding at least one microdroplet, said chemical compound being soluble in the first non-aqueous fluid, in the second non-aqueous fluid, and in aqueous medium, and (c) allowing time for partitioning of said chemical compound from the first non-aqueous fluid into the second non-aqueous fluid, and subsequently into at least one microdroplet.

Often it is desirable to use the additional step of mixing in order to shorten the time needed for partitioning of chemicals compounds into microdroplets from the non-aqueous phase, as such mixing reduces or eliminates the large concentration gradients that arise upon dissolving a chemical compound in the non-aqueous fluid Another general process for accomplishing chemical manipulation of MDs surrounded by a non-aqueous fluid involves providing additional MDs in the non-aqueous fluid, such that the additional MDs contain the chemicals which are to be supplied to the original MDs. Such additional MDs can be provided in the form of an emulsion, by contacting the emulsion to the non-aqueous fluid, such that the non-continuous phase of the emulsion comprises the additional MDs, and such that the continuous phase of the emulsion is comprised of the same, or a miscible, non-aqueous fluid as that which originally surrounds the original MDs. Often it is desirable to improve this process by mixing the emulsion and non-aqueous fluid after the emulsion and non-aqueous fluid are contacted.

Another version of this process involves the use of an emulsion wherein the non-continuous phase of the emulsion consists of GMDs, rather than LMDs.

Although in some applications it is not necessary to know how much of a chemical compound is delivered to MDs, in some applications, for example the delivery of an antimicrobial, it is important to know the amount or concentration of the chemical following the chemical manipulation of the MDs. In order to provide means for such measurement, it is useful to provide at least one tracer compound with measurable properties which is delivered to MDs by the same means as the chemical compounds, such that MDs can then be measured for the amount of tracer compound In addition, a measurable tracer can also be provided in the non-continuous phase of an emulsion contacted with the non-aqueous fluid, as this provides a measure of the total amount of the emulsion so contacted with the non-aqueous fluid Overall, the use of such tracers is important in that measurement of the amount of at least one tracer compound allows determination of the amount of at least one other chemical compound which has been delivered to the MDs.

In order to measure such tracers, the tracer compounds are selected to have measureable properties selected from the group consisting of optical properties, mass density properties, acoustic properties, magnetic properties, electrical properties and thermal properties. Of these, it is preferred to utilize tracers with optical properties such as light scattering, light absorbance or colorimetric, fluorescence, time-delayed fluorescence, phosphorescence and chemiluminescence A particularly useful optical property is fluorescence, which can be provided by using tracer compounds such as fluorescein, rhodamine, coumarin, lucifer yellow, phycoerythrins and their chemical derivatives In order to enhance collisions and contact between the non-continuous phase of the emulsion and the MDs, it is possible to electrically charge the non-continuous phase of the emulsion, for example, by using means similar or identical to those for forming MDs with electrical charge by forcing an aqueous medium from an electrically conducting needle into an agitated non-aqueous fluid while a large electrical potential difference is maintained between the needle at a large area electrode on the outside of the non-aqueous fluid container In conducting of the process of this invention, it is useful to alter the chemical concentration within MDs by delivering chemical compounds having properties such as antiviral activity, enzyme inhibitory activity, antimicrobial activity, antifungal activity, cytotoxic activity, and chemotherapeutic activity It is further useful to deliver compounds which are reactants for one or more enzyme catalyzed reactions, and it is particularly useful to utilize reactants such as fluorescein-di-$\beta$-D-galactopyranoside, resorufin-$\beta$-D-galactopyranoside, fluorescein diacetate, carboxyfluorescein diacetate, fluorescein isothiocyanate diacetate, fluorescein digalactoside, 4-methyl umbelliferone butyrate, 4-methyl umbelliferone phosphate, 1-napthol phosphate, 2-napthol phosphate, 3-$\mu$-methyl-fluorescein phosphate, napthol AS phosphates, diacetyl 2-7-dichloro fluorescein, homovanillic acid, homovanillic acid+rhodamine lead, nicotinamide adenine dinucleotide (NAD) and resazurin

Microdroplet Incubation

Incubation consists of providing conditions for a time interval such that biochemical and biological reactions have an opportunity to occur. Incubation includes biochemical reactions and processes relating to replication of genetic material, synthesis of biological material, degredation of biological material, metabolism, secretion, uptake, ligand binding, aggregation based on specific binding such as occurs in antibody-antigen reactions, the reactions which comprise the formation and/or growth of molecular complexes and aggrgates, and the complex reactions which comprise growth of virus, cells and small mutlicellular entities. Thus, during incubation biological entities have an opportunity to increase in size and/or number, and also to exhibit biochemical activity. Further, by altering the concentration of one or more compounds exhibiting properties such as antiviral activity, enzyme inhibitory activity, antimicrobial activity, antifungal activity, cytotoxic activity, and chemotherapeutic activity compounds, before, during or after an incubation, such compounds can be allowed to affect biological entities.

The term biological entity refers to small biological structures which are capable of being incorporated into liquid microdroplets and/or gel microdroplets, and includes small multicellular organisms, groups of cells, individual cells, protoplasts, vesicles, spores, organelles, parasites, viruses, nucleic acid molecules, antibody molecules, antigen molecules, and aggregates of molecules. Small multicellular organisms include fertilized eggs, blastomers, embryos, small nematodes and small helminths, which are of a size that can be incorporated into GMDs. Groups of cells include colony forming units, or CFUs, of naturally aggregating cells, and also microcolonies that result from growth of cells following one or more incubations. General types of cells of interest include animal cells, plant cells, insect cells, bacterial cells, yeast cells, fungi cells and mold cells. Organelles include mitochondria, choroplasts, ribosomes and lysosomes. Protoplasts include those made from cells with cell walls by enzymatic digestion and other wall removing processes, or by mutants which lack cell wall synthesis ability. Virus includes those such as Herpes simplex, cytomegalo virus, Epstein-Barr virus, adenoviruses, influenza A or B virus, parinfluenza 1,2 or 3 virus, mumps virus, measles virus, coronavirus, poliovirus, coxsackie A and B virus, echovirus, rhinovirus and hepatitis A and B virus, and human immunodeficiency virus or HIV. Nucleic acids include both DNA and RNA. Antibody molecules include IgA, IgG, and IgM obtained from animals such as human, mouse, rat, goat, dog, pig and monkeys. Antigen molecules include large antigenic molecules with multiple distinct epitopes and/or overlapping epitopes, and small molecules such as haptens. Aggregates of molecules include immunoprecipitates, antigens which have bound one or more antibodies, with or without labels, hybridized nucleic acids and non-covalently bound complexes of two or more molecules. Although many of the examples of use of biological entities with microdroplets are described in terms of cells, particularly cells such as animal cells, plant cells, insect cells, bacterial cells, yeast cells, fungi cells and mold cells, the broader group is intended. Further, as used here, biological entity also refers to any of these previously mentioned entities which have been reacted with one or more lableing molecules, stains, dyes or with one or more intervening molecules.

Capturing Molecules at Binding Sites in GMDs

This invention relates to GMDs which contain one or more provided binding sites within the GMDs. Such GMDs are used to capture molecules within the GMDs at the provided binding sites. Such GMDs, and processes carried out with such GMDs, allow important measurements, manipulations and isolations to be carried out. The process of capturing molecules consists of: (a) incorporating specific sites and biological entities into GMDs, (b) allowing molecules released from biological entities in GMDs to move by diffusion, convection or drift within the GMDs, such that some molecules encounter the binding sites and are bound at such sites, thereby capturing molecules released from biological entities at binding sites within GMDs.

Molecules captured within GMDs by this process can then be measured, in order to determine properties or behavior of biological entities contained within the GMDs. Useful measurement means for measuring the captured molecules include optical, weighing, sedimentation, field flow sedimentation fractionation, acoustic, magnetic, electrical and thermal means It is preferred to use optical measurements such as measurements based on light scattering, light absorbance or colorimetric, fluorescence, time-delayed fluorescence, phosphorescence and chemiluminescence.

If the captured molecules have one or more measureable optical properties, the captured molecules can be measured by measuring a naturally occuring optical signal associated with the captured molecules, including optical signals such as light scattering, light absorbance or colorimetric, fluorescence, time-delayed fluorescence, phosphorescence and chemiluminescence.

In the practice of this invention it is often useful to provide one or more incubations, in order to allow different conditions to effect the production and/or release of molecules from the biological entities. For example, it is useful to provide one or more incubations in order to allow molecules released by secretion from non-growing cells to accumulate in sufficient numbers at binding sites that measurement of the captured molecules is more readily accomplished. Likewise, it is often useful to provide one or more incubations which provide growth conditions for biological entities, particularly cells, in order that cells can increase in size and/or number, such that the total ability of the biological entities within a GMD to produce and secrete molecules within a GMD is increased, thereby resulting in capture of more molecules at binding sites within such GMDs.

Gel microdroplets can also be physically isolated on the basis of measurement of the captured molecules, followed by release, if desired, of biological entities from the isolated GMDs by processes such as dissolution of GMDs, mechanical disruption of GMDs and outgrowth by the biological entities, such that biological entities contained within the isolated GMDs are physically isolated based on the measurement of captured molecules. Examples of physical isolation include removing GMDs from a suspension and placing the GMDs in another suspension, sorting the GMDs by using a flow cytometer/cell sorter, identifying GMDs by microscopy and utilizing micromanipulation to remove the GMDs, and using optical pressure to move GMDs to a known location. Following physical isolation of GMDs, biological entities contained within the GMDs can be released from GMDs by processes such as dissolution of the gel matrix, mechanical disruption of the gel matrix and outgrowth from the gel matrix by at least one biological entity In some uses of this invention, a measurement of captured molecules is omitted, and instead forces which interact with one or more captured molecules are used to physically isolate GMDs, and thereby the biological entities contained therein. This can be followed by release of biological entities from the isolated GMDs by processes such as dissolution of GMDs, mechanical disruption of GMDs and outgrowth by the biological entities, such that biological entities contained within the isolated GMDs are physically isolated based on physical forces interacting with the captured molecules.

In cases wherein it is desired to measure captured molecules, the captured molecules do not necessarily have properties which allow satisfactory measurement. In this case it is often possible to provide a subsequent step which comprises exposing GMDs to one or more labeling molecules which have measurable properties and also are capable of binding to, and thereby labeling, the captured molecules. Following the process of exposing GMDs to one or more labeling molecules, the labeling molecules are then measured, using either physical or chemical means. Examples of labeling molecules include antibodies, antigens, nucleic acids, lectins, receptors, enzyme inhibitors, and protein A, all with measurable labels.

In the practice of this invention it is preferred to use optical measurements to measure labeling molecules which have bound to the captured molecules, including optical measurements of labeling molecules with labels which can be measured by light scattering, light absorbance or colorimetric, fluorescence, time-delayed fluorescence, phosphorescence and chemiluminescence. Exemplary labeling molecules which are labeled with such labels include antibodies, antigens, nucleic acids, lectins, receptors, enzyme inhibitors, and protein A, all with measurable labels.

Physical isolation of GMDs, and the biological entities contained within the GMDs, can be accomplished by using labeling molecules having a label capable of coupling with a physical force, such that following exposure of GMDs to labeling molecules, the GMDs with labeled captured molecules are manipulated by at least one physical force in order to physically isolate such GMDs. In this embodiment it is preferred to provide and use magnetic labels It is often desirable to expose GMDs containing captured molecules to one or more intervening molecules before exposing, or simultaneously with exposing the GMDs to labeling molecules. This is accomplished by: (a) supplying at least one intervening molecule type and (b) supplying labeling molecules, such that intervening molecules bind to captured molecules and labeling molecules bind to intervening molecules. Examples of intervening molecules include antibodies, antigens, nucleic acids, lectins, protein A and avidin. For use as an intervening molecule, it is preferred to use unlabeled antibodies obtained from an animal species different than that from which a labled antibody is obtained as a labeling molecule. For example, a mouse antibody to a captured molecule can be used as an intervening molecule, and a fluorescence-labeled goat anti-mouse antibody can be used as a labeling molecule for the intervening molecule, such that a first exposure to this intervening molecule, and a second or simultaneous exposure to the labeling molecule results in the ability to measure the captured molecules.

If desired, an intervening molecule can also have one or more labels, such that the binding of both intervening molecules and labeling molecules increases the amount of label associated with captured molecules, thereby enhancing the measurement of captured molecules It is useful to practice this invention using the biological entities including cells, spores, protoplasts, vesicles and small multicellular organisms, and it is preferred to use small multicellular organisms and cells such as animal cells, plant cells, insect cells, bacterial cells, yeast cells, fungi cells and mold cells.

In cases in which biological entities do not secrete molecules of interest, or secrete molecules at a less than desired rate, it is useful to cause biological entities to release cells by providing one or more external stimuli. A general method for providing stimulus to cells, vesicles, protoplasts and small multicellular organisms involves the application of an electromagnetic stimulus which results in electroporation (see, for example, Sowers and Lieber, FEBS Lett. 205: 179-184, 1986)

Determination of Biological Growth

Prior use of GMDs has been based on determination of cell activity, more particularly metabolic activity, of one or more biological entities contained within the very small volume of a cell-occupied GMD. A general feature of such activity based determinations is that GMDs are provided with a permeability barrier, in the form of a coating, or by suspending the GMDs in mineral oil (see Weaver et al., Ann N.Y. Acad. Sci., 434: 363-372, 1984; Weaver, Biotech. and Bioengr. Symp. 17, 185-195, 1986; Williams et al., Ann. N.Y. Acad. Sci., 501: 350-353, 1987). Activity based determinations using GMDs are based on the extracellular accumulation of cell products within the very small volumes of GMDs, and the use of chemical indicators or chemical assays in combination with changes in the extracellular environment within a very small volume. The determinations are fundamentally based on a time integration of the production rate for cell products which are released into the extracellular environment, and which are retained within the very small volume of a GMD. Further details concerning the production of GMDs may be found in U.S. Pat. Nos. 4,399,219, 4,401,755 and 4,643,968, each of Weaver, the teachings of which are incorporated herein by reference.

In such prior use of GMDs cell growth itself has not been determined, but instead the accumulated effect of cell activity, which is due to both to the activity per cell and to cell number, was the basis of the determinations. Thus, for example, an increase in cell products within a GMD with a permeability barrier could be due either the presence of one highly active cell, such as a single yeast cell, or could be due to an initial bacterium which rapidly grows to form a microcolony of several cells, which microcolony has activity several times that of an individual bacterium. In the first example, a single yeast cell, without the occurrence of growth, is the basis of a determination, while in the second example, the determination occurs primarily because of the increase in cell biological material, and corresponding increased activity, due to growth. As demonstrated by this illustration, for different cell types the same change in extracellular chemical concentration due to activity can occur with or without growth, depending on the relative individual cell activity and the relative cell growth rate, so that for this reason the prior use of GMDs does not provide a general means for determining cell growth. Further, although a significant advantage of the prior use of GMDs is that cell growth is not necessarily the basis of determinations, generally the type of activity must be known. For example, although a great many microorganisms produce significant amounts of acids, allowing GMD determinations based on extracellular pH changes within the very small volume of a GMD with a permeability barrier, the production of significant acid is not a universal property of cells. For this reason, prior use of GMDs has required knowledge of the type of biochemical activity exhibited by a cell, whereas, in contrast, the present invention is much more general.

For the above reasons, neither the previous methods of others, nor the previous use of GMDs to detect cells based on metabolic product retention, actually provides a rapid determination of cell growth, a fundamental process in which biological entities increase in biological material and/or in number. In contrast, the present invention provides a general means for biological entity growth determination, wherein entrapment of initial and progeny biological entities within MDs, preferably GMDs surrounded by an aqueus fluid or medium, is combined with measurement of the biological material within MDs, and which, because of the very small size MDs, allows incubation conditions and analysis conditions to be changed rapidly because of the small diffusion times within MDs. In the case of MDs which are GMDs, this invention also allows optical measurements to be made with small optical path lengths within a gel matrix. This reduces optical measurement error associated with light scattering, light absorbtion or autofluorescence in a gel matrix.

In the case of cells which naturally aggregrate and adhere to each other in small numbers, the present invention determines the growth of colony forming units (CFUs).

In the general practice of this invention MDs are formed by any of the previously described means, such that biological entities such as small multicellular organisms, groups of cells, individual cells, protoplasts, vesicles, spores, organelles, parasites, viruses, nucleic acid molecules, antibody molecules, antigen molecules, and aggregates of molecules are incorporated into MDs. The resulting MDs can contain biological entities such that MDs of different sizes have a high probability of being mostly unoccupied, individually occupied or multiply occupied. Measurement of biological material is then accomplished by making measurements on the MDs, either individually or in small groups, such that measurements responsive to biological material are made. Biological material consists of the constituative molecules and structures found in biological entities such as small multicellular organisms, groups of cells, individual cells, protoplasts, vesicles, spores, organelles, parasites, viruses, nucleic acid molecules, antibody molecules, antigen molecules, and aggregates of molecules. Thus, examples of biological material include proteins, nucleic acids, phospholipids, polysaccharides, enzymes, antibodies, cell receptors and other well-known biological molecules.

Measurement of biological material can be accomplished by using measurements based on optical, weighing, sedimentation, field flow sedimentation fractionation, acoustic, magnetic, electrical and thermal means. Such measurements can be based on properties such as optical properties, mass density properties, acoustic properties, magnetic properties, electrical properties and thermal properties. It is preferred to utilize measurements based on optical properties such as are measureable utilizing light scattering, light absorbance or colorimetric, fluorescence, time-delayed fluorescence, phosphorescence and chemiluminescence. Thus, useful measurement apparatus includes flow cytometry apparatus, flow-through-microfluorimetry apparatus, optical particle analyzers apparatus, fluorescence microscopy apparatus, light microscopy apparatus, image analysis apparatus and video recording apparatus.

In some cases naturally occurring optical properties of the biological material of biological entities can be used to measure the biological material, as this provides a naturally occurring optical signal Examples of such naturally occurring signals are light scattering, light absorbance or colorimetric, fluorescence, time-delayed fluorescence, phosphorescence and chemiluminescence. However, in order to enhance the measurement of biological material in GMDs it is often useful to employ staining protocols which utilize stains such as stain indicative of biological composition, stain indicative of enzyme activity, and stain indicative of cell membrane integrity, as such stains are responsive to the amount, activity and/or state of biological material. More specifically, it is often desirable to use stains in the general catagories of fluorescent stains, light absorbance stains and light scattering stains, and more specifically stains such as nucleic acids stains, protein stains, lipid stains, cell membrane stains, cell wall stains, stains responsive to enzyme activity, stains responsive to transmembrane potentials and cell surface receptor stains. Still other useful types of stains include transmembrane potential stains, membrane exclusion stains and intracellular enzyme activity responsive stains.

It is generally preferred to use fluorescent stains such as propidium iodide, ethidium bromide, FITC (fluorescein isothiocyante), fluorescein diacetate, carboxyfluorescein diacetate and FITC diacetate. Many other suitable fluorescent stains for biological material are well known (see, for example, Haugland *Handbook of Fluorescent Probes and Research Chemicals*, Molecular Probes, Junction City).

In the general practice of this invention it is preferred to make measurements of MDs involving predominantly measurements of individual or single MDs However, measurements can also be made simultaneously on groups of two or more MDs. Likewise, it is preferred to make measurements on MDs consisting predominantly of microdroplets with a high probability of containing less than two biological entities prior to incubation, but measurements can also be made on microdroplets specimens consisting predominantly of microdroplets with a high probability of containing at least two biological entities prior to incubation.

Although it is useful to measure the amount of biological material in GMDs without requiring measurement of the volumes of individual GMDs, or of groups of GMDs, it is often useful to measure such GMD volumes. This data can be used to provide the basis for further analysis or interpretation of the biological material measurements. For example, measurement of such GMD volumes provides the basis for determining the volume of a sample which was contained in the measured GMDs, as the measured GMD volumes can be summed to yield the total volume analyzed, with correction for dilution if needed.

Additionally, it is often useful to analyze the measurement of MD volumes, or volumes of groups of MDs, with statistical formulae which relate the occupation of MDs to MD volume and the average concentration in the suspension or solution from which MDs were formed. More specifically, it is often useful to analyze MDs and measurements of the amount of biological material, such that measurement of the biological material provides a basis for classifying each MD, or group of MDs, as being unoccupied or occupied. It is then useful to further analyze the MDs and measurements by using Poisson statistics formulae and modified Poisson statistics formulae.

If control analysis is desired, one or more specimens of MDs are measured without incubating. Other MDs are then exposed to conditions for which growth determination is sought, and incubated for one or a plurality of incubation periods, and some or all of the MDs then measured, individually or in groups, for the amount of biological material present in the individual MDs or in the groups of MDs. The results of such MD measurements are interpreted as the amount of change in biological material during the control or incubation periods, and such change in biological material is attributed to the amount of growth which occured during the incubation period.

Following such measurement of the change in the amount of biological material, one or more forces can be applied such that MDs containing biological material with a first change in the amount of biological material are isolated from MDs not containing biological entities with the first change in the amount of biological material In the preferred embodiment of the invention, MDs are created with a wide range of sizes, such that some range of sizes has a high probability of containing zero or one initial biological entities. One subpopulation of MDs is measured without incubation in order to provide a control, and one or more other subpopulations of MDs are incubated under desired conditions and then measured individually for the relative amount of biological material in each MD.

It is useful to separately consider the case wherein the volume, $V_{MD}$, of each MD is known or measured, and it is also known that the sample contains biological entities at approximately known concentration, $\rho_S$, so that following concentration or dilution of the sample, and after addition of gelable material, the resulting concentration, $\rho$, is known, and is the suspension from which MDs are made.

A preferred embodiment of this invention involves formation of MDs which are GMDs, followed by suspending these GMDs in an aqueous or non-aqueous medium. Following one or more incubations of these GMDs the growth of individual biological entities into microcolonies of two or more biological entities can occur. In the case in which GMDs are surrounded by a non-aqueous fluid, the GMDs are transfered from the non-aqueous fluid into an aqueous fluid. A staining procedure for biological entity biological material is then used to provide the basis of one or more optical measurements, such that the magnitudes of the optical signals provides a determination of the biological material present in each measured GMD.

In a representative case of the general invention, wherein MDs are GMDs suspended in an aqueous medium, the biological entities are cells such as animal cells, plant cells, insect cells, bacterial cells, yeast cells, fungi cells and mold cells. A fluorescent dye is used to stain nucleic acids, the fluorescence associated with the dye is measured in the GMDs, preferably in individual GMDs, and the frequencey-of-occurrence of a certain magnitude of a fluorescence signal can be displayed as a function of the magnitude of fluorescence signal. This type of plot is generally termed a histogram. Such analysis shows that incubated GMDs with growing cells produce histograms with fluorescence peaks that occur at larger magnitude fluorescence. It is often convenient to plot the frequency-of-occurrence versus logarithm fluorescence, because cells growing in the exponential phase then exhibit a linear or proportional increase in the average log fluorescence as a function of time. It is found that such plots generally exhibit peaks with increasingly larger average fluorescence for GMDs incubated for longer times. The area of such peaks provides a measure of the average growth of cells, and thereby the average growth rate. It has been found that such GMD based average growth rate determinations compare favorably with conventional, total population methods. The present invention also provides a measure of the variation in growth rate, or growth rate distribution, which is reflected in the variation of fluorescence within the fluorescence peaks which is greater than the variation or instrumental error in the fluorescence measurement apparatus itself, and which is not determined by conventional methods This invention can also be used to determine the lag time in growth of biological entities. This lag time is the delay in achieving an exponential growth rate following exposure to changed conditions. Such determinations are made by comparing the magnitude of the change in the amount of biological material in GMDs incubated under particular changed conditions to the change in the amount of biological material in other GMDs incubated under control conditions. Such lag time determinations utilize the growth rate determinations described elsewhere in this disclosure.

Further, in some cases such analysis reveals a fluorescence peak at approximately the location of the initial or non-incubated peak, whose peak area provides a measure of non-growing cells for the incubation conditions used. If such conditions correspond to conditions which ordinarily support growth of the cell type, then the ratio of the number of GMDs with growing cells to the number of both growing and non-growing cells can be interpreted as the cloning or plating efficiency in GMDs for these conditions. Conventional rapid growth measurements based on the combined effects of many cells do not provide direct determination of non-growing cells, but instead can only provide a determination based on the combined effects of growing and non-growing cells, and the relative numbers of growing and non-growing cells is not known a priori.

In addition to measuring the biological material consisting of the total amount of one or more types of biological material, it is often useful to supply chemical compounds in order to utilize reactions such as degrading reactions of stainable biological material and blocking reactions of stainable biological material, so that enhanced measurement is achieved. For example, in the case of GMDs in an aqueous medium wherein it is useful to measure total stainable nucleic acid to provide a measurement of growth, it is also possible, for biological entities that contain DNA which is replicated, to provide a RNA degredation process such as exposing the GMDs to RNAase, which degrades the RNA while leaving the DNA, such that subsquent exposure to a necleic acid stain allows DNA to be measured in GMDs. Such measurement of DNA then provides the basis for determining replication of biological entities.

The process of the present invention can provide determinations of biological entity growth which are based on measurement of biological material within MDs which initially had a high probability of having zero or one biological entity. This biological entity growth determination process is rapid, often requiring about one average generation or doubling time. However, the process can also be advantageously carried out using more generations or doublings, in order to allow possibly unstable cells to cease growing, and/or in order to utilize less sensitive and less expensive optical measurement apparatus.

Although the previous illustration describes a preferred embodiment, in which there is a high probability of some MDs, of some size or volume range, $V_{MD}$, being unoccupied or individually occupied it is also possible to make growth measurements using MDs in a size range, relative to the biological entity suspension concentration, $p$, for which there is a moderate or high probability of multiple occupation. In this case the measurement of optical signals from individual MDs relates to the total biological material within each MD, and therefore correponds to an average growth determination, wherein the average is over the small number of biological entities initially present for each MD size. For example, if the biological entity concentration, $p$, just prior to MD creation results in $\bar{n}=3$ biological entities in MDs of size $V_{MD}$, then the average growth determination has a high probability of corresponding to the average growth behavior of 3 biological entities, and can reveal some aspects of growth heterogeneity or variability which cannot be determined by conventional methods which are based on the combined effects of many, typically $10^4$ or more, biological entities.

Alternatively, in a related embodiment, MDs with a high probability of inital occupation by zero or one biological entities can be measured in small groups rather than individually. This can be advantageous, for example, in flow cytometer measurement of GMDs suspended in an anqueous medium, wherein measurement conditions allow several GMDs to be present transiently in the optically measured region, and thereby allows a higher rate of GMD analysis. Likewise, this can be advantageous in measurement using microscopy, of MDs suspended in, or surrounded by, a nonaqueous fluid, wherein measurement conditions allow several MDs to be present in the measurement field of view, and thereby allows a higher rate of MD analysis. In this embodiment, measurements on groups of MDs incubated for two or more incubation periods are compared, and the differences in optical signals from the groups of MDs are interpreted as resulting from differences in biological entity material within the groups of MDs. These differences are interpreted as arising from biological entity growth within the groups of MDs. For example, measurements on groups of incubated MDs are compared to measurements on groups of non-incubated MDs, such that differences in optical signals from the incubated groups of MDs and non-incubated groups of MDs are interpreted as resulting from differences in biological entity material. These differences are further interpreted as resulting from biological entity growth during the incubation period. This embodiment is related to the previous embodiment, in that the biological material optical signal corresponding to several initial biological entities forms the basis of the measurement, and therefore provides the average growth determination as having a high probability of corresponding to the average growth behavior of several biological entities. This method can thus reveal some aspects of growth heterogeneity or variability which cannot be determined by conventional methods which are based on the combined effects of many, typically $10^4$ or more, biological entities.

In the present invention, after creation, the MDs are placed in desired conditions for determining growth. Typically MDs can be suspended in aqueous or non-aqueous media which provide a wide range of different chemical compositions, and at different pH, temperature, partial pressures of oxygen and carbon dioxide, etc. This allows biological growth under a wide range of conditions to be determined. As an alternative to suspension, MDs can be held stationary by allowing MDs to sediment under the influence of an applied force such as gravitational or centripetal force. In the case of GMDs, the GMDs can be temporarily trapped against a porous mesh or filter by a perfusing flow, which provides a supply of growth medium past the trapped GMDs.

The transport of chemicals within MDs is generally governed by diffusion. Thus, in the case of MDs surrounded by a non-aqueous fluid, the supply and removal of chemicals to biological entities within the MDs is governed by the partioning of chemicals between the non-aqueous fluid and the interior aqueous fluid of the MDs, and is further governed by diffusion within the MDs. Because of the relatively small size of MDs, the characteristic diffusion time, $\tau_{diffusion} = x^2/D$ can be short, as x is the characteristic distance over which diffusive transport occurs, and $\gamma_{MD} \approx x$. This yields $\tau_{diffusion}$ from about 4 min to about $5 \times 10^{-6}$ sec for MDs with diameters of $1000\mu$ to $0.2\mu$, and from about 1 min to about $6 \times 10^{-3}$ sec for MDs with diameters of $500\mu$ to $5\mu$ for small molecules with $D \approx 10^{-5}$ cm$^2$ sec$^{-1}$. This value is approximately representative of the size molecule which can readily partition and diffuse between the non-aqueous fluid surrounding a MD and the interior aqueous fluid of the MD. As a result, if the kinetics of partioning and transport within the non-aqueous fluid are not limiting, the characteristic diffusion time, $\tau_D$, governs changes, and can be short. Thus, the concentration of some types of molecules, specifically those with significant solubility in both the non-aqueous fluid and the aqueous interior medium can be changed rapidly in such MDs.

Similarly, the supply and removal of chemicals to biological entities within GMDs surrounded by an aqueous medium is governed primarily by diffusion, and by partitioning between the external aqueous medium surrounding the GMDs and the aqueous medium within the GMDs, because the gel matrix effectively clamps viscous flow, that is, increases resistance to viscous flow. The partitioning between the external aqueous medium and the GMD interior medium is often non-selective, because many gels used to form GMDs do not exclude, absolutely or partially, most chemicals of interest. In some cases, however, gel materials can have charge or size exclusion properties so as to partically or absolutly exclude some molecules from the interiors of GMDs.

Further, because of the relatively small size of GMDs compared to conventional, more macroscopic gel preparations, the characteristic diffusion time, $\tau_{diffusion} = x^2/D$, where x is a characteristic dimension such as the thickness of a macroscopic gel slab and D is the diffusion constant within the aqueous liquid within the gel, can range from shorter to much shorter than for conventional gel preparations. Depending on the type of biological entity used, and the chemicals of interest, $\tau_{diffusion}$ can have a wide range of values, as can be seen by using $\gamma_{GMD} \approx x$, which gives $\tau_{diffusion}$ from about 4 min to about $5 \times 10^{-6}$ sec for GMDs with diameters of $1000\mu$ to $0.2\mu$, and from about 1 min to about $6 \times 10^{-3}$ sec for GMDs with diameters of $500\mu$ to $5\mu$ for small molecules with $D \approx 10^{-5}$ cm$^2$ sec$^{-1}$, and about a factor of 100 longer for macromolecules with $D \approx 10^{-7}$ cm$^2$ sec$^{-1}$. As a result, even the concentration of macromolecules can be changed rapidly in GMDs with diameters of about $200\mu$ or less, as the corresponding diffusion time is about 1 hour, a value much smaller than the doubling time of typical mammalian cells. This value can be changed even more rapidly in the smaller GMDs which can be used with smaller microorganisms such as bacteria and yeast, which microorganisms have shorter doubling times. As a further example, $20\mu$ GMDs used with rapidly growing bacteria for which the doubling time, $t_2$, is typically about 20 min, have an appropriately short $\tau_{diffusion}$ of about 0.1 sec for small molecules and about 10 sec for macromolecules.

After one or more incubation periods the MDs are measured, preferably by optical means. Other measurement means include methods sensitive to mass density, such as weighing, sedimentation, and sedimentation field flow fractionation, and additional methods based on acoustic, magnetic, electrical and thermal properties of MDs containing different amounts of biological material. Sedimentation field flow fractionation force can be provided by simultaneously utilizing a hydrodynamic force and a sedimentation force (see, for example, Levy and Fox, Biotech. Lab. 6:14–21, 1988). Acoustic measurements utilize sound absorbtion and reflection of biological material, as is utilized in acoustic microscopy (see, for example Quate, Physics Today, August 1985, pp. 34–42). Magnetic measurement utilizes diamagnetic, paramagnetic and, occasionally, ferromagnetic properties of biological material. Thermal measurement utilizes thermal conductivity, thermal diffusivity and specific heat properties of biological material (see, for example, Bowman et al, Ann. Rev. Biophys. Bioengr. 4: 43–80, 1975). Electrical measurement utilizes electrical resistance and dielectric properties of biological material, such that measurement of the dielectric properties at various frequencies can provide measurement of biological material (see, for example, Kell in *Biosensors: Fundamentals and Applications*, Turner et al (Eds), Oxford University Press, Oxford, pp. 427–468; Harris et al, Enzyme Microb. Technol. 9: 181–186, 1987). The measurement of electrical resistance of biological entities such as cells is well known to provide a means for measuring cell size, and is the basis for particle analyzers such as the Coulter Counter (see, for example, Kachel in *Flow Cytometry and Sorting*, Melamed et al (Eds), Wiley, New York, pp. 61–104). In the present invention, the preferred electrical measurement is utilized with GMDs suspended in or surrounded by an aqueous medium, is preferably used with biological entities with bilayer membranes. These entities include small multicellular organisms, cells, vesicles and protoplasts. The electrical measurement is based first on a rapid diffusional exchange of medium within a GMD from a defined electrical resistance medium such as physiological saline, followed by a second step of passing GMDs though a particle analyzer such as a Coulter Counter. The gel matrix of such a GMD provides negligible electrical resistance compared to such biological entities, thereby allowing measurement of the amount of biological material associated with cells contained in GMDs.

It is presently preferred to utilize optical measurements in order to measure biological material contained within MDs. Well known general optical measurements sensitive to biological material include light scattering, light absorbance or colorimetric, fluorescence, time-delayed fluorescence, phosphorescence and chemiluminescence.

Biological material contained within MDs can in some cases be adequately measured utilizing naturally occuring optical properties of the biological material. Thus, for example, fluorescence of the biological material, light absorbance by the biological material, and light scattering by the biological material can sometimes be used.

Prior to optical measurements, however, it is often preferred to expose MDs, particularly GMDs surrounded by an aqueous medium, to one or more staining processes. These processes can be general (e.g. nucleic acid stains) or they can be specialized (e.g. fluoresence-labeled antibodies), depending on the type of biological entity and the purpose of the biological entity growth determination. In the case of MDs surrounded by a non-aqueous fluid, stains can be introduced through the surrounding non-aqueous fluid by dissolving the stains in the non-aqueous fluid, or by supplying the stains in the non-continuous phase of an emulsion which is contacted with the non-aqueous fluid. In the case of GMDs surrounded by an aqueous fluid or medium, stains can be introduced through the surrounding aqueous fluid by dissolving the stains in the aqueous fluid.

In the general case wherein growth analysis without further use of the biological entities is desired, any biological entity staining process, including those which kill biological entities, can be used. In the case wherein further analysis or use of viable biological entities is desired, biological entity staining which allows biological entity survival is used. As is well known in the art, there are biological material stains for nucleic acids stains, protein stains, lipid stains, cell membrane stains, cell wall stains, stains responsive to enzyme activity, stains responsive to transmembrane potentials and cell surface receptor stains.

Following exposure of the MDs to suitable stains, the MDs are individually measured, or the MDs are measured in small groups, provided that the probability of finding more than one biological entity-containing MD in the group is low. In the exemplary case of biological entities stained by fluorescent compounds, optical analysis such as digital fluorescence microscopy or flow cytometry is used to measure individual MDs, using a wavelength band sufficiently different from that used for any detection of measurement of MD properties. This method allows simultaneous, or serial, measurement of MD properties and of biological entities with said MD. The associated fluorescence signals are acquired and measured, with correction for spectral overlap if necessary, by conventional means.

The relatively small size of MDs results in the possibility of more flexible analysis. For example, conventional flow cytometers have flow biological entity channel diameters of several hundred microns, which prohibits the use of flow cytometry with conventional macroscopic gel preparations, but which readily allows the use of MDs in the size range from somewhat less than the flow biological entity channel size and smaller.

The magnitude of the optical signal due to the biological entity stain in each MD, or group of measured MDs, is compared to the optical signal of individual biological entities, whether or not such individual biological entities are entrapped in MDs, thereby providing a calibration. Comparison of the MD optical signal magnitude to that of individual biological entities provides the basis for determination of growth of individual biological entities, for which the growth determination can often be made within one generation time, but without a need for significant prior culture to obtain large numbers of biological entities.

By making a large number of such individual biological entity growth determinations, the distribution of growth rate, distribution of lag time, and the plating efficiency can be automatically determined by computer calculation. Manual or visual inspection and scoring of MDs can also be used, but is relatively labor intensive and therefore more prone to error, so that the preferred processes are those conducted using automated measurement means.

Determination of Effects of Compounds on Biological Entities

The present invention further provides means for determining important properties of chemical compounds and agents as said properties relate to the effects of said compounds on biological entities, particularly the growth of biological entities. Alternatively, this invention also provides means for determining important properties of biological entities, particularly cells, relating to the susceptibility or resistance of the biological entities to the effects of compounds or agents on behavior of the biological entities. This is especially useful for determining the effects of compounds on the growth behavior of biological entities which can be determined by measuring the amount of biological material associated with biological entities contained in MDs. A general process for determining the effect of compounds on the growth of biological entities comprises the steps of: (a) exposing MDs to at least one compound, said compound being such that its effect on the growth of said biological entities is to be determined, and (b) measuring biological material within at least one MD In some applications of this invention, MDs can be supplied which already contain biological entities, but in other applications in is necessary to first incorporate biological entities into gel microdroplets. The incorporation can be accomplished using any of previously described processes for the formation of MDs.

As used in this invention, the term specimen of microdroplets encompasses both specimens of LMDs and specimens of GMDs, and refers to a subset of the MDs formed from a sample. Thus, for example, if a sample is processed so as to lead to the formation of about $10^5$ MDs, these MDs can be divided into ten approximately equal specimens of MDs wherein each specimen of MDs contains about $10^4$ MDs.

The effect of compounds or agents on biological entities is generally not revealed instantaneously, but instead after a period of time has been allowed to elapse, such that at least one incubation is generally desirable in order to bring out the effect of of compounds or agents on biological entities. Further, the effect of compounds or agents on biological entities can often be advantageously determined by exposing at least two specimens of microdroplets to different concentrations of the compounds or agents. In order to interpret changes caused by the exposure of biological entities in MDs to compounds and agents, it is often desirable that at least one specimen of MDs not be exposed to the compounds or agents, thereby providing at least one control condition.

The effects of many compounds and agents on biological entities can be determined by this invention, including the effects of compounds such as antibiotics, antimicrobial compounds, antifungal compounds, chemotherapeutic compounds, toxic compounds, cytotoxins, irreversible inhibitors, reversible inhibitors, mutagenic compounds, hazardous compounds, hormones, growth factors, growth enhancers, nutrients, vitamins, food preservatives, pesticides and insecticides. Further, many different types of biological entities can be used in this invention, including small multicellular organisms, groups of cells, individual cells, protoplasts, vesicles, spores, organelles, parasites, viruses, nucleic acid molecules, antibody molecules, antigen molecules, and aggregates of molecules. It is preferred to use cells such as animal cells, plant cells, insect cells, bacterial cells, yeast cells, fungi cells and mold cells.

Additional flexibility can often be obtained by: (a) using at least two incubation periods, and (b) using at least one change in the concentration of the compounds between incubation periods. For example, if it is desired to test the reversability of a growth altering compound or agent, a first incubation can be used with the compound or agent present, followed by a second incubation with the compound or agent absent.

Control conditions can be provided by: (a) exposing a single specimen of microdroplets to at least one change in concentration of at least one compound or agent, (b) using a first incubation as a control for growth, and (c) using at least one subsequent incubation with exposure to the compound or agent, thereby providing a serial process in which a control is followed by exposure to compounds or agents Alternatively, a process can be carried out by: (a) exposing at least one specimen of microdroplets to at least one change in concentration of at least one compound, (b) using at least one other specimen of microdroplets without exposure to said compound, in order to provide a control for growth, and (c) using separate incubation of at least one exposed specimen and one control specimen.

More specifically, the process of this invention can be used to determine the antimicrobial susceptibility of microorganisms to various compounds. Specimens of GMDs which contain one or more microorganisms are exposed to an antimicrobial at one or more concentrations, and the growth determined by using an incubation for each concentration. By comparing the amount of growth at different concentrations, the effectiveness of the compound to inhibit growth of the microorganism at these concentrations can be determined. This determination corresponds to a determination of the antimicrobial susceptibility of that microorganism for the tested compound.

A related process provides determination of the sensitivity of cancer cells to compouds such as chemotherapeutic compounds, in which case it is preferred to use GMDs. Specimens of GMDs which contain one or more cancer cells are exposed to a compound at one or more concentrations, and the growth determined by using an incubation for each concentration. By comparing the amount of growth at different concentrations, the effectiveness of the compound to inhibit growth of the cancer cells at these concentrations can be determined. This determination corresponds to a determination of the chemotherapeutic susceptibility of the cancer cells to the tested compound. An advantage of the present invention is that it is possible to make measurements on GMDs which have a high probability of being occupied by a small numbers of cells, preferably less than two cells. Further, measurements can be made on large numbers of GMDs which contain cells. As a result, for example, this invention provides the ability to determine the chemotherapeutic susceptibility of large numbers of individual cancer cells, for example 1,000 cells to 10,000 cells. Thus, it is possible to determine the distribution of amount of growth by a large number of cells, which growth is not necesarily identical, thereby allowing the distribution in cancer cell growth to be determined. This, in turn, provides a determination of the distribution of susceptibility of the cancer cells to the compound. Thus, for example, if a subpopulation comprising 10% of the cancer cells is resistant to a compound, or mixture of compounds, significant growth will be found in about 10% of the occupied GMDs. Such determinations can have good statistical significance because a large number of individual GMD measurements can be made, wherein there is a high probability that GMDs are occupied by less than two cells.

Continuing this example, if a resistant subpopulation comprising about 10% of the cells is found on the basis of measuring $10^4$ cells, the number of GMDs occupied by resistant cells is about $10^3$. The corresponding statistical error in sampling, and therefore in determining the size of the resistant subpopulation, is due to the error in counting randomly occurring events. This statistical error is well known to be described by $\sqrt{N_{random\ event}}$ so that in this illustration the error is is $\sqrt{N_{resistant\ cell}} = \sqrt{10^3} = 32$, which corresponds to about 3% error, and is therefore highly accurate in determining the size of the resistant subpopulation.

Measurements of the amount of biological material in GMDs can provide the basis for measurement of growth, and other biological activity and function, by biological entities such as cells within GMDs. Suitable measurement means for measuring the biological material include optical, weighing, sedimentation, field flow sedimentation fractionation, acoustic, magnetic, electrical and thermal means. It is preferred to use optical measurement means, particularly measurements based on light scattering, light absorbance or colorimetric, fluorescence, time-delayed fluorescence, phosphorescence and chemiluminescence.

As described elsewhere in this disclosure, groups of microdroplets consisting predominantly of single microdroplets can be simultaneously measured, or, alternatively, groups of microdroplets consisting predominantly of at least two microdroplets can be simultaneously measured. As also described elsewhere, the measured microdroplets can consist predominantly of gel microdroplets with a high probability of containing less than two biological entities prior to incubation Alternatively, the measured microdroplets can consist predominantly of microdroplets with a high probability of containing at least two biological entities prior to incubation.

Finally, this invention can be used with a step wherein measurement of growth is used to determine the effect of at least one compound on growth characteristic behavior selected from the group consisting of plating efficiency, growth rate distribution, average growth rate, growth lag time distribution and average growth lag time Enumeration of Viable Biological Entities This invention involves also the determination of the number of viable biological entities per volume, which comprises enumeration of viable biological entities, a measurement which is widely used in biology and medicine. For example, it is common to determine the number of viable microorganisms per ml of a fluid sample. In this process it is important to make determinations which are rapid, based on the number of microorganisms, and based on a stringent criterion for microorganism viability. As described herein, it is often possible to extend the concept of growth to include the growth of biological entities such as small multicellular organisms, groups of cells, individual cells, protoplasts, vesicles, spores, organelles, parasites, viruses, nucleic acid molecules, anti-body molecules, antigen molecules, and aggregates of molecules. It is preferred, however, to carry out the process of this invention with cells such as animal cells, plant cells, insect cells, bacterial cells, yeast cells, fungi cells and mold cells, particularly for normal human cells, human cancer cells, pathogenic bacteria, pathogenic yeast, mycoplasms, parasites, and pathogenic viruses. This invention provides a general means for rapidly enumerating such biological entities using the criterior viability based on growth, and also, for some biological entities, using criteria provided by vital stains.

More specifically, this invention provides means for determining the number of viable biological entities per volume of a sample, the process comprising the steps of: (a) exposing at least one MD, which contains at least one biological entity, to conditions for which the number of viable biological entities is to be determined, (b) measuring biological material in GMDs, (c) measuring the volumes of the associated GMDs, and (d) thereby determining the number of viable biological entities per volume in the sample. In cases wherein MD volumes are not known, the additional step of measuring MD volumes is used. Prior to making this determination, it is necessary to incorporate biological entities into MDs. This can be accomplished using previously described means for forming MDs with sample material which contains biological entities.

Although an indication of viability can, in some cases, particularly for certain types of cells, be determined by use of vital stains such as membrane potential responsive dyes, membrane exclusion dyes such as the light absorbance dye trypan blue, and such as the fluorescent dyes propidium iodide and ethidium bromide, and intracellular enzyme/membrane integrity dyes such as fluorescein diacetate, carboxyfluorescein diacetate and fluorescein isothiocyanate diaceate, (see, for example, Shapiro, *Practical Flow Cytometry*, A. R. Liss, New York, 1985) it is generally desirable to use a more stringent criterion for determining that a biological entity is viable. Many biological entities, particularly cells and viruses, are stringently determined to be viable only by determining that the biological entities are capable of growth, that is, of increasing in size and/or number. Thus: the present invention can be utilized to enumerate biological entities by a process wherein at least one incubation is provided, in order to provide an opportunity for growth prior to measurement of the amount of biological material in MDs.

In the practice of this invention it is preferred to measure the change in the amount of biological material in MDs subsequent to one or more incubations. More specifically, it is preferred to utilize MDs with individual occupation such that the amount of biological material associated with individual biological entities, particularly cells, can be measured prior to at least one incubation, and also subsequent at least one incubation, so that the change in amount of biological material is measured. Thus, it is particularly useful to carry out the preceeding process wherein the change in amount of biological material is used as an indication of viability of biological entities.

In cases in which the stringent criterion of biological entitiy growth is not required as the basis of determining viability, and the biological entities consist of small multicellular organisms, groups of cells, cells, protoplasts, vesicles, spores, organelles and parasites, it is possible to use this invention with short incubation, or essentialy no incubation, by using vital stains in combination with the volume measurements of MDs. Vital stains respond to one or more important biochemical or physical functions of biological entities, particularly cells, such that said functions can often be measured more rapidly than growth. Representative types of vital stains include transmembrane potential stains, membrane exclusion stains and intracellular enzyme activity responsive stains. Specific vital stains include cyanine dyes, propidium iodide, ethidium bromide, fluorescein diacetate, carboxyfluorescein diacetate and fluorescein isothiocyanate diacetate. Thus, by exposing MDs to at least one vital stain and subsequently measuring both the vital stain and volumes of the associated MDs, an enumeration of viable biological entities can be obtained.

Although this invention can be used to obtain an approximate enumeration without statistical analysis applied to the MD measurements, the most accurate determinations involve statistical analysis which utilizes both biological material measurement and MD volume measurement. Such statistical analysis involves scoring each MD, or specimen of MDs, as occupied or unoccupied. Additional information can be obtained by further scoring each MD according to the amount of biological material, so that growth of biological entities is measured and used as the basis for determining viability. In the case that each MD, or specimen of MDs, is scored as occupied or unoccupied, the volume of the corresponding MD, or volume of the corresponding specimen of MDs, is utilized, such that a statistical frequency distribution of the occurence of occupation for different ranges of MDs volumes, or MD specimen volumes, is determined from the measurements, and this frequency distribution used to determine the average number of viable biological entities per volume of sample which was used in the formation of MDs, and which therefore comprises a viable enumeration for the sample.

It is preferred to utilize Pisson statistics or modified Poisson statistics with the measured frequency-of-occurrence of occupation in MDs within different MD volume ranges. As in the conventional, standard method of viable plating of cells, random mixing and the Poisson probability distribution are used to obtain an enumeration. The use, if necessary, of iterative computations results in a self-consistent determination described by the Poisson probability function if the biological entities were randomly distributed into MDs during the MD creation process. An initial, trial value of $\rho$ is used, and the initial occupation distribution for the measured $V_{MD}$ distribution is computed. The initial value of $\rho$ is then adjusted, according to whether the computed distribution results in more or less occupation than measured. This process is continued until there is agreement, preferably to within 10 to 30%, but depending upon the application, and then this value of $\rho$ is corrected for dilution to obtain $\rho_s$, which is the desired viable cell enumeration, expressed as the number of viable biological entities per volume of sample.

The average number of initial biological entities, n, in MDs within a range of volumes $V_{MD}$ is related to the sample's cell concentration, $\rho$, through the relation $$\bar{n} = \rho V_{MD} \text{ so that } \rho_S = \frac{\bar{n}}{f_D V_{MD}} \quad (8)$$

provides a determination of $\rho_S$, the viable enumeration. Here $f_D$ is the dilution factor defined by equation (3). The determination of $\bar{n}$ and $V_{MD}$ for a statistically significant number of occupied MDs allows $\rho_S$ to be determined with sufficient accuracy, typically $\pm 10\%$, to $\pm 30\%$, which is better or about the same as typical enumerations obtained by conventional viable plating. If desired, increased accuracy in $\rho_S$ can be obtained by making and using measurements on a larger number of occupied and unoccupied MDs and/or groups of MDs.

Computation using suitable probability distributions such as the Poission probability formula, or modified Poisson statistics formulae, is also used, self-consistently, to identify which range of sizes within a MD specimen have a high probability of being unoccupied, individually occupied or multiply occupied. Examples of suitable MD creation processes are described elsewhere in this disclosure. An advantage of processes which produce a wide range of MD sizes is that a wide range of sample cell concentrations, $\rho$, can be used. These conditions are useful for samples having a large specimen of MDs in which some significant fraction of the MDs will have volumes which correspond to having a high probability of being unoccupied or individually occupied.

After formation, the MDs are placed in desired conditions for determining growth. Typically MDs can be suspended, or located, in a medium of a wide range of different compositions, and at different pH, temperature, partial pressures of oxygen and carbon dioxide, etc., so that, as described elsewhere in this disclosure, growth under a wide range of growth medium conditions can be determined.

After an incubation period the MDs are exposed to one or more staining processes, depending on the type of biological entity and the purpose of the growth determination. In the general case wherein growth analysis without further use of the biological entities is desired, any staining process, including both those which kill biological entities and those which do not kill entities, can be used. In the case wherein further analysis or use of viable biological entities is desired, staining which allows biological entitiy survival is used.

Following exposure of the MDs to suitable stains, MDs are individually measured, or measured in small groups, provided that the probability of finding more than one biological entity-containing MD in the group is small. In the exemplary case of cells stained by fluorescent compounds, optical analysis such as digital fluorescence microscopy or flow cytometry is used to analyze individual MDs, or groups of MDs, using a wavelength band sufficiently different from that used for any detection of measurement of MD properties. Thus, simultaneous, or serial, measurement of MD properties and of cells within said MDs is possible. The associated fluorescence signals are acquired and analyzed, with correction for spectral overlap if necessary, by conventional means.

The magnitude of the optical signal due to the biological entity stain in each MD, or MD group, is compared to the fluorescence of individual cells, whether or not such individual biological entities are entrapped in MDs, thereby providing a calibration. Comparison of the MD, or MD group, signal magnitude to that of individual biological entities provides the basis for determination of growth of individual biological entities. For example, in the important case of cells, such comparison of signal magnitude provides the basis for determination of growth of individual cells into microcolonies of two or more biological entities, which can be made within about one generation time, but without a need for significant prior culture to obtain large numbers of cells, and provides the basis for establishing that the occupied MDs contain viable cells, as determined by the requirement of growth from one into two or more cells.

This invention can be used to obtain a viable enumeration of biological entities such as small multicellular organisms, groups of cells, individual cells, protoplasts, vesicles, spores, organelles, parasites, viruses, nucleic acid molecules, antibody molecules, and aggregates of molecules It is preferred to use this invention to enumerate cells such as animal cells, plant cells, insect cells. bacterial cells, yeast cells, fungi cells and mold cells.

Representative suitable means for measuring biological material within MDs, using naturally occuring properties of biological entities, or using stains, includes physical means such as optical, weighing, sedimentation, field flow sedimentation fractionation, acoustic, magnetic, electrical and thermal means. It is preferred to use optical measurements wherein biological material and gel microdroplet volumes are measured using optical phenomenona such as light scattering, light absorbance or colorimetric, fluorescence, time-delayed fluorescence, phosphorescence and chemiluminescence.

Optical measurements can be often enhanced by treating or exposing MDs to at least one staining process, wherein at least one stain is utilized to enhance the measurement of biological material. Representative suitable types of stains include stain indicative of biological composition, stain indicative of enzyme activity, and stain indicative of cell membrane integrity Such stains are generally selected to have readily measureable properties such as fluorescent stains, light absorbance stains and light scattering stains, and can be further selected according to the class of biological material which is stained, including, therefore, stains such as nucleic acids stains, protein stains, lipid stains, cell membrane stains, cell wall stains, stains responsive to enzyme activity, stains responsive to transmembrane potentials and cell surface receptor stains.

It is also useful to practice this invention wherein optical measurement is made using apparatus such as flow cytometry apparatus, flow-through-microfluorimetry apparatus, optical particle analyzers apparatus, fluorescence microscopy apparatus, light microscopy apparatus, image analysis apparatus and video recording apparatus Electrical measurements also have significant advantages, as electrical signals can be coupled directly to computational means. Thus, it is useful to practice this invention by employing electrical measurement means to measure biological material within MDs and also the volume of MDs. Electrical measurements useful with GMDs include those involving electrical resistance particle analysis apparatus and dielectric property measurement apparatus, while those useful with LMDs involves dielectric property measurement apparatus.

For example, it is well established that a resistive cell counter, often termed a Coulter Counter, can use electrical resistance measurement to determine cell volume (see, for example, Kachel in *Flow Cytometry and Sorting*, Melamed et al (Eds), Wiley, N.Y., pp. 61-104). In the case of GMDs, the gel matrix of GMDs generally has a high molecular weight cutoff property, such that only large molecules are excluded, with the result that the gel matrix offers only small electrical resistance if GMDs are suspended in an aqueous medium comprising an aqueous electrolyte with small ion composition similar to that of physiological saline (about 0.9% NaCl). For this reason, GMDs without biological entities such as small multicellular organisms, cells, protoplasts, vesicles and spores have electrical resistance essentially indistinguishable from such aqueous electrolytes, and therefore are not electrically measured, while cells contained with the GMDs are measured. Specifically, formation of microcolonies in GMDs leads to electrical resistance of the GMDs which increases with microcolony size, and thereby provides an electrical means for measuring the amount of biological material in GMDs.

The volume of the corresponding GMDs, or specimens of GMDs, can be obtained by using other means, including optical means responsive to the gel matrix of GMDs, or responsive to marker entities provides within GMDs. Alternatively, by providing marker entities with measureable electrical or magnetic properties in GMDs, it is possible to measure the volume of the corresponding GMDs, or specimens of GMDs, by electrical or magnetic means. For example, by providing marker entities comprising particles of a high dielectric constant such as barium titanate, it is possible to measure the total amount of such dielectric material in each GMD, or specimen of GMDs, and thereby to measure the volume of said GMDs. A similar embodiment involves the use of marker entities with measureable magnetic properties, such as magnetite particles which have measureable magnetic properties which can be measured by well known means such as positioning a coil in proximity to the orifice of the resistive particle counter. In these exemplary cases the electrical resistance of GMDs can be insignificantly altered by the presence of the marker entities, because even in the case that large numbers, e.g. $10^5$, of marker entities are used in a $50\mu$ diameter GMD, the spacing of the marker entities within the gel matrix is sufficient so as to not significantly impede the movement of the small ions which predominantly determine the electrical resistance of such GMDs

Measurements on Mixed Biological Populations

Although many samples contain a single type of biological entitity, for example, a monoculture of microorganisms wherein all of the microorganisms are of the same type, a great many samples obtained in biology and medicine are mixed populations, in that at least two types of biological entities are present in the sample, generally such that neither the relative numbers of the different types nor the absolute numbers is known a priori. The present invention provides general means for measuring biological entities in mixed population samples, while requiring minimal or no pretreatment of the sample, and can yield such measurements rapidly. The general process of this invention comprises the steps of: (a) creating microdroplets from a sample of the mixed population, and (b) making at least one measurement which is sensitive to at least one type of biological entity, and one additional measurement which is sensitive to at least one other type of biological entity.

In this process it is preferred that there is a high probability that each MD contains less than two types of biological entities, but the process can also be carried out under conditions in which there is a high probability that each MD contains at least one type of biological entity. In many cases, but not all, it is further desirable to provide the additional step of measuring MD volumes.

For example, formation of MDs which are LMDs from a sample containing two different types of microorganisms, I and II, with I having significantly greater metabolic acid production and secretion rate than II, when provided with the particular growth medium provided. Then, with or without dilution of the sample, by forming LMDs which have a range of volumes, $V_{MD} = V_{LMD}$, or forming LMDs which have essentially the same volume, LMDs can be formed which have a high probability of being unoccupied or individually occupied, so that each occupied LMD has a high probability of containing one initial type I, or one initial type II, microorganism. By providing optical pH indicators, either light absorbance or fluorescent, the LMDs can be incubated such that the acid production of the type I allows measurement and identification of the LMDs which contain that microorganism, thus providing the basis for measurement of one type of biological entity in that mixed population.

In another example, if GMDs are formed from a suspension containing two different types of cells, type A and type B, comprising the mixed biological sample, and it is further assumed that: (a) type A grows significantly faster than type B for the conditions provided, and (b) type A can be labeled with a Green Fluorescence labeled antibody to type A surface antigens, and type B can be labeled with a Red Fluorescence labeled antibody to type B surface antigen, then the growth of type A and type B can be separately and simultaneously determined. Continuing this example, a portion of the mixed population sample is converted into GMDs, thereby incorporating cells of both types into GMDs. A specimen of the GMDs can be exposed, simultaneously or consecutively, to both antibodies, such that antibodies enter the GMDs and bind to surface antigens, thereby labeling the amount of biological material, in this case amount of surface antigen, for both cell types. The amount of Green Fluorescence and Red Fluorescence in GMDs is then measured, to thereby provide a measurement of the amount of biological material associated with type A and type B. Following incubation of at least one additional specimen of the GMDs at desired conditions, growth of both types of cells is allowed to occur. All or a portion of this specimen can then be exposed to the same preparation of fluorescence-labeled antibodies, which provides a distinguishable measurent of the amount of biological material associated with type A and type B. The measured amount of each type of biological material can then be quantitatively compared with an amount of biological material of each type in non-incubated GMDs, thereby providing a measurement of the growth of each type of cell in the sample. As demonstrated by this example, GMDs are used to contain biological entities so that growth can be measured, but the volume of the GMDs need not necessarily be measured.

Although measurement of at least one type of biological entity of a mixed population is often desired, it is possible to use the results of such measurement process to further provide the basis of physical isolation of MDs containing one type of biological entity. In this further process, the value of at least one measurement is used to provide the basis for applying at least one force to the corresponding MDs. This force results in physical manipulation of such MDs, and then physical isolation of such MDs. In this way MDs containing a first type of biological material are isolated from MDs not containing the first type of biological material. Following such isolation of MDs the biological entities contained within the MDs can be isolated or removed from the MDs by methods described elsewhere in this disclosure, thereby providing isolation of the biological entities Although measurements of a mixed population sample do not in all cases require measurement of the volume of the associated MDs, in most cases, the practice of this invention involves the measurement of MD volumes and the use of statistical analysis to determine the number of biological entities in MDs. In such cases, it is preferred to use statistical formulae such as Poisson statistics and modified Poisson statistics. These formulae provide a relation between the volume, $V_{MD}$, the particular occupation or number, n, of initial biological entities in a MD, and the average number, n, of biological entities in a MD of this volume. Thus, by applying these formulae in an iterative fashion, which is generally well known, and which can readily by accomplished using a computer, in the process of this invention, the probability that a measured MD has individual occupation can be determined. By then further using measurements which can distinguish at least two types of biological entities, it is possible to catagorize MD measurements into at least two catagories, and which, through the use of the statistical formulae, have a high probability of relating to measurements on only one type of biological entity.

Thus, to summarize this process, as a result of statistical anlysis on measurements which distinguish at least two types of biological entities and on MD volume measurements, the measurements which have a high probability of relating to at least one type of biological entitity from a mixed population sample can be obtained. Such measurement results are possible because the process of this invention provides a statistical, usually essentially random, separation of biological entities into MDs, such that the subsequent measurements and statistical analysis allow separated measurements of biological entities. Thus, using this and similar versions of the method described herein, it is also possible to make useful measurements on a mixed sample under conditions where measured GMDs have a high probability of containing less than two biological entities.

Although it is preferred to make measurements using MDs which are individually occupied, it is possible to make useful measurements even if MDs are multiply occupied. For example, as previously described, if two cell types, type A and type B, are measured by using antibodies for surface antigens, and one antibody has a Green Fluorescence label and the second a Red Fluorescence label, the growth of each type of cell can be separately determined.

In another example, if the average occupation due to all types of biological entities of interest, $\bar{n}$, is greater than about $\bar{n}=0.15$, the probability of initial occupation by an individual biological entity decreases, such that if $\bar{n} >> 0.15$ most MDs are multiply occupied. Even in the case of such multiple occupation, however, it is often possible to make useful measurements on MDs formed from a mixed population. For example, if $\bar{n}=3$, for a given size range of MDs, then as described elsewhere in this disclosure, the probability of having $n>7$ is small, so that there is a low probability of having more than 6 of one type in the presence of the other type. In many cases the biological entities differ significantly in properties such as biological material composition, or in growth, so that useful measurements can be made in such cases. However, as previously described, the preferred use of this invention is to utilize GMDs which have a high probability of containing at least one biological entity.

The use of this invention with measurements which determine growth of at least one type of biological entity is particularly useful, and can be further extended by exposing at least one specimen of GMDs to conditions which affect the growth of at least one type of biological entity. For example, the use of selective growth media is well established in microbiology. The use of such media allows the outgrowth, typically accomplished with long incubations which correspond to a large number of doubling times of the selected microorganisms in the presence of large numbers of other types of microorganisms. Specifically the microorganisms include those which do not grow, or grow much more slowly, than the selected type. Identical or similar selective media can be used with this invention, but it is not necessary to incubate for long periods. In this case it is preferred, but not necessary, to use Poisson statistics or other suitable statistics to identify GMDs which have a high probability of individual occupation.

It is often useful to practice this invention by exposing microdroplets to conditions which affect the growth of at least one type of biological entity. For example, consider the illustration wherein the MDs are GMDs, and the provision of a selective medium results in zero growth of one type of bacteria and growth of a second bacteria type such that the doubling time for the growing type is $t_2=30$ minutes, and that the lag time for establishing growth is only a few minutes. In this case, following an incubation of approximately one hour the non-growing bacteria will still be present as single bacteria, such that GMDs with $n=1$ or individually occupied GMDs will have either single bacteria if occupied by the non-growing type, or will have microcolonies of 4 bacteria if occupied by the growing type. Continuing this illustration, if each type of bacteria has essentially the same magnitude of Red Fluorescence signal following the use of a propidium iodide staining protocol, the non-growing individual cells and microcolonies of 4 cells can be readily distinguised. Individually occupied GMDs with growing bacteria will have Red Fluorescence signals about four times those of individually occupied GMDs with non-growing bacteria.

It is also useful to practice this invention by comparing the growth of at least one type of biological material contained in microdroplets to the growth of at least one other type of biological material contained within the microdroplets. For example, consider a related illustration, wherein again two types of bacteria comprise a mixed population, but now with the less optimal case wherein the selective conditions result in non-zero but different growth rates. Specifically, consider the case wherein type A has a doubling time, $t_{A2}=30$ minutes, and type B has a doubling time, $t_{B2}=45$ minutes. In such a case it is preferred, but not necessary, to use Poisson statistics or other suitable statistics to identify GMDs which have a high probability of individual occupation. In this case, assuming a lag time of only a few minutes, following an incubation of approximately 60 minutes, the type A bacteria will be present in individually occupied MDs as microcolonies of about 4 cells, cells, while the type B bacteria will be present as microcolonies of about 2.5 cells. Thus, individually occupied GMDs, i.e. GMDs initially containing one cell, will have either microcolonies comprised of about 4 cells if type A, or will have microcolonies of about 2.5 cells if type B. Continuing this example, if each type of bacteria has essentially the same magnitude of Red Fluorescence signal following the use of a propidium iodide staining protocol, the microcolonies of about 4 cells and microcolonies of about 2.5 cells can be readily distinguised, as the Red Fluorescence signals will be proportional, in this example, to microcolony size. Using this type of measurement and analysis, the average growth rate of both types of cells can be simultaneously determined from the mixed sample. This illustrates a basic method for making rapid measurements on a mixed population. This example also serves to illustrate the use of this invention to use biological growth to distinguish at least two types of biological entities using biological growth Many variations of this example, including straightforward extension to more than two cell types, are possible.

A general version of this invention involves the use of measurement of biological material with sufficient specificity that at least one type of biological material can be distinguished from at least one other type of biological material. For example, fluorescence-labeled antibodies to surface antigens provide a general basis for such specificity of biological material measurements. This has been described previously by means of an example based on a Green Fluorescence labeled antibody to a first surface antigen, and a Red Fluorescence labeled antibody to a second surface antigen, with growth of both cell types then possible.

The process of this invention further allows viable enumeration of one or more biological entities of a mixed population sample. As illustrated previously, the growth of different types of biological entities can be determined separately and simultaneously. By further utilizing MD volume measurements with a statistical analysis based on Poisson statistics or other suitable statistics, the number of viable biological entities per volume of sample can be obtained for one or more types of biological entities, which comprises obtaining a viable enumeration of at least one type of biological entity Differences in growth under selective medium conditions can be enhanced by exposing one or more specimens of GMDs to compounds which significantly alter growth, such that one or more incubations of GMDs are provided with such compounds present. This allows two or more types of biological entities to be measured by significantly altering the growth of at least one type of biological entity. Examples of suitable growth altering compounds include antibiotics, antimicrobial compounds, antifungal compounds, chemotherapeutic compounds, toxic compounds, cytotoxins, irreversible inhibitors, reversible inhibitors, mutagenic compounds, hazardous compounds, hormones, growth factors, growth enhancers, nutrients, vitamins, food preservatives, pesticides and insecticides In addition to making measurements of differential growth and/or measurements which measure different types of biological material, the process of this invention can be further extended by making measurements which are indicative of different types of biological entity function. More specifically, it is useful to make measurements wherein at least two types of biological entities are determined by a measurement selected from the group consisting of biological material, biochemical activity, production of molecules, degradation of molecules, secretion of molecules, metabolism, membrane integrity, enzyme activity and growth. Thus, for example, if biological entities such as cells differ in their ability to produce molecules, the resulting differences in production can be measured by using a stimulus such as electroporation to release molecules for capture at binding sites and subsequent measurement. Finally, if biological entities such as cells differ in their enzyme activity when exposed to certain conditions, and the resultant differing enzyme activity is measured, this type of measurement also distinguishes types of biological entities.

As described previously, optical means are preferred for measurement of biological material and microdroplet volumes, using optical phenomena such as light scattering, light absorbance or colorimetric, fluorescence, time-delayed fluorescence, phosphorescence and chemiluminescence. It is also often useful to incorporate marker entities into GMDs in order to enhance microdroplet volume measurement, using marker entities such as beads, non-biological particles, crystals, nonaqueous fluid inclusions, viable cells, dead cells, inactive cells, virus, spores, protoplasts, vesicles, stains and dyes. Alternatively, it is possible to pretreat GMDs so as to attach marker entities to at least one gel matrix constituent. Furthermore, marker entities can be incorporated into microdroplets after creation of the microdroplets.

Alternative measurement means include optical, weighing, sedimentation, field flow sedimentation fractionation, acoustic, magnetic, electrical and thermal means. Further, as described elsewhere in this disclosure, it is useful to use optical measurements are selected from the group consisting of light scattering, light absorbance or colorimetric, fluorescence, time-delayed fluorescence, phosphorescence and chemiluminescence This process of this invention can also involve the additional step of exposing microdroplets to at least one compound which affects biological material prior to measurement, thereby enhancing the distinction between at least two types of biological entities.

This invention can be used with mixed popultions in order to make measurements of biological entities such as small multicellular organisms, groups of cells, individual cells, protoplasts, vesicles, spores, organelles, parasites, viruses, nucleic acid molecules, antibody molecules, antigen molecules, and aggregates of molecules, and it is preferred to make measurements on cells such as animal cells, plant cells, insect cells, bacterial cells, yeast cells, fungi cells and mold cells, and also cells such as normal human cells, human cancer cells, pathogenic bacteria, pathogenic yeast, mycoplasms, parasites, and pathogenic viruses.

Furthermore, although this invention can be carried out by measuring the amount of biological material in at least one gel microdroplet by measuring a naturally occuring optical signal associated with the biological material, such as optical signals selected from the group consisting of light scattering, light absorbance or colorimetric, fluorescence, time-delayed fluorescence, phosphorescence and chemiluminescence, it is preferred to utilize at least one staining process involving at least one stain for biological material. Representative types of stains which can be used are stains such as stain indicative of biological composition, stain indicative of enzyme activity, and stain indicative of cell membrane integrity.

It is also useful to practice this invention in an embodiment wherein at least one stain is used for biological entity identification and at least one stain or a naturally occuring optical signal is used to determine biological entity growth. A particularly useful general version of this embodiment involves the use of at least one fluorescence-labeled antibody is used for biological entity identification.

Thus, this invention can be used to make a variety of measurements on mixed biological populations which cannot be readily made by prior methods.

Provision of External Influence on Biological Entities

In many tests and assays the interaction of biological entities with external sources of chemicals, biological factors or physical fields are extremely important, and it is highly desirable to provide means for extending MD measurement and isolation processes to include the effects of such influence. In order to provide such external influence on biological entities, the biological entities are incorporated into MDs, so the MDs which contain biological entities can be introduced into position of proximity to a source, maintained in position in proximity to a source or removed from proximity to a source. In the general practice of this invention, sources of influence include biological sources of influence, chemical sources of influence, physical sources of influence, and combinations of biological, chemical and physical sources of influence are provided by using MDs, In general, however, it is often preferred to provide influence by utilizing MDs which are GMDs, particularly GMDs which are surrounded by an aqueous medium such that the aqueous medium contacts the aqueous interior medium of GMDs, thereby allowing chemical and small biological entities to be exchanged between the GMDs and the aqueous medium. It is also possible to provide influence by using LMDs and/or GMDs surrounded by a non-aqueous fluid, as most types of physical influence is readily provided, but the chemicals which can be exchanged is more limited, and relatively few biological entities can be exchanged. For aqueous surrounded GMDs, exemplary surrounding aqueous media include aqueous growth medium, physiological fluids, human body fluids, animal body fluids, organ perfusates, suspensions of cells, suspension of small multicellular organisms, animal tissue homogenates, plant tissue homogenates, cell culture medium, culture medium for microorganisms containing biological material, defined culture medium for microorganisms, defined culture medium for mammalian cells, blood, blood plasma, urine, cerebral spinal fluid and interstitial fluid. Upon exposure of GMDs to one or more such aqueous media or environments, and depending on the molecular filteration characteristics of the gel matrix, most chemical compounds and some small biological entities can enter the GMD by partitioning into the aqueous environment of the gel matrix. These can be transported, often by diffusion, but also by drift and/or convection, within the GMD, thereby exposing biological entities contained within GMDs to chemical compounds and/or small biological entities contained within the aqueous environment.

In the case of such GMDs, the present invention provides means for influencing biological entities to external influence thought the general means of providing physical forces which allow manipulation of GMDs, such that GMDs can be moved into and within an aqueous environment. Such manipulation of GMDs allows GMDs to be positioned in proximity to sources of influence which are external to GMDs, such that chemical compounds of the aqueous environment in proximity to one or more external sources can enter GMDs and thereby interact with biological entities within GMDs, and thus provide influence on the biological entites. More specifically, this process provides a general means for providing external influence on biological entites by utilizing physical manipulation of GMDs, containing at least one biological entity, so as to affect the proximity of at least one GMD to an influence source which is external to the GMDs. Thus, it is particulalry useful to provide influence on biological entities by utilizing GMDs in an aqueous fluid.

However, because of the greater generality of this invention, it is appropriate to describe most of this invention in terms of the use of the more general case of MDs surrounded by either aqueous fluids or non-aqueous fluids. Following the provision of influence, it is generally useful to determine the effect of the influence on biological properies of biological entities contained within the MD. This is particularly relevant for biological properties such as biological material, biochemical activity, production of molecules, degradation of molecules, secretion of molecules, metabolism, membrane integrity, enzyme activity and growth, as these are directly or indirectly involved in many assays and tests In order to flexibly provide influence due to one or more biological sources it is useful to provide such biological influence by selecting a source from the group consisting of cells, feeder cells, animal tissues, plant tissues, animal tissue homogenates, plant tissue homogenates, perfused organs, whole animals, plants, cell suspensions, biological entities within gel microdroplets, cell cultures, body fluids.

As used herein, the term biological influence describes the influence associated with chemical compounds and small biological agents such as phage, which have biological origin and can be present in the aqueous environment in proximity to a biological source. Representative biological sources include cells, feeder cells, animal tissues, plant tissues, animal tissue homogenates, plant tissue homogenates, perfused organs, whole animals, plants cell suspensions, biological entities within gel microdroplets, cell cultures, body fluids. Chemical sources include any entity which provides to an aqueous environment one or more chemical compounds, and can therefore include biological sources. Physical sources include any entity which is the source of physical conditions in an aqueous environment. These include physical processes such heat, electrical energy, magnetic energy, optical energy, radioactivity or ionizing radiation, and acoustic energy which alter chemical composition of chemical compounds in an aqueous environment. Physical sources also include any entity which directly provides heat, electrical energy, magnetic energy, optical energy, radioactivity or acoustic energy to MDs, thereby providing influence on biological entities contained within MDs.

By using the process of this invention in which MDs can be manipulated, including specifically manipulation which results in MDs being near, maintained near and removed from one or more sources of external influence, external influence can be caused on biological entities such as small multicellular organisms, groups of cells, individual cells, protoplasts, vesicles, spores, organelles, parasites, viruses, nucleic acid molecules, antibody molecules, antigen molecules, and aggregates of molecules It is particularly useful to provide influence on cells such as animal cells, plant cells, insect cells, bacterial cells, yeast cells, fungi cells and mold cells, and such as normal human cells, human cancer cells, pathogenic bacteria, pathogenic yeast, mycoplasms, parasites, and pathogenic viruses In the important case of mammalian cells it is preferred to provide influence on cells such as of normal human cells, cancerous human cells and hybridoma cells.

In order to provide complex biological influence, wherein many different and complex biochemical pathways may be involved, and wherein different tissues may participate, it is possible to reversibly position MDs, particularly GMDs, within whole animals such as mouse, immunodeficient mouse, rat, rabbit, primate, goat, dog, horse, pig, guinea pig and and human being. These are important biological sources of external influence, and additional related sources comprise one or more perfused organs from such animals Thus, for example, GMDs containing magnetic force-coupling entities in addition to biological entities can be inserted into an animal, so that complex biological influence can be provided. If desired, the biological entities within the GMDs can be protected from an immune response by the animal by providing an appropriate molecular weight cutoff property for the gel matrix of the GMDs. An exemplary means for accomplishing this protection is to use composite GMDs wherein an outermost gel region surrounding one or more biological entity-containing regions is used with a gel with a moderately low molecular weight cutoff.

Additional flexibility can be provided by supplying influence due to one or more sources which are themselves contained within MDs, and in this general case it is the relative position of the influencing MDs and the influenced MDs which is important. Thus either or both types of MDs can be manipulated The flexibility of this invention can also be increased by providing and utilizing gel material for MDs which are GMDs wherein the gel matrix which allows selective passage of molecules.

In order to physically manipulate MDs with respect to one or more sources of influence, the process of this invention provides physical forces such as, wherein the means for generation of such forces is well-known or is described elsewhere in this disclosure In order to more effectively provide such forces it is useful to supply one or more types of coupling entities, or force-coupling entities, wherein such entities are selected from the group consisting of beads, non-biological particles, bubbles, and non-aqueous fluid inclusions with force coupling properties selected from the group consisting of ferromagnetic properties, diamagnetic properties, paramagnetic properties, dielectric properties, electrical charge properties, electrophoresis properties, mass density properties, and optical pressure properties It is generally preferred to provide magnetic force by incorporating magnetic coupling entities into MDs, and an exemplary type of magnetic force coupling entities are those comprised of magnetite.

Forces for MD manipulation near sources of influence can also be provided by incorporating coupling entities with a mass density different than the gel density, so that physical forces such as field flow sedimentation fractionation force, acoustic force, gravitational force, centripetal force, centrifugal force and non-rotational acceleration force can be utilized.

An illustration of a source of physical influence relates to manipulations and measurements involving the use of heat and ionizing radiation for treatment of cancer, wherein cancer cells can be killed by application of heat and/or ionizing radiation. The use of ionizing radiation is well established as a therapeutic modality for the treatment of cancer, and the use of elevated temperature, or hyperthermia, either alone or in combination with ionizing radiation, has been more recently established as a therapeutic modality. In such treatments, a general tendency of increased cancer cell killing relative to normal cell killing is exploited. In order to carry out in vitro tests of the sensititivy, and the variability of sensitivity, of cancer cells to heat and/or ionizing radiation, cancer cells can be incorporated into GMDs. The GMDs are then exposed to the physical influence comprising elevated temperature and/or exposure to ionizing radiation, and then, if desired, incubated. The MDs are then measured for changes in the amount of biological material or biochemical activity. It is preferred to measure the amount of biological material relative to one or more controls, thereby providing a measure of growth of the cells exposed to physical influence relative to the growth of control cells in which are not exposed to the physical influence. Further, staining protocols can be used which test for membrane integrity. Thus, the fluorescent stain propidium iodide, and additional or separate staining with vital stains such as FITC diacetate can be used as the basis of a short term indicator of viability.

The process of this invention relating to provision of physical influence can also be carried out under conditions that approximate in vivo conditions. For example, GMDs containing cells to be tested can be placed within the body of an animal, such as a immunocompromised mouse, and the animal then exposed to conditions which approximate hyperthermia and/or ionizing radiation treatment in animal species, including humans. This provides external influence on the cells which is a combination of physical influence relating to heat and-/or ionizing radiation, and also external biological influence relating to the biochemical environment within the so treated animal. Following such provision of external influence on cells, measurements such as those relating to cell death, cell survival, cell growth and biochemical activity can be carried out using aspects of this invention described elsewhere in the present disclosure. Thus, exposure to heat influence can be provided and utilized to determine cell death and cell growth under conditions relating to cancer hyperthermia treatment.

Similarly, the effect of the physical influence of ionizing radiation on biological entities, particularly normal mammalian cells and cancerous mammalian cells, can be tested by the process of this invention, either under completely in vitro conditions, or, by inserting MDs, particularly GMDs, into a test animal, or even a human being, under essentially in vivo conditions. Thus, this invention can be used to determine cell death and cell growth under conditions relating to cancer radiation treatment.

The process of this invention can also be applied to combinations of cancer treatment which include sequential or simultaneous combinations of physical treatment such as ionizing radiation and hyperthermia, and chemical treatment, including established chemotherapy and newer therapy based on monoclonal antibodies and the like.

In the preferred embodiment of this invention, one or more sources of external influence are selected from the group consisting of mammalian cells, yeast cells and bacterial cells. In the case of mammalian cell culture, biological entities such as cultured mammalian cells can be exposed to "feeder cells". These "feeder cells" comprise the external source of influence, which in this case, are compounds which enhance the growth of cells. In addition, it is often preferred to influence biological entities, particularly cells, to the complex biochemical influence which is be provided by whole animals, especially animals selected from the group consisting of mouse, immunodeficient mouse, rat, rabbit, primate, goat, dog, horse and and human being. For example, the complex metabolic processes of whole animals can provide activation and degradation of chemical compounds which is generally difficult to duplicate in cell culture. Thus, the use of the present invention provides a general means for reversibly exposing biological entities such as cells to complex external influence resulting from whole animal activation and metabolism of chemical compounds.

In the preferred embodiment of this invention, biological entities are selected from the group of bacterial cells, yeast cells and mammalian cells, particularly normal human cells, cancerous human cells and hybridoma cells.

This invention can also be used in a version wherein one or more sources of external influence are incorporated into microdroplets, thereby providing a means for influencing biological entities wherein the source of influence can be manipulated by altering the position of the source with respect to the influenced biological entities which are in other MDs In this general case, different types of force can be used with the influencing MDs; for example magnetic force, while another force, for example, a force depenedent on the mass density of MDs, can be used with the influenced MDs Finally, in a related embodiment MDs sources of influence can be incorporated into MDs, and the resulting MDs manipulated so as to provide influence on biological entities which are not contained in MDs For example, feeder cells can be incorporated into GMDs with are also provided with magnetic force coupling entities such as magnetite, so that the feeder cells can be positioned in proximity to cultured cells which are not in GMDs, and, following any desired incubation, the GMDs containing the feeder cells can be readily removed.

Forces suitable for manipulation of MDs surrounded by a non-aqueous fluid are described elsewhere in this disclosure. Any of a variety of physical forces can be used to introduce GMDs surrounded by an aqueous fluid into close proximity to a source of influence, maintain GMDs in close proximity to a source of influence, and to remove GMDs from close proximity to a source of influence. Generally, the physical force is selected from the group consisting of electrical force, magnetic force, field flow sedimentation fractionation force, acoustic force, optical pressure force, gravitational force, sedimentation force, non-rotational acceleration force, centrifugal force and centripetal force.

Electrical force can be provided by interaction of an applied electric field, including an electric field with field gradients, with dielectric particles provided within the gel matrix of GMDs, or more generally by interaction with charge groups associated with the gel matrix or coupling entities provided within GMDs. Gravitational force, non-rotational force, centripetal force or centrifugal force and sedimentation force can all be applied by utilizing gel matrix composition having different mass density than the surrounding aqueous medium and providing the corresponding physical force field or acceleration. Magnetic force can by applied by providing coupling entities within GMDs, said coupling entities having diamagnetic, paramagnetic or ferromagnetic properties different from the aqueous medium which surrounds the GMDs. Representative coupling entities for applying a magnetic force are magnetic particles, magnetic granuals, ferrofluid inclusions and the like. A preferred embodiment comprises magnetite ($Fe_2O_4$) particles within GMDs. Alternatively, magnetic force can be applied directly in those cases wherein the diamagnetic, paramagnetic, ferromagnetic or electrical conductivity properties of GMDs differs from the diamagnetic, paramagnetic, ferromagnetic or electrical conductivity properties of the aqueous medium which surrounds the GMDs. Acoustic forces can be applied by applying sound or acoustic fields which preferentially interacts with the gel matrix of GMDs, or with coupling entities contained within GMDs, such that the inclusion of said coupling entities results in GMDs having a different mass density, or different mechanical compliance, than the aqueous medium which surrounds the GMDs. Optical pressure force can be applied by utilizing optical radiation which interacts with the gel matrix or coupling entities contained within the GMDs, or with the larger biological entities contained within the GMDs (see, for example, Ashkin et al, Nature 330: 769-771, 1987). Sedimentation field flow fractionation force can be provided by simultaneously utilizing a hydrodynamic force and a sedimentation force (see, for example, Levy and Fox, Biotech. Lab. 6:14-21, 1988), and can be used to separate GMDs.

After one or more exposures to one or more compounds, and following one or more incubation periods with or without controls, the MDs, that is LMDs and GMDs, are exposed to one or more staining processes, which are described elsewhere in this application, but, as also described elsewhere, if naturally occuring signals are adquate, the staining processes are omitted.

Following exposure of the GMDs to suitable stains, individual GMDs are individually measured, or measured in small groups, provided that the probability of finding more than one cell-containing GMD in the group is small. In the exemplary case of cells stained by fluorescent compounds, optical analysis such as digital fluorescence microscopy or flow cytometry is used to analyze individual GMDs, using a wavelength band sufficiently different from that used for any detection of measurement of GMD properties so that simultaneous, or serial, measurement of GMD properties and of cells with said GMD are possible. The associated fluorescence signals are acquired and analyzed, with correction for spectral overlap if necessary, by conventional means.

The magnitude of the optical signal due to the cell stain in each GMD, or small group of GMDs, is compared to the fluorescence of individual cells, whether or not such individual cells are entrapped in GMDs, thereby providing a calibration. Comparison of the GMD signal magnitude to that of individual cells provides the basis for determination of growth of individual cells, for which the growth determination can often be made within about one generation time, but without a need for significant prior culture to obtain large numbers of cells, and growth can also be determined over several generations if desired.

By making a large number of such individual cell growth determinations, the distribution of growth rate, distribution of lag time, and the plating efficiency caused by the exposure to one or more compounds or agents can be automatically determined by computer calculation. Other measurements relating to cell survival and cell death, particularly vital stains such as transmembrane potential stains, membrane exclusion stains and intracellular enzyme activity responsive stains, can also be used. Manual or visual inspection and scoring of GMDs can also be used, but is relatively labor intensive and therefore more prone to error. Thus, the preferred process is that conducted using the automated measurement means.

Similarly, measurements, assays, tests and isolation procedures directed towards the use of biological entities for the production of desirable compounds, or the use of biological entities to provide processes directed towards the degredation or modification of undesirable compounds, such as toxic wastes, can benefit from biological or biochemical activation of the biological entities, which activation comprises a form of influence on the biological entities.

Homogeneous Specific Binding Assay

This invention can be used to provide measurement of certain types of biological entities, herein refered to as analyte entities, capable of reacting with and binding two or more labled specific binding molecules, wherein the labeled specific binding molecules are measured directly by measuring one or more labels which have been attached to the individual labeled specific binding molecules, or are measured indirectly through the subsequent binding of additional, labeling molecules which can bind to, and thereby label, the labeled specific binding molecule. Examples of suitable specific binding molecules are antibodies, antigens, nucleic acids, avidin-biotin, enzyme inhibitors and lectins A key property of analyte entities is that the analyte entities have two or more specific binding sites which can bind labeled specific binding molecules during the time required toから MDs from a sample containing the labeled specific binding molecules.

Although the process of this invention is general, applicable to many types of specific binding molecules, this invention is most readily described or illustrated in terms of its application to immunoassays. For example, the process of this invention is illustrated by considering a analyte entity with two distinct epitopes. In the case of labeled labeled specific binding molecules, a sample containing the analyte entity is exposed to two different labeled antibodies, with one antibody specific for each of the two distinct epitopes. Following mixing, if desired, and after waiting for diffusion, encounter and binding of the labled antibody molecules, the analyte entities have a high probability of being specifically labeled with two labels because of the binding of the two labeled antibodies.

MDs are then formed, using methods described elsewhere in this disclosure, such that at least some of the MDs have a high probability of being individually occupied by the so labeled analyte entities. One or more measurements of the amount of label in each MD is then made, such that the measurement is capable of resolving the difference of one label from two labels, and other measurements are made which allow the measurement of each MD volume, or the volume of each group of MDs It is preferred to measure individual MDs for volume and enzyme activity, but in some cases two or more MDs can be measured together Such measurement is used to characterize each MD according to the number of labels contained, for example 0, 1, 2 or more than 2 labels. Statistical analysis, such as that based on Poisson statistics, is then employed with the measured frequency-of-occurence distribution for $n_F=0$ and $n_F=1$ to predict the number of MDs in each volume range which should have $n_F=2$ because of a random distribution.

This random prediction is then compared to the measured frequency-of-occurrence, and the excess over random is attributed to the binding of two labeled antibodies to the analyte entity. This excess frequency-of-occurrence is then used with statistical analysis to compute the concentration of analyte entities in the solution or suspension from which MDs were formed, and is further corrected by computation, if necessary, for any dilution that was made while preparing the solution or suspension, thereby measuring the concentration of the analyte entities in the sample.

Although a variety of suitable $V_{MD}$ measurement processes are described elsewhere in this disclosure, in some cases it is useful to measure one or more positive optical signals associated with molecules contained within microdroplets and/or one or more negative optical signals associated with molecules contained in a fluid surrounding microdroplets, such as has been partially described previously as "negative fluorescence" (Gray et al (Cytometry 3: 428–434, 1983)

In order to describe this invention we use the following notation.

An: Subscript denoting analyte (molecule, virus, cell, etc.)
BS: Subscript denoting binding sites on the analyte.
F: Subscript denoting free or unbound LSBMs (Labeled Specific Binding Molecules)
L: Subscript denoting label of LSBMs
$n_{An}$: Particular number of analyte entities in a MD.
$\bar{n}_{An}$: Average or mean number of analyte entities in a MD.
LSBM: Labeled specific binding molecule (e.g. labeled antibody).
$n_F$: Particular number of unbound LSBMs in a MD.
$\bar{n}_F$: Average or mean number of unbound LSBMs in a MD.
$N_{BS}$: Number of binding sites on analyte capable of binding LSBMs.
$n_{L,total}$: Total number of labels found within a MD $(=n_F+N_{BS}n_{An})$
$\bar{n}_{L,total}$: Average or mean number of labels found within a MD.
S: Signal obtained from a particular MD.

A property of many solutions and suspensions is that LSBMs and analyte entities are distributed randomly within the solutions and suspensions if the LSBMs and analyte entities are free. As used herein, the term free means that the LSBMs and analyte entities are not bound, and includes the absence of binding of LSBMs to analyte entities. For the general case in which the formation of MDs divides the solution or suspension from which MDs are formed randomly into the small volumes of MDs, the probability of unbound or free LSMBs occupying MDs is well described by the Poisson formula.

More specifically, if unbound LSBMs are randomly distributed, the probability of finding exactly $n_F$ unbound LSBMs in any MD is, $$P_F(n_F, \bar{n}_F) = \frac{(\bar{n}_F)^{n_F} e^{-\bar{n}_F}}{n_F!} \qquad (9)$$

where the mean occupation is $\bar{n}_F$, $\bar{n}_F = V_{MD}\rho_F$ with $V_{MD}$ a microdroplet volume, and $\rho_F$ is the concentration of all the free or unbound labeled specific binding molecules in the general case wherein $N_{BS}$ different binding sites (e.g. epitopes) are exploited, $N_{BS}$ different LSBMs are used at the same concentration, and therefore the concentration of unbound label in a MD with no analyte entitity is $N_{BS}\rho_F$.

Likewise, for randomly distributed analyte entities $$P_{An}(n_{An}, \bar{n}_{An}) = \frac{(\bar{n}_{An})^{\bar{n}_{An}} e^{-\bar{n}_{An}}}{n_{An}!} \qquad (10)$$

so that $\bar{n}_{An} = V_{MD}\rho_{An}$ where microdroplet volume, and $\rho_{An}$ is the concentration of the analyte. The variable $n_{An}$ is random for a well mixed system, and is therefore independent of $n_F$.

The total number of measureable labels remains constant, unless one or more degradative reactions occur, thereby modifying labels so as to effect the measureable properties of the labels. Further, it is well known that non-specific binding can sometimes occur if macroscopic solid surfaces or microscopic entities such as certain cell surfaces, virus surfaces and/or molecules are present. Such undesirable effects can also decrease the amount of free label. Generally, however, the combination of label degradation and non-specific binding of LSBMs can be made small by avoiding the use of macroscopic solid surfaces, since the occurrence of label degradation is relatively rare. Thus, although a general condition is that total amount of LSBM is conserved. In many cases essentially all of the LSBMs exist free in solution or are specifically bound to analyte entities.

Although it is not generally necessary, it is often preferred to carry out an additional step following the reaction of LSBMs with analyte entities. This additional step comprises reducing the concentration of the free LSBMs, so that the concentration of free LSBMs relative to the concentration of LSBM-analyte is reduced prior to formation of MDs. In this way, a relatively high concentration of LSBMs can be first employed in order to more rapidly drive the specific binding reactions which lead to the LSBM-analyte entity complexes Following addition and mixing of LSBMs to a sample solution or suspension, and a subsequent incubation during which LSBMs are allowed to bind to analyte entities, it is often desirable to reduce the concentration of the remaining unbound or free LSBMs. This can be accomplished by the additional step of adding purging entities, such that free LSBM encounters and binds to the purging entities. Suitable purging entities include beads, non-biological particles, crystals, nonaqueous fluid inclusions, viable cells, dead cells, inactive cells, virus, spores, protoplasts and vesicles, which have surfaces with tightly bound molecules capable of tightly binding labeled specific binding molecules. By using one or more additional signals (e.g. light scattering, fluorescence) to distinguish the purging entities, the label signals associated with the purging entities can be ignored during analysis of the measurements. Alternatively, if the purging entities bind significantly larger numbers of label than analyte, the analysis of measurements can distinguish such larger numbers of labels, and will not confuse such labels associated with LSBM-analyte complexes.

A general attribute of the process of this invention is that it is not necessary to accurately know the concentration of the LSBMs, since the concentration of LSBM-analyte complexes is the information sought. More specifically, although the provided concentration of the LSBMs is readily known, the concentration following reaction with and binding to analyte is generally not known. This is further less known following the use of any purging entities. However, it is often desirable to know that concentration of label in order to provide corrections to the measurements. An advantage of this invention is that the frequencies-of-occurrence of label is determined using many MDs, often of significantly different volumes, $V_{MD}$, such that subsequent analysis of such frequencies-of-occurrence allows computation of $\rho_{LSBM}$.

The process of this invention is illustrated by considering MDs with a range of volumes from $V_{MD}$ to $V_{MD} + \Delta V_{MD}$, such that following exposure of the sample to LSBMs and the subsequent step, if desired, of adding purging entities, this range is characterized by $\bar{n}_F = 0.15$, $\bar{n}_{An} = 0.15$ and $N_{BS} = 2$. In this case the Poisson formula predicts the following probabilities.

| $n_F$ | $P(n_F, \bar{n}_F = 0.15)$ | $n_{An}$ | $P(n_{An}, \bar{n}_{An} = 0.15)$ |
|---|---|---|---|
| 0 | 0.8607 | 0 | 0.8607 |
| 1 | 0.1291 | 1 | 0.1291 |
| 2 | 0.00968 | 2 | 0.00968 |
| 3 | 0.000484 | 3 | 0.000484 |

In this illustration a MD with zero analyte thus has a probability of about 0.0097 of having two labels through random occupation by LSBMs, and the same volume MD has a probability of 0.1291 of having two labels through occupation by one analyte entity. The excess probability of two labels resulting from LSBM-analyte occupation compared to random occupation by two free LSBMs is $$\Delta P = P(n_{An} = 2, \bar{n}_{An} = 0.15) - P(n_F = 2, \bar{n}_F = 0.15) = 0.119 \qquad (11)$$

Thus, if a sufficiently large number of occupied MDs are measured, the difference in probabilities can be measured by measuring the corresponding difference in frequency-of-occurrence of the measured and that predicted based on the measured frequency-of-occurrence of $n_F = 0$ and $n_F = 1$.

Continuing this illustration, the Poisson probabilities for $n_F = 0$, $n_F = 1$ and $n_F = 2$ are $$P(n_F = 0, \bar{n}_F) = e^{-\bar{n}_F} \qquad (12)$$

$$P(n_F = 1, \bar{n}_F) = \bar{n} e^{-\bar{n}_F} \qquad (13)$$

$$P(n_F = 2, \bar{n}_F) = \tfrac{1}{2}(\bar{n}^2 e^{-\bar{n}_F}) \qquad (14)$$

The probability of measuring two labels resulting from random occupation is thus related to the probabilities for measuring zero randomly occuring label, and for measuring one randomly occuring label through the equation $$P(n_F = 2, n_F) = \frac{1}{2} \frac{[P(n_F = 1, n_F)]^2}{[P(n_F = 0, n_F)]} \quad (15)$$

The mean or average occupation, $\bar{n}_F$, of randomly occuring label can be obtained from the mathematical relation $$n_F = \frac{P(n_F = 1, n_F)}{P(n_F = 0, n_F)} \quad (16)$$

The experimentally measured frequency-of-occurrence of $n_F=0$, $n_F=1$ and $n_F=2$ can now be quantitatively compared with the probabilities obtained by computation using the Poisson probabilities. More specifically, the experimentally measured frequency-of-occurrence, $f(n_F)$ and the Poisson formula are utilized to compute the difference between measured frequency-of-occurrence and the theoretical random frequency-of-occurrence. This can be used to interpret the difference, if statistically significant, to the occurrence of MDs with complexes of analyte and $N_{BS}$ LSBMs. This is accomplished by measuring the frequencies-of-occurrence and then computing first the mean value $n_F$ associated with random occurrence, i.e.

$$\bar{n}_F = \frac{f(n_F = 1)}{f(n_F = 0)} \quad (17)$$

and then using this in computing the difference $$\Delta f(n_F = 2) = f(n_F = 2) - P(n_F = 2, \bar{n}_F) = \quad (18)$$

$$f(n_F = 2) - \frac{1}{2} \frac{f^2(n_F = 1)}{f(n_F = 0)}$$

This measured difference is used with the total volume, $V_{MD,total}$, of measured MDs in the volume range $\Delta V_{MD}$ to compute the concentration of analyte. More specifically, $$V_{MD,total} = \sum_{i=1}^{i=N} V_{MD,i} \quad (19)$$

wherein N MDs are measured within the volume range $V_{MD}$ to $V_{MD} + \Delta V_{MD}$. Continuing this illustration further, the analyte concentration, $\rho_{An}$, is computed from $$\rho_{An} = \frac{\Delta f(n_F = 2)}{V_{MD,total}} \quad (20)$$

and thereby achieves the desired result of measuring the analyte concentration.

Continuing this illustration still further, the error in the measurement of $\rho_{An}$ can be estimated by using well-known methods of error analysis. As shown above, the determination of $\rho_{An}$ depends on measured frequencies-of-occurrence and measured MD volumes. Thus, the error in determining $\rho_{An}$ can be computed using well-known propagation-of-error methods, so that the overall result of the process of this invention is a measurement of $\rho_{An}$, and also a determination of the error in the measurement.

More generally the process of this invention utilizes measurement of frequencies-of-occurrence in MDs, and also measurement of MD volumes, such that comparison between random occupation of MDs by label and non-random occupation of MDs by label can be made. One general process, useful in cases wherein the average occupation by free label, $\bar{n}_F$, is less than one, utilizes the mathematical recursion relation for the Poisson formula, here used with the abbreviated notation $P(n) \equiv P(n, \bar{n})$, so that the recursion relation is $$P(n + 1) = = \frac{\bar{n}}{(N + 1)} P(n) \quad (21)$$

so that on average the measured frequency-of-occurrences for random events will be related by $$f[(n + 1)_F] = \frac{f(1)}{f(0)(n + 1)} f(n) \quad (22)$$

and can be straightforwardly used to compute the excess over random for occupation of MDs by label over a wider range of occupation.

An alternative method for providing statistical analysis of the MD measurement is useful in the case wherein significant measurement error, $\delta f(n_F)$, in the frequency-of-occurrence is expected. This alternative method utilizes well-known averaging methods, which reduce error. The occurrence of free LSBMs and analyte entities within a MD are statistically independent, so that the probability of having a particular combination of $n_F$ free label or free LSBMs and $n_{An}$ analyte entities such that the total amount or number of labels is $n_L = n_F + N_{BS} n_{An}$. This emphasizes that different combinations of $n_L$ and $n_{An}$ can result in the same $n_F$, and indicates that in order to compute the probability of a given value of $n_L$ a summation over the different possibilities giving the same $n_L$ is needed.

A basic property of this approach is the recognition that $n_L$ is a linear combination of $n_F$ and $n_{An}$, and that therefore the probability function for $n_F$ is given by the convolution of $P_F(n_F, \bar{n}_F)$ and $P_{An}(n_{An}, \bar{n}_{An})$. Thus, using well-known results of fundamental probability theory, the average values $\bar{n}_L$, $\bar{n}_F$ and $\bar{n}_{An}$ are related by $$\bar{n}_L = \bar{n}_F + N_{BS} \bar{n}_{An} \quad (23)$$

and the variances of these same three parameters are related by $$var(n_L) = var(n_F) + N_{BS}^2 var(n_{An}) \quad (24)$$

where the variance is a measure of the spread or statistical error which is expected. By using the above two mathematical relations, and measurements of frequencies-of-occurrence to obtain determinations of $\bar{n}_L$ and $var(n_L)$, the parameter $\bar{n}_{An}$ can be computed. This computed value is used in Poisson statistics formulae with measured values of $V_{MD}$ to compute $\rho_{An}$.

The statistical error in the average and the variance is well characterized according to fundamental probability theory, and can be used with propagation-of-error analysis to compute the error in $\rho_{An}$.

Both monoclonal and polyclonal antibodies with labels can be used as LSBMs in this invention. If monoclonal antibodies are used, $N_{BS}$ is known exactly, as is the average number of labels per LSBM. However, in the related case wherein LSBMs are polyclonal antibodies, somewhat different numbers of antibodies may bind, with varying avidities, to individual analyte entities, such binding by different numbers, however, can generally be characterized by an average or mean number of binding sites, $\overline{N}_{BS}$. The value of $\overline{N}_{BS}$ is determined from initial, calibrating experiments, as it is recognized that there may be some variation in the actual number of bound LSBMS, that is, there may be a distribution, $N_{BS} = \overline{N}_{BS} \pm \delta N_{BS}$ around $\overline{N}_{BS}$. In this case, measurement of frequencies-of-occurrence results in a superposition of (1) a random distribution, consistent with the Poisson formula for free label, and (2) a peaked distribution located at $N_{BS}$ with width $\delta N_{BS}$.

A general computational process can be utilized with the measurements of the frequencies-of-occurrence and MD volumes, as both $\overline{N}_{BS}$ and $\delta N_{BS}$ are first determined in a calibrating process. The frequency-of-occurence measurements are then compared self-consistently, by well known computational means, to a general probability distribution. This comprises a linear superposition of a Poisson function for free label and for analyte wherein the average analyte has bound $\overline{N}_{BS}$ labels. More specifically, the measured distribution is fit to $$P(L)_{fit} = P_F(n_F, \overline{n}_F) + N_{BS} P_{An}(n_{An}, \overline{n}_{An}) \quad (25)$$

Subtraction of the Poisson formula $P_F$ thereby results in determination of $P_{An}$. The value of $\overline{n}_{An}$ is obtained from $P$ sub bound, and in combination with $V_{MD}$ for the range of MD volumes used, yields the desired analyte concentration $\rho_{An}$.

This process is further illustrated by the case wherein the analyte biological entity is a macromolecule with three distinct, non-overlapping epitopes for which three non-cross reacting antibody molecules are assumed. It is preferred to supply each of the three antibody molecules at a concentration approximately equal to ten times the largest expected analyte concentration. Thus, if the largest expected analyte concentration is about $\rho_{An} = 10^{-9}$ Molar, then each of the three antibodies is provided at a concentration of about $10^{-8}$ Molar. Following addition of the three antibodies to the sample, the resulting preparation is mixed, and an incubation time of about 10 seconds to 3 hours, preferably about 2 minutes to 20 minutes, is utilized. This allows diffusional encounter and an opportunity for the antibodies to bind to the analyte. Following this specific binding incubation, any reagents or gelable material, if desired, are added. The resulting preparation is mixed, and MDs are formed by any of the several methods described elsewhere in this disclosure, but preferably by dispersion into a non-aqueous fluid. Generally, it is preferred to measure small MDs, for which the probability difference for specifically bound label and randomly distributed label is largest. That is, the difference $$\Delta P = P_{An}(n_{An}, \overline{n}_{An}) - P_F(n_F, \overline{n}_F) \quad (26)$$

is the probablistic basis for measuring analyte through the highly improbable association of $N_{BS}$ labels within a MD compared to the probability of random occurrence.

Although it is preferred to carry out the process of this invention by using equilibrium conditions, or close to equilibrium conditions following exposure of analyte to LSBMs, it is also possible to utilize conditions far from equilibrium. In such non-equilibrium cases, a sample containing analyte can be exposed to LSBMs for a significantly shorter time than needed for equilibrium, or for being close to equilibrium, and fewer completed complexes of analyte and $N_{BS}$ LSBMs are formed. That is, not only are fewer complexes with exactly $N_{BS}$ LSBMs formed, there are more incomplete complexes formed wherein less than $N_{BS}$ LSBMs are bound to each analyte entity. In spite of these less desirable attributes, a non-equilibrium measurement can be accomplished by the further step of making quantitative comparison, with otherwise the same non-equilibrium conditions, to one or more calibrating measurements employing known concentrations of analyte.

The measurement process of this invention can be applied to very low concentrations of analyte molecules, as analyte molecules can be actually counted. In addition, the measurement can be made in solution without the use of a solid phase which must be washed. Further, because the measurement process can involve a counting process, the invention provides means for measurements over a large dynamic range of analyte concentrations, that is, from high concentrations to orders of magnitude lower concentrations.

Prior to the carrying out of the process of this invention, two or more labeled specific binding molecules are obtained, using means well known in the art, such that two or more labeled specific binding molecules are prepared, which are capable of binding to two or more binding sites on the analyte. In the important case wherein LSBMs are antibodies, this requirement corresponds to using antibodies which bind to at least two non-overlapping epitopes on the analyte, such that at least two antibodies can be simultaneously and specifically bound to the analyte. Examples of such labeled specific binding molecules include (a) monoclonal antibodies with about one label molecule bound to each antibody molecule, (b) antigen molecules with about one label molecule bound to each antigen entity, (c) monoclonal antibodies with about two label molecules of the same type are bound to each antibody molecule, (d) antigen molecules with about two label molecules of the same type bound to each antigen entity, and (e) polyclonal antibodies containing at least two antibodies capable of binding to at least two non-overlapping epitopes of the analyte entity.

Many different types of antlyte entities can be measured by the process of this invention. More specifically, analyte entities with at least two non-overlapping and non-competing specific binding sites can be measured. In the important general class of analyte entities consisting of antigens for which the LSBMs are labeled antibodies, antigenic analyte entities capable of independently binding antibodies at two or more different sites can be measured. Examples of such analyte entities with two such sites include all antigens capable of assay by a sandwich assay, for example creatine kinase and hCG (human chorionic gonadotrophin). Examples of such analyte entities with three such sites include proinsulin and the $\beta$-subunit of TSH (thyrotropin). In the case of small molecules such as haptens, the assayed analyte entity with two or more specific binding sites may consist of a hapten-carrier molecule complex.

Alternatively, if an analyte entity has multiple occurrence of one or more binding sites, LSBMs with the same or different labels can be used to multiply bind to each analyte entity. For example, an antigenic polymer may have one or more multiple eptitopes, such that the same antibody can specifically bind at multiple sites on the polymer, so that such an antibody can be used in the process of this invention. Continuing this illustration, one or more labeled specific binding molecules in the form of one or more labeled antibody molecules are exposed to the analyte solution or sample, such that the antibody molecules can bind at two or more repeated specific binding sites on the polymer, thereby associating two or more labeled specific binding molecules with each analyte molecule. Other analytes with repeated binding sites include cells and viruses.

In the general practice of this invention, analyte entities such as cells, organelles, viruses, nucleic acids, antibodies, enzymes, structural proteins, hormones and drugs can be measured First, a sample containing such analyte entities is converted into a liquid solution or liquid suspension by any of the standard, well known means for preparing analyte samples. The resulting analyte preparation is then exposed to labeled specific binding molecules, such that there is a high probability, following mixing and waiting for diffusion to occur, that at least two LSBMs can bind to each analyte entity, thereby forming analyte entity-complexes which contain at least two LSBMs. Second, some or all of this-reacted preparation can then be used to form MDs, such that there is a high probability that at least one MD, and preferrably at least $10^3$ MDs, is individually occupied by an analyte entity-LSBM complex. Third, measurement means capable of measuring at least one LSBM is preferably utilized to measure MDs, and also the volumes of the MDs, such that by using statistical analysis, such as Poisson statistics the occupation by LSBMs, and the associated volumes of the MDs, can be determined. Computation can then be used to compare the measured frequency-of-occurrence of LSBMS for LSBMs occuring singly and for LSBMs occuring multiply, such that the excess of multiple occurances above that due to random occurrence is attributed to the specific binding of LSBMs to analyte entities. The number of such above-random occurrences is then used with statistical analysis to compute the number of analyte entities with bound LSBMs. This is combined with the volume of analyzed MDs to yield the number of analyte entities per volume in the preparation from which MDs were formed, which number per volume is the concentration of the analyte entities.

In another version of this process, it is only required that measurement means be capable of measuring $N_{BS}$ labels, as this measurement sufficies if the occurrence of free label within MDs obeys $\bar{n}_F < N_{BS}$.

Labels for LSBMs suitable for use with this invention include enzyme activity, biological activity and fluorescence. Fluorescence can be readily measured when large numbers of fluorescent molecules are present, but it becomes increasingly more difficult for smaller numbers. Thus, the present detection limit is about $10^3$ molecules for fluorescein measured in a flow cytometer, but still lower for measurement apparatus such as quantitative fluorescence microscopy. A fundamental limit appears to relate to the number of fluorescence emission photons emitted before photodamage occurs, but it may be possible to measure individual fluorescent molecules such as phycoerythrin (see Mathies et al in *Fluorescence in the Biomedical Sciences*, Liss, pp. 129-140, 1986). Thus, measurement based on singly or multiply labeled specific binding reagents wherein an analyte molecule specifically binds several labeled specific binding molecules is feasible. For example, by attaching an average of three fluorescent labels to each of three different antibodies, nine fluorescent label molecules become associated with each reacted analyte molecule. These can be readily measured by methods directed towards measurement of individual fluorescent molecules.

In general, however, the magitude of fluorescence signal associated with measurement of a fluorescence label is much too small. For this reason, the preferred embodiment of this invention involves the use of an active label, such as analyte activity related to vesicles, phage or biochemical activity. It is preferred to utilize one or more active enzymes, such that at least one enzyme label is measured through the use of optical measurements such as light scattering, light absorbance or colorimetric, fluorescence, time-delayed fluorescence, phosphorescence and chemiluminescence, but particularly fluorescence In much of the following description the invention is described in terms of an enzyme label, wherein the activity of at least one type of enzyme molecule provides the basis of measurement of the label, and is generally well known for use in macroscopic or non-microdroplet cases Such enzyme activity measurement is accomplished generally by accumulating fluorescent product of one or more enzyme catalyzed reactions within a MD containing the enzyme, and generally requires an incubation period during which the fluorescent product or fluorescent products can accumulate It is preferred to provide conditions for a kinetic analysis, wherein substrates, co-factors, etc. are provided under conditions that will allow the enzyme catalyzed reaction to proceed at the maximum reaction velocity, which is at a rate equal to the turnover number for the enzyme. Under these conditions, product accumulation occurs linearly with time until product inhibition, substrate depletion, or other well-known enzyme reaction effects occur. Generally it is preferred to utilize measurements of MDs which have a high probability of being unoccupied or individually occupied by analyte entities, that is, containing less than two analyte entities.

In addition to utilizing enzyme activity measurement directly, wherein one or more enzyme labels are measured by measuring one or more reactants of the corresponding enzyme catalyzed reactions, larger signals can generally be obtained by using enzyme channeling and/or enzyme cycling, both of which methods are well established for bulk solution use but have not previously been suggested or demonstrated for use in MDs to measure individual, or small numbers of, enzyme molecules. Enzyme channeling, or use of linked enzyme reactions, consists of providing additional types of enzymes, such that a product of a first enzyme catalyzed reaction serves as a substrate for a second enzyme catalyzed reaction, and a product of the second enzyme catalyzed reaction serves as a substrate for a third, and so on. Likewise, the well established method of enzyme cycling provides amplification for measuring enzyme labels by utilizing a cyclic reaction process wherein the product of a first enzyme catalyzed reaction is a substrate or cofactor for a second enzyme catalyzed reaction, and a product of the second reaction is in turn a substrate for the first (see, for example, Siddle in *Alternative Immunoassays*, Collins (Ed.), Wiley, 1985). In either case, larger amounts of reaction product can be obtained within a MD. In order to utilize this version of the invention, additional enzymes, substrates, cofactors and the like are provided in the sample, if not already present, so as to ensure that these additional enzyme reactions reactants and enzyme will be present in each MD.

A sample containing particular analyte molecules whose analysis is desired, can be converted into an aqueous solution or suspension by any of a number of well known means, such as tissue homogenization, stirring, dissolution, and the like.

During or after the above treatment which yields a liquid solution or liquid suspension form of the sample, labeled specific binding molecules with enzyme labels are added to, and thoroughly mixed with the sample. The enzyme labeled specific binding molecules are provided in sufficient quantity, based on the expected maximum amount of the analyte molecules, so that essentially all of the analyte entitys will have reacted with and thereby bound the enzyme labeled specific binding molecules within about 10 seconds to 3 hours, and, under more optimal conditions, about 2 minutes to 20 minutes.

Although substrates and/or cofactors for the enzymes catalyzed reactions can be added in prior steps, it is preferable to add these reactants just prior to creation of liquid or gel microdroplets, in order to minimize the amounts of enzyme products are formed which would be distributed into essentially all of the liquid or gel microdroplets, and which would result in an undesireable high background fluorescence signal in all liquid or gel microdroplets.

A variety of methods can be used to measure the volumes of the MDs with and without LSBMs. The generation of some background, that is, fluorescence present uniformly in essentially all liquid or gel microdroplets, is sometimes desirable, as such background provides a means of measuring the volume of microdroplets. In this case, all MDs have a low level of fluorescence, while MDs containing LSBMs, either unreacted or reacted so as to have bound with analyte analyte entities, have increased fluorescence. This is associated with the enzyme label catalyzing a reaction which has one or more fluorescent products, or is coupled to one or more reactions which increase fluorescence.

In much of the measurement process it is possible to measure individual MDs, or to measure groups of MDs, with the latter often preferable if the sample concentration of analyte entity is low, as in that case relatively few MDs are occupied by analyte entities. In the following section the quantity $V_{group}$ refers to the total volume of a group of MDs which are measured together, and it is understood that a group of MDs can contain a number of MDs which is in the range 1 to 100 MDs, preferably 1 to 10 MDs.

As an alternative to utilizing background fluorescence from one or more enzyme reactions for detection of, and measurement of $V_{group}$ for each analyzed MD group, one or more fluorescent molecules can also be provided at low concentration in the solution or suspension prior to creation of MDs. This background concentration is selected to correspond, in the largest MD groups, to an amount which can be distinguished from the fluorescence produced by one or two enzyme molecules within the volume of the largest MD groups used in the analysis.

As another alternative, a fluorescent molecule type with fluorescence properties distinct from those used in enzyme assays within MD groups can be used to provide detection of, and measurement of $V_{group}$ of each MD group. This is useful for subsequent mathematical processing of the measurement data from a number of individual MD groups.

The aqueous solution/suspension form of the sample is then used to create LMDs or GMDs by any of several methods described elsewhere in this disclosure. A preferred method is to add agarose, any tracer entities, reagents for enzyme assays, and the like, and to disperse the resulting solution/suspension in mineral oil or silicone fluid.

The resulting MD preparation is then incubated to allow the enzyme catalyzed reaction(s) to proceed, such that fluorescent product(s) accumulate preferentially in those MDs which contain enzyme labeled specific binding molecules. Depending on the capabilities of the optical measurement apparatus, and on the turnover number of the enzyme(s) used, the incubation time can range from about 30 minutes, or less, up to several hours.

There are a variety of choices of enzymes and measurement apparatus attributes. However, all are subject to the condition that either individual enzyme molecule activity is measured, or that a sufficiently large number of enzymes are bound to individual analyte entities by enzyme labeled specific binding molecules that only this largeer number is measured within each analyte occupied MD group. Desirable properties of an enzyme include high turnover number, stability, and specificity.

Following an incubation period some or all of the MD groups are measured optically, preferably using in an appratus with quantitative image analysis capability. Representative suitable apparatus includes flow cytometry apparatus, flow-through-microfluorimetry apparatus, optical particle analyzers apparatus, fluorescence microscopy apparatus, light microscopy apparatus, image analysis apparatus and video recording apparatus.

An important aspect of detection and measurement of one or more individual enzyme molecules was not explicitly mentioned or discussed in the prior art (see Rotman, PNAS 47: 1981–1991, 1961). Specifially, it has not been disclosed that it is important to use conditions wherein the spontaneous rate of fluorescence production is sufficiently small that the catalytic effect of a single enzyme molecule in a small volume can be distinguished against the background, generally increasing with time, due to the spontaneous rate of fluorescence production. Such a spontaneous rate generally occurs for fluorgenic substrates, wherein the non-fluorescent fluorogenic substrate spontaneously decays, and generates the same fluorescent molecules as the enzyme catalyzed reaction. Methods for avoiding significant spontaneous fluorescence have not been generally appreciated, or even explicitly acknowledged. Therefore, suitable methods for minimizing spontaneous fluorescence are described as part of the present invention.

One general method is to determine, and then utilize, enzyme catalyzed reactions for which the fluorogenic substrates under the conditions of the assay yield fluorescence sufficiently small so that the fluorescence due the product molecules catalyzed by one enzyme molecule is detectable. In this approach, it is fundamental to consider the volume, $V_{group}$, which contains the enzyme labeled specific binding molecule. The spontaneous rate of fluoresence accumulation is proportional to $V_{group}$, while the enzyme catalyzed rate is, to a good approximation, independent of $V_{group}$.

It is preferred to use a quantitative fluorescence microscope with image analysis capability wherein the amount of fluorescence emission from individual MDs, or groups of MDs, can be automatically measured. Alternatively, a flow cytometer with capability of measuring fluorescence at low levels can be used, such that the fluorescence associated with the accumulated product in a MD group due to one enzyme molecule can be detected, and distinguished from background fluorescence. Optical measurement apparatus which allows detection of, for example, $10^4$ to $10^5$ fluorescein molecules is well known (see, for example, Shapiro, Practical Flow Cytometry, Liss, New York, 1985).

It is preferred to use an enzyme such as β-galactosidase, with the fluorgenic substrate fluorescein-di-b-D-galactopyranoside, fluorescein is the fluorescent product, has a large quantum yield, and is readily detected and measured at the level of $10^4$ to $10^5$ fluorescein molecules (see, for example, Shapiro *Practical Flow Cytometry*, A. R. Liss, New York, 1985). Another useful substrate is FITC-diacetate (fluorescein isothiocyanate-diacetate), which has the further desirable property of binding strongly and non-specifically to proteins. Thus, by providing a suitable amount of inexpensive protein such as BSA (bovine serum albumin) mixed into the sample before GMDs are created, and subsequently coating the GMDs with a gel or other coating sufficient to retain BSA, a significant fraction of the FITC is intercepted and bound by the protein, so that an enzyme occupied GMD accumulates detectable GF.

Another useful enzyme catalyzed reaction is alkaline phosphatase utilized with the fluorgenic substrate 4-methylumbelliferyl phosphate, which catalyzes the degredation of this substrate into the fluorescent product 4-methyl umbelliferone plus the non-fluorescent product inorganic phosphate (see, for example, Guilbault *Handbook of Enzymatic Methods of Analysis*, Marcel Dekker, New York, 1976).

Following measurement of the amount of fluorescence(s) and volume, $V_{group}$, of each MD group in a preparation, the resulting data is analyzed in the following way, preferably using a computer. The individual values of $V_{group}$ are summed, thereby providing a determination of the sample actually analyzed. The amount of fluorescence(s) in each MD group is determined, with respect to previously carried out standard calibrations, so that the number of enzyme molecules in each range of volumes of MDs is determined. Typically, the MDs have volume which range from about $5 \times 10^{-10}$ to about $5 \times 10^{-7}$ ml, so that an analysis MDs of in the size (volume) ranges of typically $5 \times 10^{-10}$ to $7.9 \times 10^{-10}$ ml, $8 \times 10^{-10}$ to $1.19 \times 10^{-9}$ ml, $1.2 \times 10^{-9}$ to $1.59 \times 10^{-9}$ ml, $1.6 \times 10^{-10}$ to $2 \times 10^{-9}$ ml, and so on, is carried out mathematically. Such an analysis first makes use of the individual $V_{group}$ determinations, and divides the MD group volume range into volume intervals such that there are a significant number of MD groups in each interval. Typically, MDs created by dispersion in mineral oil have a volume distribution which rises sharply and then falls moderately with increasing $V_{MD}$, with the consequence that most MD groups have volumes just above an approximate cutoff size (e.g. 10 micron diameter, $V_{group} \approx 5 \times 10^{-10}$ ml), and that it is useful to select volume intervals of approximately a half order of magnitude in $V_{group}$, as indicated above.

The Poisson distribution, is then used with iterative computations, to find the best selfconsistent fit to each of the volume ranges. In the present case, if the concentration, or number density, of particular molecules is $\rho$, then the average number of such molecules in MD groups of volume $V_{group}$ is $\bar{n} = \rho V_{group}$. The Poisson distribution is used to describe the statistical distribution of small entities such as cells or molecules, such that the probability of finding n cells or molecules in a volume $V_{group}$ is given by $P(n, \bar{n})$. For purposes of interpreting measurements on a number of MD groups, n is the number of enzyme molecules found in each MD group, and $\bar{n}$ is the subsequently computed average number of enzyme molecules for each value of $V_{group}$. Measurements of MD groups without enzyme molecules (n=0) and MD group with one enzyme molecule (n=1) are used with the Poisson distribution equation to predict the statistical frequency with which multiple enzyme occupation of MD groups will occur due to random occupation. That is, the number of randomly occuring cases of n=2, n=3, n=4, etc. are computed.

The number of MD groups found by measurement of fluorescence of individual MD groups to contain n=2, n=3, etc. enzyme labeled specific binding molecules is then used to compute a best value of $\bar{n}$ for each range (interval) of $V_{group}$ values, and then to compute the best value of $\rho$ by applying the equation $$\rho = \frac{\bar{n}}{V_{group}}. \tag{27}$$

which is the intermediate of the assay, thereby being the number of analyte entities per volume in the diluted sample. It is straightforward to then compute a correction factor, $f_D$, $$f_D = \frac{V_S}{V_S + V_{group}} \tag{28}$$

for the dilution during the MD creation process, and thereby, to obtain the concentration, $\rho_{analyte}$, of analyte entity in the (original) sample.

In this way, the process of this invention provides a determination of the amount of analyte in the original sample, and is based on the determination of individual analyte entities within individual MD groups, as revealed by measurement of individual enzyme molecule activity. In order to obtain increased fluorescence it is generally preferred to provide at least one incubation, wherein the enzyme catalyzed reactions which result in altered fluorescence, usually increased fluorescence, can proceed.

Finally, in addition to providing and utilizing LSBMs, it is also possible to provide and utilize one or more types of intervening molecules, such that the intervening molecules bind to one or more sites on the analyte entity, and one or more LSBMs are subsequently used. For example, a polyclonal preparation of unlabeled mouse antibodies can be used as intervening molecules, wherein these intervening molecules are mixed with the sample so as to allow binding of these unlabled intervening molecules to binding sites on the analyte entities. A goat anti-mouse antibody with an enzyme label, or other suitable label, can also be added, such that the goat anti-mouse antibody is a LSBM.

It is often desirable to remove or purge the unbound intervening molecules, which can be accomplished by adding beads with surface-bound and unlabel goat anti-mouse antibodies. Such a purging step is generally useful, and consists of supplying purging entities such as beads, non-biological particles, crystals, non-aqueous fluid inclusions, viable cells, dead cells, inactive cells, virus, spores, protoplasts and vesicles, which have surfaces with tightly bound molecules capable of tightly binding labeled specific binding molecules, which will remove, but not necessarily all, of the unbound intervening molecules, so as to greatly reduce the occurrence of complexes of intervening molecule-LSBM which are not associated with the analyte entities.

One or more purging steps can also be used in the case that only LSBMs are used, so as to bind much, but not necessarily all, of the free or unbound LSBMs which remains after the sample containing analyte entities has been exposed to the LSBMs, but before MDs are formed.

Significantly, it is not generally necessary to remove the purging entites from the sample before forming MDs and carrying out the remainder of the process. In either the case of removing LSBM, wherein mostly free or unbound LSBMs are removed, or in the case in which unlabled intervening molecules are removed, the association of the removed LSBMs and/or intervening molecules with the purging entity provides a general means for identifying such purging entities during the measurement process. General means for distinguishing the purging entities includes measurements based on optical properties, mass density properties, acoustic properties, magnetic properties, electrical properties and thermal properties, and it is preferred to use light scattering, light absorbance or colorimetric, fluorescence, time-delayed fluorescence, phosphorescence and chemiluminescence. Thus, MDs which contain purging entities can be readily distinguished from MDs without purging entities, so that the analysis of measured MDs can utilize measurements only from MDs without purging entities as the basis for carrying out the desired assays and tests.

This invention will now be more specifically illustrated in the following non-limiting examples.

EXAMPLE I

Delivery of Water-Soluble Reagent to GMDs Surrounded by Mineral Oil

GMDs were formed in a non-aqueous fluid by first preparing a liquid gellation medium according to the following steps:
1) 1 ml of aqueous buffer (200 mM acetate buffer, pH 8) was measured out,
2) 50 mg agarose (Type VII, low melting temperature, Sigma Chemical) was added,
3) the preparation was heated to 80° C. (above the liquefaction temperature)
4) the preparation was cooled to 40° C. (still above the gelation temperature).

The enzyme alkaline phosphatase, was then added to the liquid gelation media, 10 ml of mineral oil was added, and vortexing used to produce liquid microdroplets (10–100 micron) which were gelled by cooling to about 10° C., thereby incorporating enzyme into agarose GMDs which were suspended in a tube of mineral oil (equivalent to parafin oil, heavy; Fisher; Saybold 162 min). A substrate for the enzyme, 4-methylumbelliferone phosphate, was then dissolved in a small amount of non-polar solvent (acetone or DMSO), which was then added to a second tube of mineral oil. Upon gently mixing these two tubes of mineral oil, the enzyme substrate was able to enter into the GMDs surrounded by mineral oil, and the enzyme catalyzed reaction occurred, which yielded a fluorescent product which was visible in an ultraviolet microscope after a period of a few minutes to hours, depending on the amount of enzyme activity incorporated into the GMDs. This demonstrates the delivery of a water soluble chemical (4-methylumbelliferone phosphate) into GMDs surrounded by mineral oil.

EXAMPLE II

Delivery of a Water-Soluble Compound to GMDs Using Reverse Micells

Agarose GMDs suspended in mineral oil were formed using methods similar to those of Example I. A small amount of water containing soap and a fluorescent dye were then added to a second tube of mineral oil, and then vortexed to create reverse micelles. The contents of the two tubes, one a mineral oil suspension of agarose GMDs, the other an emulsion of reverse micells in mineral oil, were then mixed, so as to cause the reverse micelles to collide with the GMDs. This allowed the fluorescent dye contained in the micelles to be delivered into the GMDs, as was observed using fluorescence microscopy.

EXAMPLE III

Rapid Delivery of Chemicals from GMDs to GMDs in Silicone Fluid

Agarose GMDs were formed by dispersion in 50 centipoise silicone fluid (Dow Corning) from a solution containing 1000 microgram per ml of 4-methylumbelliferone (Blue fluorescence emission; ultraviolet excitation) in 0.1M Tris buffer at pH 8.0, thereby yielding fluorescent GMDs surrounded by the non-aqueous fluid comprising 50 cp silicone fluid. A drop of silicone fluid containing these Blue fluorescent GMDs was placed on a hemocytometer, as was a similar drop containing non-fluorescent GMDs made by the same method, but without the 4-methylumbelliferone (non-fluorescent GMDs). The two drops were gently mixed, and the resulting mixed GMD preparation observed using a fluorescence microscope.

Initially the two types of GMDs were readily distinguished as Blue fluorescent and non-fluorescent, but within a few minutes the initially non-fluorescent GMDs gradually acquired significant Blue fluoresence, thereby indicating a fairly rapid delivery of 4-methylumbelliferone from pre-loaded GMDs to the initially non-fluorescent GMDs.

EXAMPLE IV

Slow Delivery of Chemicals from GMDs to GMDs in Mineral Oil

As in Example III, agarose GMDs were formed by dispersion, but in this case using mineral oil (equivalent to parafin oil, heavy; Fisher; Saybold 162 min). As in Example III, the solution from which GMDs were formed contained 1000 microgram per ml of 4-methylumbelliferone (Blue fluorescence emission; ultraviolet excitation) in 0.1M Tris buffer at pH 8.0, and thereby yielded fluorescent GMDs surrounded by the non-aqueous fluid comprising mineral oil. In contrast to Example III, no acquisition of Blue fluorescence by the non-fluorescent GMDs was observed over a period of several minutes. However, after remaining overnight at room temperature the originally non-fluorescent GMDs became weakly Blue fluorescent, thereby indicating a slow delivery of 4-methylumbelliferone from pre-loaded GMDs to the initially non-fluorescent GMDs.

Equivalents

Those skilled in the art will recognize, or be able to ascertain, using no more than routine experimentation, many equivalents to the specific embodiment of the invention described herein. Such equivlents are intended to be encompassed by the following claims.

We claim:

1. A method for detecting an interaction between an amphiphilic compound and at least one biological entity, comprising the steps of:
   a) disposing a biological entity in an aqueous medium, wherein the biological entity is selected from the group consisting of microorganisms, cells, protoplasts, small multicellular organisms, nucleic acid molecules, antibodies, antigens and viruses;
   b) forming the aqueous medium into microdroplets which are suspended in a non-aqueous phase, wherein the biological entity is contained within at least one of the microdroplets;
   c) introducing the amphiphilic compound into the non-aqueous phase, whereby the amphiphilic compound migrates from the non-aqueous phase into the microdroplet containing the biological entity and is partitioned between the non-aqueous phase and the microdroplet, permitting the amphiphilic compound and the biological entity in the microdroplet to interact; and
   d) detecting the interaction between the amphiphilic compound and the biological entity.

2. A method according to claim 1 comprising the steps of:
   a) dissolving the amphiphilic compound in a non-aqueous fluid, wherein the amphiphilic compound is soluble in each of the non-aqueous fluid, the non-aqueous phase and the microdroplets;
   b) contacting the non-aqueous fluid with the non-aqueous phase in which the microdroplets are suspended to permit partitioning of the amphiphilic compound between the non-aqueous fluid, the non-aqueous phase and the microdroplets, whereby the amphiphilic compound and the biological entity in the microdroplet interact; and
   c) detecting the interaction between the amphiphilic compound and the biological entity.

3. A method for detecting an interaction between a water-soluble compound and at least one biological entity, comprising the steps of:
   a) disposing a biological entity in an aqueous medium, wherein the biological entity is selected from the group consisting of microorganisms, cells, protoplasts, small multicellular organisms, nucleic acid molecules, antibodies, antigens and viruses;
   b) forming the aqueous medium into microdroplets which are suspended in a non-aqueous phase, wherein the biological entity is contained within at least one of the microdroplets;
   c) combining the non-aqueous phase and the microdroplets with an emulsion having a continuous phase which is miscible with the non-aqueous phase and a discontinuous phase which is miscible with the microdroplets and which contains the water-soluble compound, whereby at least a portion of the discontinuous phase combines with the microdroplet containing the biological entity, permitting the water-soluble compound and the biological entity in the microdroplet to interact; and
   d) detecting the interaction between the water-soluble compound and the biological entity.

4. The method of claim 3 wherein the microdroplets are aqueous gel microdroplets.

5. The method of claim 3 further comprising adding at least one measurable tracer compound to the discontinuous phase of the emulsion.

6. The method of claim 5 wherein the amount of water-soluble compound is determined by measuring the amount of the tracer compound introduced into the microdroplet.

7. The method of claim 5 wherein the measurable tracer compound is a fluorescent compound.

8. The method of claim 5 wherein the measurable tracer compound is selected from the group consisting of fluorescein, rhodamine, coumarin, lucifer yellow and phycoerythrins.

9. The method of claim 3 wherein the water-soluble compound is a substrate or a co-factor for an enzyme-catalyzed reaction.

10. The method of claim 3 wherein the water-soluble compound is selected from the group consisting of fluorescein-di-$\beta$-D-galactopyranoside, resorufin-$\beta$-D-galactopyranoside, fluorescein diacetate, carboxy fluorescein diacetate, fluorescein isothiocyanate diacetate, fluorescein digalactoside, 4-methyl umbelliferone butyrate, 4-methyl umbelliferone phosphate, 3-$\mu$-methyl fluorescein phosphate, diacetyl-2,7-dichloro fluorescein, homovanillic acid, a mixture of homovanillic acid and rhodamine lead, nicotinamide adenine dinucleotide and resazurin.

11. The method of claim 3 wherein the discontinuous phase of the emulsion is electrically charged to enhance contact with the microdroplets.

* * * * *